US011961043B2

(12) United States Patent
Dattamajumdar et al.

(10) Patent No.: US 11,961,043 B2
(45) Date of Patent: Apr. 16, 2024

(54) OPTICAL SENSING-BASED INVENTORY CONTROL SYSTEMS AND METHODS

(71) Applicant: Omnicell, Inc., Mountain View, CA (US)

(72) Inventors: Anupam Kumar Dattamajumdar, Sunnyvale, CA (US); Herbert Lawson Fisher, Portola Valley, CA (US); John Alfred D'Costa, San Jose, CA (US); Rupert P. Robin, British Columbia (CA); Brian Richard Arnold, Santa Cruz, CA (US); Sanandan Sudhir, Gujarat (IN); Shah Sohil Jayeshbhai, Gujarat (IN)

(73) Assignee: Omnicell, Inc., Mountain View, CA (US)

( * ) Notice: Subject to any disclaimer, the term of this patent is extended or adjusted under 35 U.S.C. 154(b) by 0 days.

(21) Appl. No.: 17/748,729

(22) Filed: May 19, 2022

(65) Prior Publication Data

US 2022/0351121 A1  Nov. 3, 2022

Related U.S. Application Data

(63) Continuation of application No. 16/836,912, filed on Mar. 31, 2020, now Pat. No. 11,361,278.

(51) Int. Cl.
*G06Q 10/087* (2023.01)
*A61G 12/00* (2006.01)
(Continued)

(52) U.S. Cl.
CPC ......... *G06Q 10/087* (2013.01); *A61G 12/001* (2013.01); *G06T 7/74* (2017.01); *A61G 2203/30* (2013.01)

(58) Field of Classification Search
CPC ...... G06Q 10/087; G06T 7/74; A61G 12/001; A61G 2203/30
See application file for complete search history.

(56) References Cited

U.S. PATENT DOCUMENTS

| | | | |
|---|---|---|---|
| 6,073,834 A | 6/2000 | Michael et al. | |
| 8,939,365 B1 | 1/2015 | Reese | |

(Continued)

FOREIGN PATENT DOCUMENTS

| | | |
|---|---|---|
| CN | 104889959 B | 10/2017 |
| WO | 2021202176 A1 | 10/2021 |

OTHER PUBLICATIONS

U.S. Appl. No. 16/836,912, Notice of Allowance dated Feb. 18, 2022, 9 pages.

(Continued)

*Primary Examiner* — Paul Danneman
(74) *Attorney, Agent, or Firm* — Kilpatrick Townsend & Stockton LLP

(57) ABSTRACT

An inventory tracking system includes storage modules that hold one or more items. Each item is positionable at locations within the storage modules independent of physical characteristics of the item. Inventory monitoring modules are included to monitor storage modules for adding an item, retrieving an item, consuming of the item, returning an unused item, discarding at least a portion of a consumed item, or combinations thereof. Each act is used to determine information about items utilized in the act, including the location within the storage modules of the items. Each storage module updates a central inventory database about a location of the storage module, a revised inventory of the items stored within the storage modules, or both. The location of the storage modules, the revised inventory of the items stored within the storage modules, or both, is used to (Continued)

order a replenishment of the items held within the storage modules.

20 Claims, 59 Drawing Sheets

(51) Int. Cl.
    *G06T 7/70*     (2017.01)
    *G06T 7/73*     (2017.01)

(56) References Cited

U.S. PATENT DOCUMENTS

| | | |
|---|---|---|
| 11,100,741 B2 * | 8/2021 | Rahilly .................. G06F 21/32 |
| 11,361,278 B2 | 6/2022 | Dattamajumdar et al. |
| 2005/0103842 A1 | 5/2005 | Bong et al. |
| 2007/0208598 A1 | 9/2007 | McGrady et al. |
| 2010/0141457 A1 | 6/2010 | Wass et al. |
| 2016/0078704 A1 | 3/2016 | Phillips et al. |
| 2017/0316374 A1 | 11/2017 | Vahlberg et al. |
| 2018/0108197 A1 | 4/2018 | Phillips et al. |
| 2019/0308819 A1 | 10/2019 | Greyshock |
| 2019/0371458 A1 | 12/2019 | Gonzalez |

OTHER PUBLICATIONS

Application No. PCT/US2021/023730, International Search Report and Written Opinion dated Sep. 9, 2021, 15 pages.
PCT/US2021/023730, "Invitation to Pay Additional Fees and, Where Applicable, Protest Fee", dated May 25, 2021, 2 pages.
PCT/US2021/023730, International Preliminary Report on Patentability dated Oct. 13, 2022, 11 pages.
Application No. CA3,173,327 , Office Action, dated Sep. 29, 2023, 4 pages.
Application No. EP21781333.6 , Extended European Search Report, Mailed On Dec. 11, 2023, 8 pages.

* cited by examiner

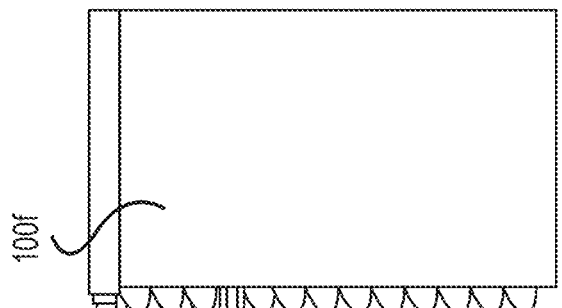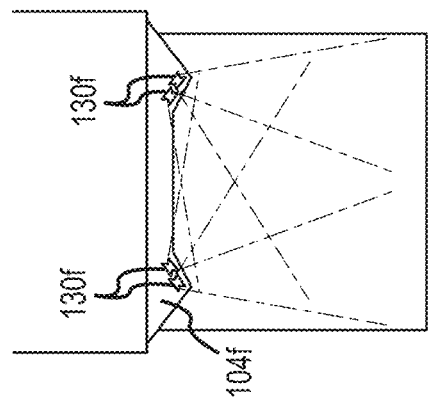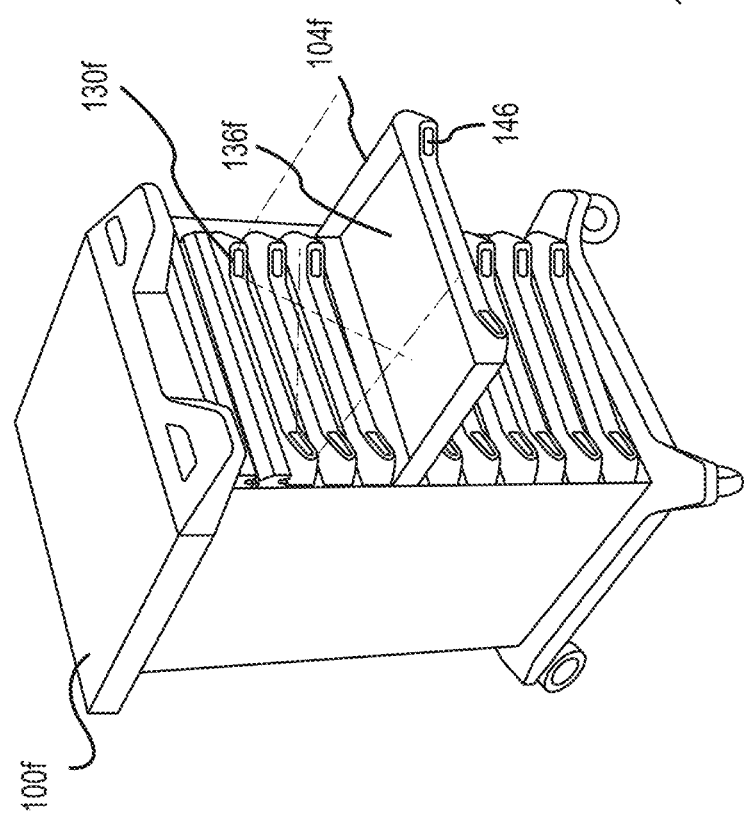

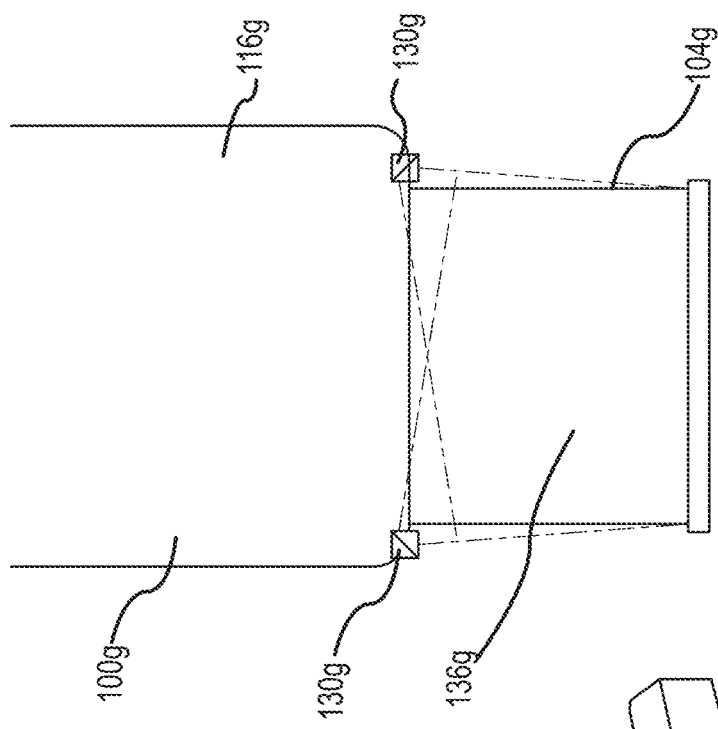
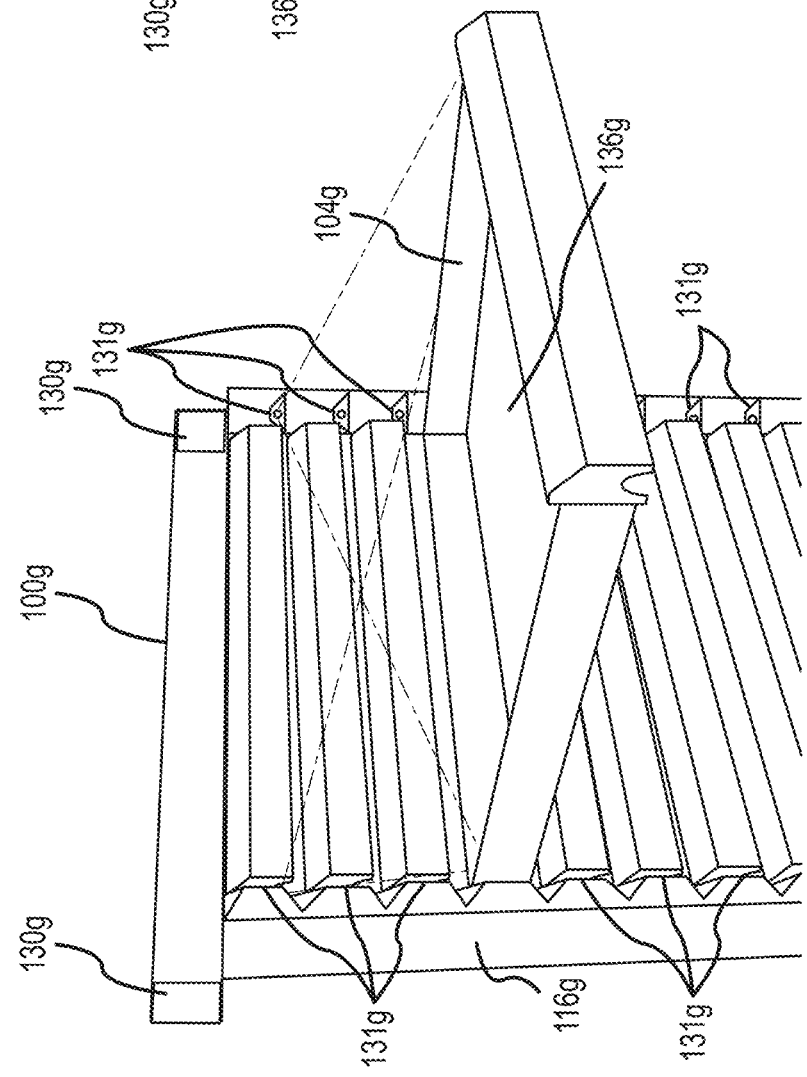
FIG.8B
FIG.8A

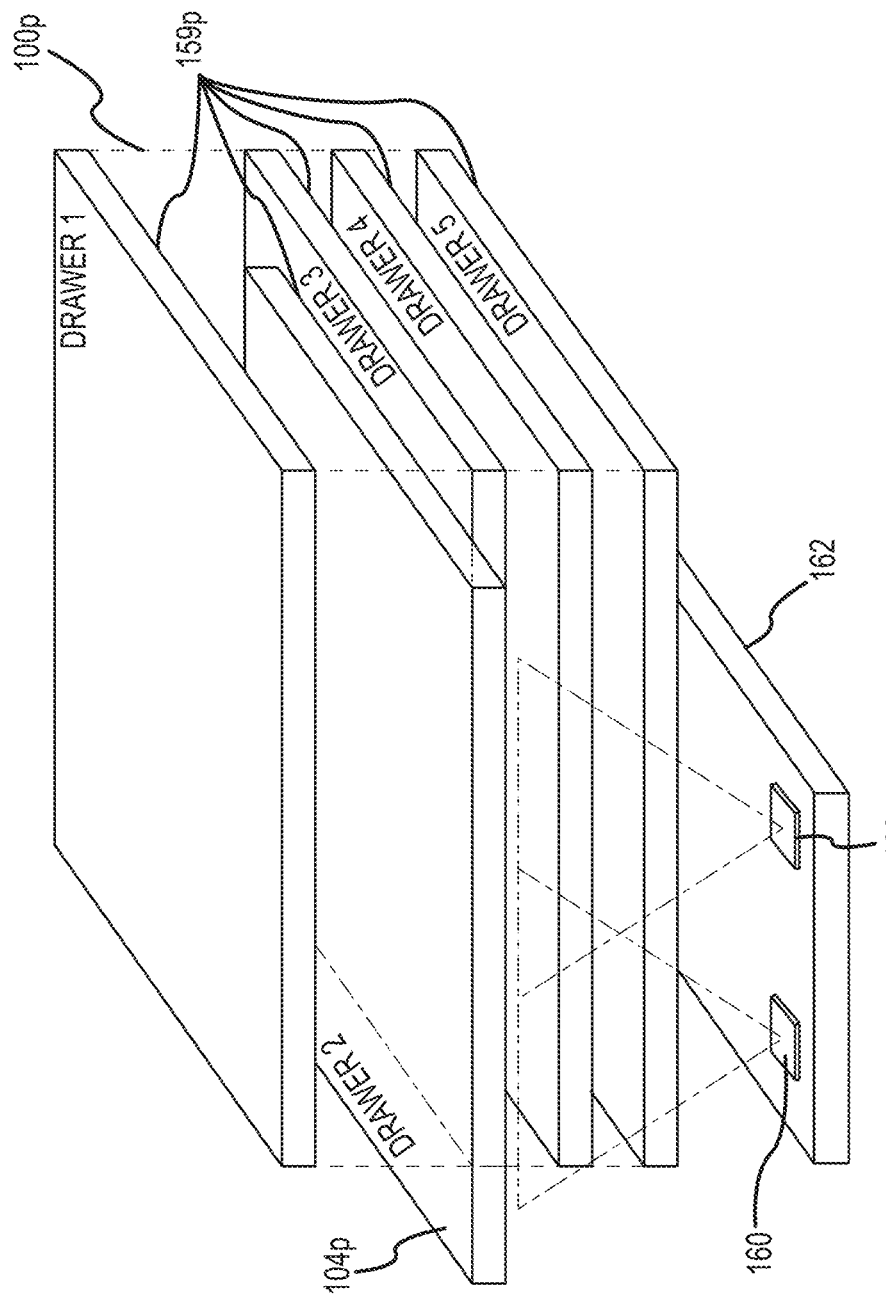

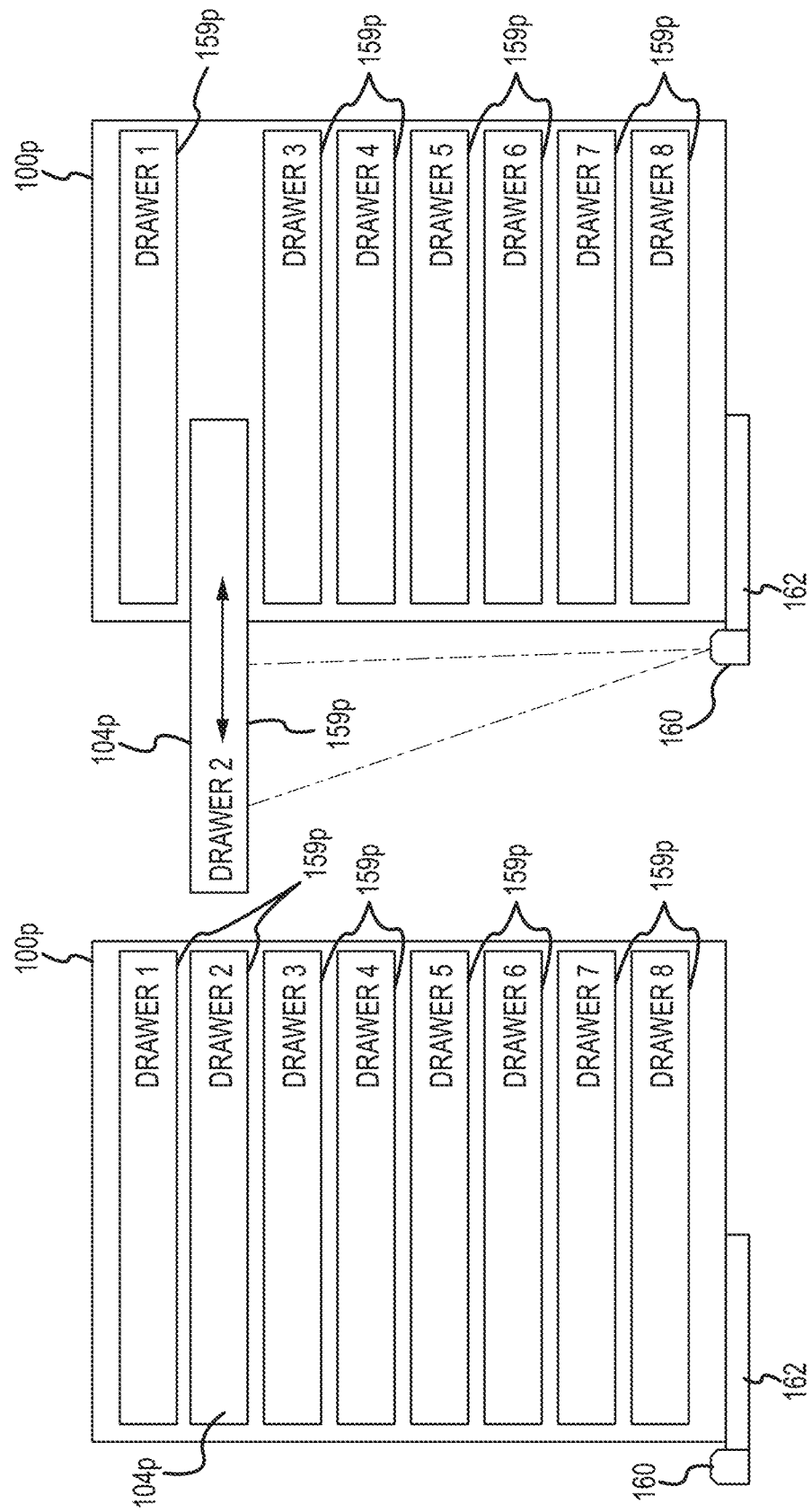

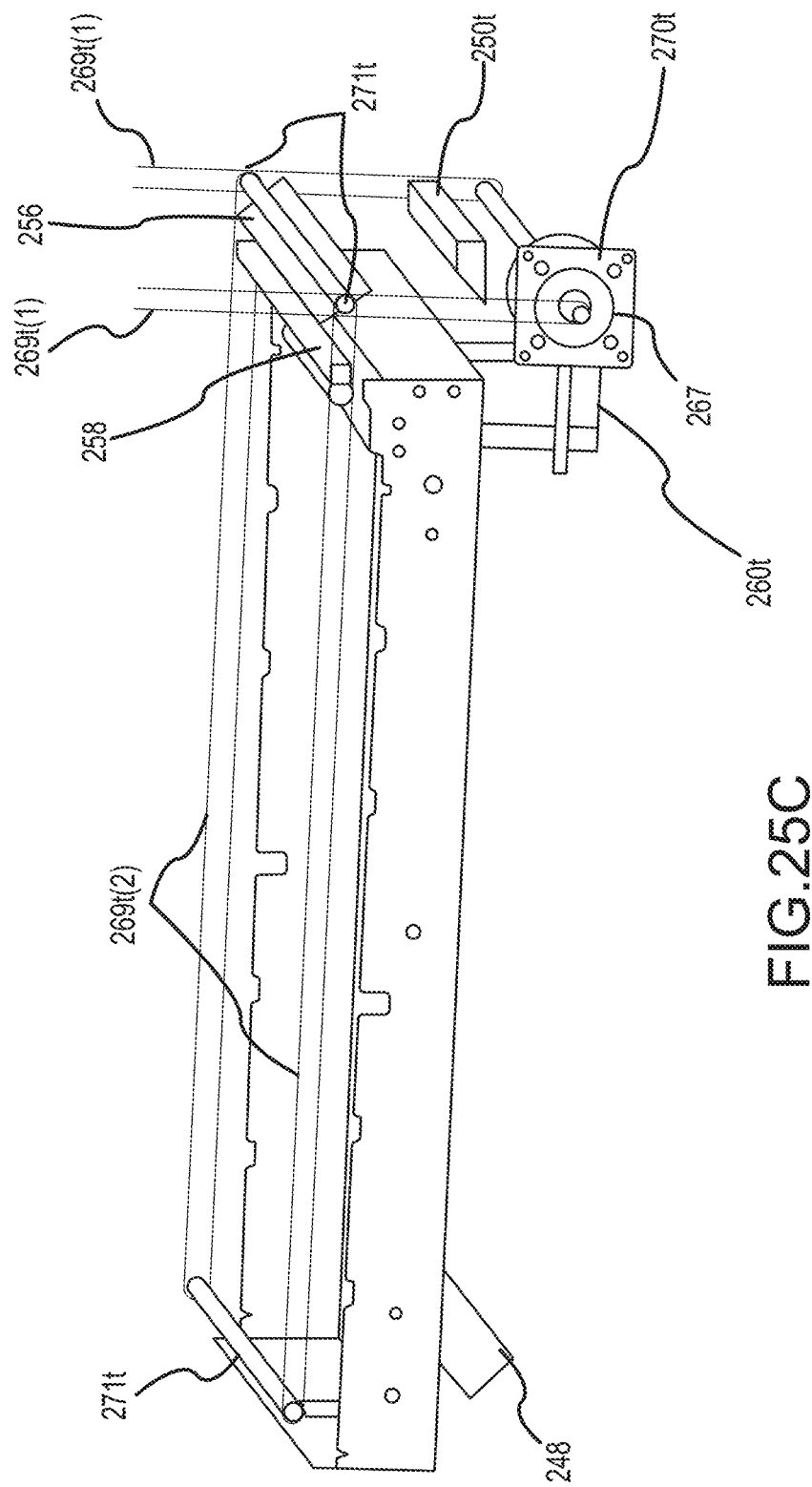

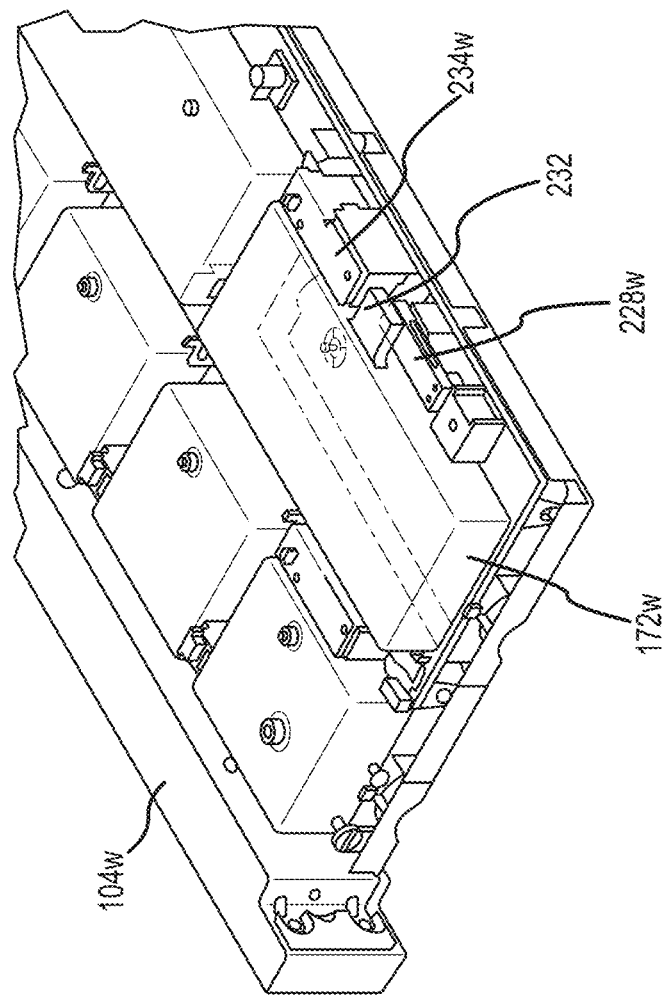

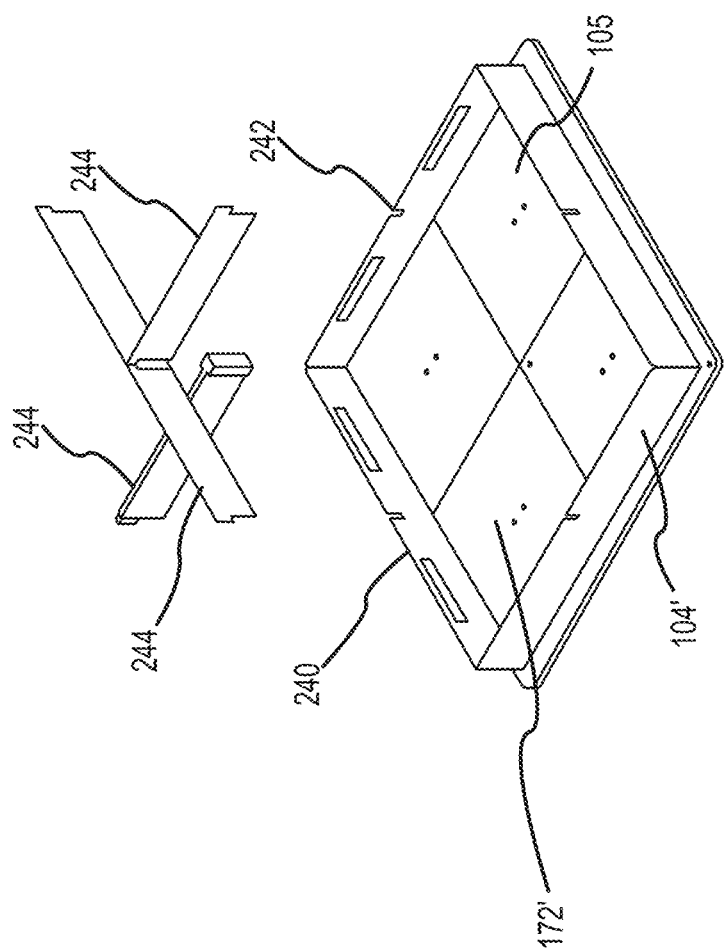

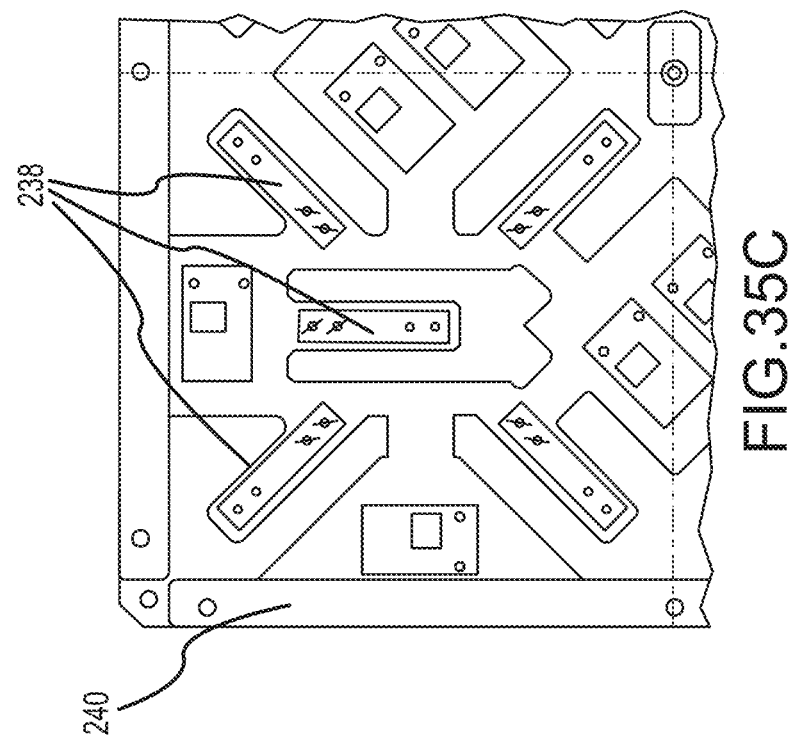
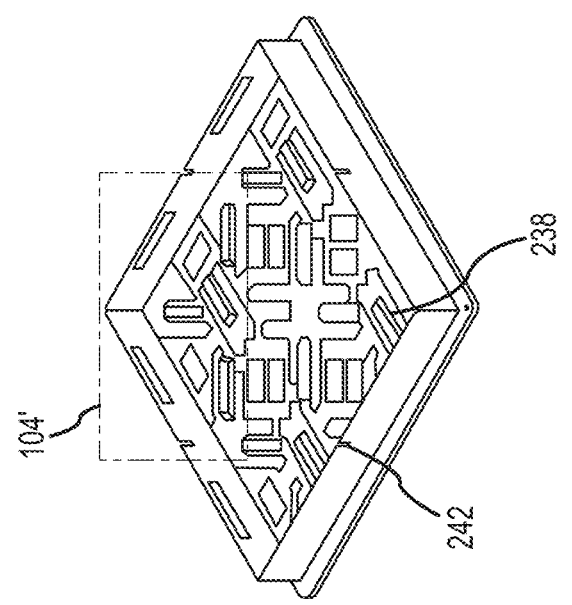
FIG.35C
FIG.35B

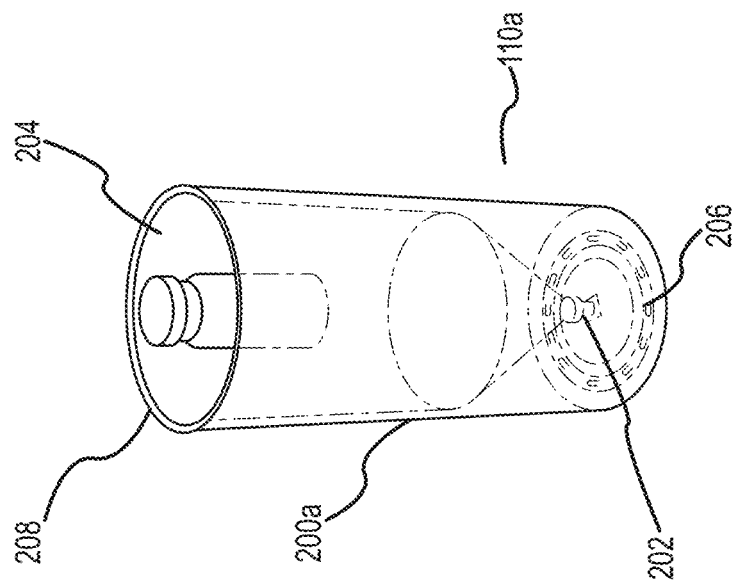
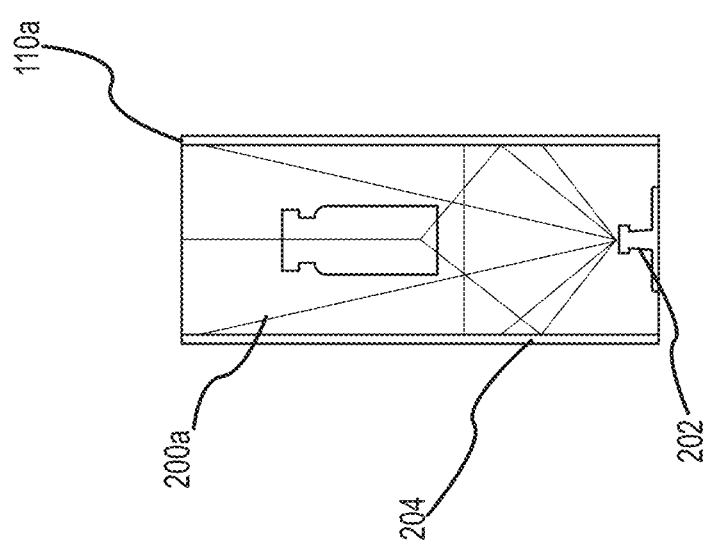
FIG. 36A
FIG. 36B

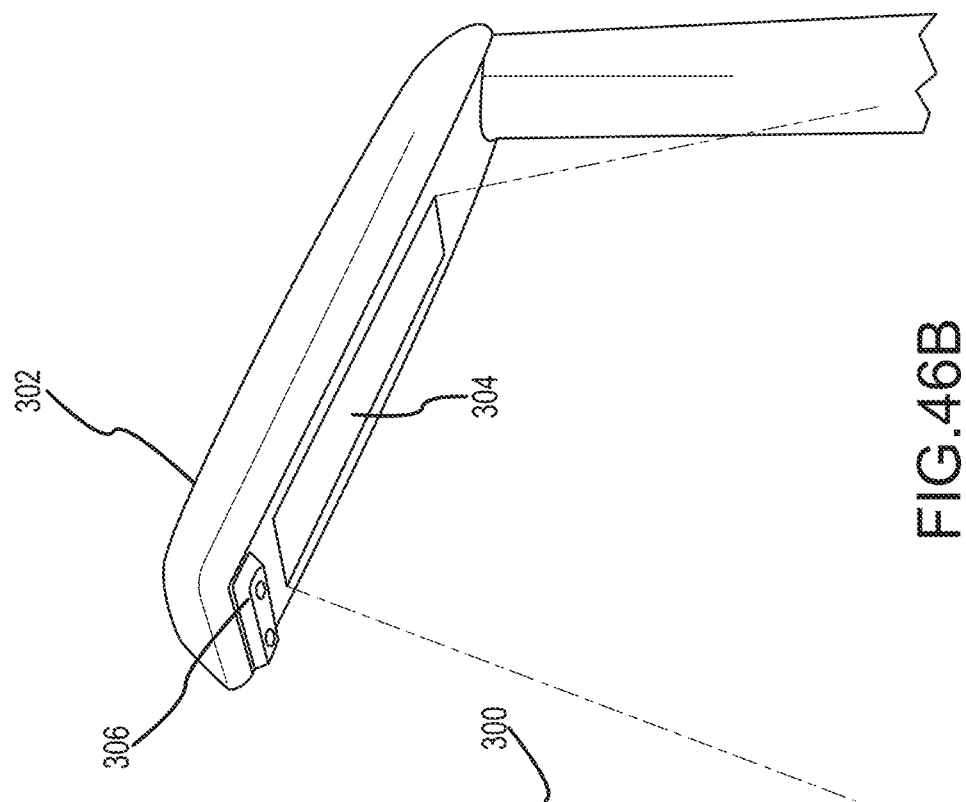
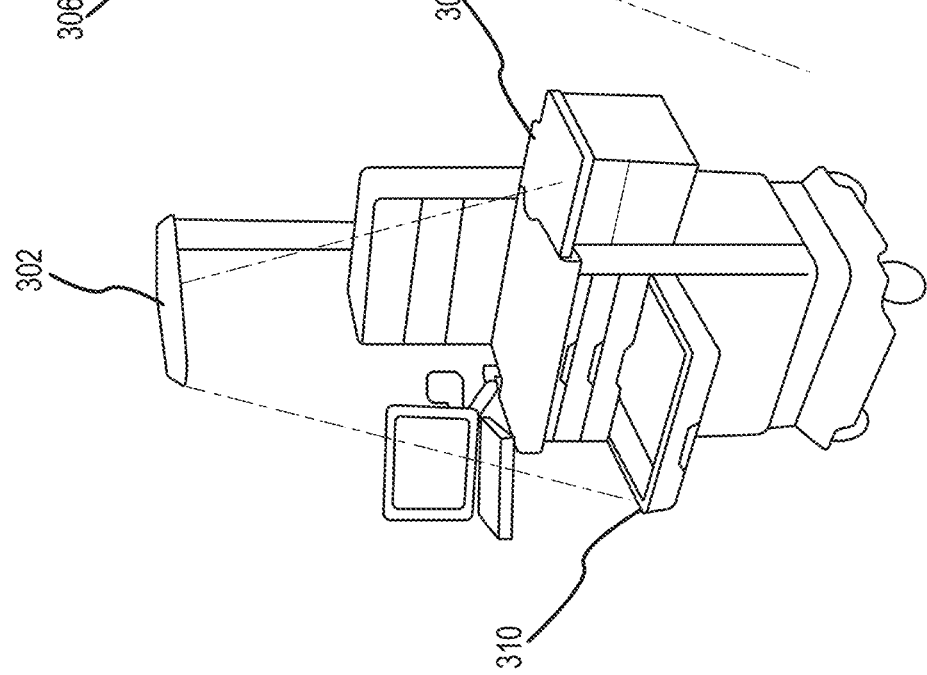

OPTICAL SENSING-BASED INVENTORY CONTROL SYSTEMS AND METHODS

CROSS-REFERENCE TO RELATED APPLICATIONS

This application is a continuation of U.S. application Ser. No. 16/836,912, filed on Mar. 31, 2020, entitled "OPTICAL-SENSING BASED INVENTORY CONTROL SYSTEMS AND METHODS", the disclosure of which is incorporated by reference herein in its entirety.

BACKGROUND OF THE INVENTION

Medical facilities have struggled with efficient ways to track inventories of items such as medical supplies and medications that are used in the treatment of patients. Current practices require medical personnel to record when items are removed from storage locations, such as by scanning a barcode, punching in an identifier, interacting with a graphical user interface on a computer, etc. This can be inconvenient for the medical personnel, as such procedures take up time and often lead to errors in handling and dispensing. Additionally, the tracking of used items (such as conventional sharps), returns of items into a return bin, and/or discards of items into waste bins can be challenging. Improvements in these areas and others are desired.

BRIEF SUMMARY OF THE INVENTION

Embodiments of the present invention are directed to systems and methods for tracking the usage and inventory of various items within a storage unit. Embodiments utilize various combinations of sensors to monitor the contents and usage of items from the storage unit. The sensors may work alone and/or in conjunction with one another to verify the identity and/or counts of the various items. In this way, verification and/or counting may take place with minimal involvement by the user. This not only increases the accuracy of the process, but also provides convenience to the user as less effort is required by the user. Additionally, embodiments provide techniques for updating inventory counts with a central computing system to enable real-time system-wide inventory counts to be generated. Such techniques improve item reordering and replenishment processes, as more accurate item counts are readily available.

In one embodiment, an inventory tracking system is provided. The inventory tracking system may include one or more storage modules. Each storage module may be adapted to hold one or more quantities of one or more items. Each of the items may be positioned at any of a plurality of locations within the storage modules independent of the physical characteristics of the items. The system may also include one or more inventory monitoring modules. Each inventory monitoring module may be adapted to monitor one or more of the storage modules for at least one act. Such acts may include, for example, adding an item into one or more of the storage modules, retrieving an item present in one or more of the storage modules, consuming of the item retrieved from one or more of the storage modules, returning an unused item to any of the storage modules, or discarding at least a portion of a consumed item. One or more inventory monitoring modules may also determine information about one or more of the items used in the act.

In some embodiments, one or more of the storage modules may be further adapted to update a central inventory database. The information that may be updated includes a location of one or more of the storage modules and/or a revised inventory of one or more of the items stored within one or more of the storage modules. In such embodiments, the location of one or more of the storage modules or the revised inventory of one or more of the items stored within the storage modules is used to order a replenishment of the items held within one or more of the storage modules. In some embodiments, one or more of the inventory monitoring modules may also monitor one or more of the storage modules for the at least one act using at least one sensor that detects a physical characteristic of each of the one or more items. In other embodiments, the system may further include an access control system adapted to determine that a user is an authorized user and to permit the authorized user to selectively access the one or more storage modules.

In certain embodiments, the information about one or more of the items is further used to determine inventory levels within the at least one or more of the storage modules. In other embodiments, the inventory tracking system further includes a communication interface that is configured to provide the inventory levels to one or more remote devices. In some embodiments, one or more of the remote devices may include a central storage system. In other embodiments, one or more of the remote devices may include a mobile device of a user. In some embodiments, the communication interface may be further configured to place a request for replenishment of inventory at any of the one or more storage modules.

In certain embodiments, the inventory control system may also include a return module adapted to receive unused items. In some embodiments, the return module may include one or more sensors to identify the unused item. In other embodiments, one or more of the sensors may be configured to identify the unused item visually, chemically, electronically, or by a combination of those techniques.

In some embodiments, the inventory control system may also include a waste bin. In certain embodiments, the waste bin may be adapted to receive at least a portion of the consumed item, the retrieved item, or both. In some embodiments, the waste bin may include one or more sensors to identify the portion of the consumed item or the retrieved item. In other embodiments, one or more of the sensors may be configured to identify the consumed item, the retrieved item, or both. This may be done visually, chemically, electronically, or by a combination of those techniques.

In some embodiments, the inventory control system may include a work platform proximate to the storage module. The work platform may be adapted to provide space for preparation of an item. In some embodiments, the work platform may include one or more sensors adapted to identify at least one item placed on the work platform. One or more of the sensors may be configured to identify the at least one item visually, chemically, electronically, or by a combination of those techniques. In some embodiments, the item may be an item prepared on the work platform.

In another embodiment, a method of tracking inventory is provided. The method may include performing at least one act selected from the following: adding one or more items into one or more storage modules, removing one or more items from one or more of the storage modules, consuming one or more items retrieved from one or more of the storage modules, returning one or more items to any of the one or more storage modules, and discarding a portion of contents of one or more of the items. Each of the one or more items may be positioned at any of a plurality of locations within one or more of the storage modules independent of physical characteristics of the one or more items. The method may further include determining each of the acts that were performed, identifying one or more of the items used in the act, and recording information about the act, the items used in the act, or both.

In some embodiments, the method may further include updating a central inventory database with information such as a location of one or more of the storage modules or a revised inventory of one or more of the items stored within one or more of the storage modules. At least one of the locations of the one or more storage modules or the revised inventory of the one or more items stored within the one or more storage modules may be used to order a replenishment of the one or more items held within the one or more storage modules. In some embodiments, the method may also include transmitting the information about the act, the items used in the act, or both, to a database. The method may also include determining inventory levels in one or more of the storage modules based on the transmitted information. In some embodiments, the method may further include replenishing the stock within the one or more storage modules based on the determined inventory levels. In some embodiments, determining each of the acts that were performed and/or identifying the items used in the act may be based on sensor data from one or more of an imaging sensor, a load sensor, a radio frequency sensor, and an infrared sensor.

In another embodiment, an inventory control system is provided. The system may include a housing defining an interior and a drawer that may be positioned within the interior and that is moveable between a closed position and an open position. The drawer may include lateral side walls positioned on either side of a storage region. The system may also include an imaging device coupled with one of the lateral sidewalls and directed toward the storage region of the drawer. The system may further include at least one processor that is configured to analyze one or more images taken from the imaging device to identify items present within the storage region and determine an inventory of the items present within the storage region. In some embodiments, the imaging device may be activated upon the drawer being at least partially opened. In other embodiments, the system may also include an additional imaging device positioned on the other lateral side wall.

In some embodiments, each lateral side wall may include a vertically-extending wing that protrudes above a top level of the storage region. The imaging device may be mounted on one of the vertically extending wings at a position proximate a top of the vertically-extending wing such that the imaging device is elevated relative to the storage region. In some embodiments, the system may also include an additional drawer positioned above the drawer. When both the drawer and the additional drawer are in the closed position, a storage region of the additional drawer may be positioned between the vertically-extending wings of the drawer.

In some embodiments, the system may further include a pivoting arm that is coupled with one of the lateral sidewalls. The imaging device may be positioned proximate an end of the pivoting arm. The pivoting arm may be configured to move between a storage position in which the pivoting arm is at least substantially parallel to a sliding axis of the drawer and an imaging position in which the pivoting arm is at least substantially perpendicular to the sliding axis of the drawer to elevate the imaging device relative to the storage region. The pivoting arm may be configured to be in the storage position when the drawer is in the closed position and in the imaging position when the drawer is in the open position. In some embodiments, the pivoting arm may be spring biased toward the imaging position.

In another embodiment, a method of determining inventory is provided. The method may include capturing, using an imaging device of an inventory control system, one or more images of a storage region of a drawer of the inventory control system, analyzing the one or more images taken from the imaging device to identify items present within the storage region, and determining an inventory of the items present within the storage region. In some embodiments, the imaging device may be activated upon the drawer being at least partially opened. In other embodiments, the drawer may include an additional imaging device positioned on the other lateral side wall.

In certain embodiments, the drawer may include opposing lateral side walls that each comprise a vertically-extending wing that protrudes above a top level of the storage region. The imaging device may be mounted on one of the vertically extending wings at a position proximate a top of the vertically-extending wing such that the imaging device is elevated relative to the storage region. In some embodiments, the inventory control system may include an additional drawer positioned above the drawer. When both the drawer and the additional drawer are in the closed position, a storage region of the additional drawer may be positioned between the vertically-extending wings of the drawer.

In some embodiments, the drawer may include opposing lateral side walls that each comprise a pivoting arm. The imaging device may be positioned proximate an end of the pivoting arm. In some embodiments, the method further comprises moving the pivoting arm from a storage position in which the pivoting arm is at least substantially parallel to a sliding axis of the drawer to an imaging position in which the pivoting arm is at least substantially perpendicular to the sliding axis of the drawer to elevate the imaging device relative to the storage region as the drawer is opened and moving the pivoting arm from the imaging position to the storage position as the drawer is closed. In some embodiments, the pivoting arm may be spring biased toward the imaging position.

In another embodiment, an inventory control system includes a housing defining an interior and a drawer that may be positioned within the interior and that is moveable between a closed position and an open position. The drawer may define a storage region that includes a number of partitions. The system may include one or more imaging devices coupled with the housing at a position that is above the interior. Each of the one or more imaging devices may be directed downward such that a field of view of the one or more imaging devices covers at least a portion of a space that is occupied by the drawer when the drawer is in the open position. The system may also include at least one processor that is configured to receive one or more images from the one or more imaging devices, perform object detection on the one or more images to identify regions of interest of the one or more images that include an entire one of the number of partitions of the drawer, analyze the regions of interest to identify items present within the storage region, and determine an inventory of the items present within the storage region.

In some embodiments, the housing may further include a protrusion that extends outward from the housing such that at least a portion of the protrusion is positioned above the space that is occupied by the drawer when the drawer is in the open position. The imaging device may be coupled with a bottom surface of the protrusion. In some embodiments, the protrusion may be movable between a stowed position and an extended position in which the portion of the protrusion is positioned above the space that is occupied by the drawer when the drawer is in the open position. In some embodiments, the imaging device may be positioned on a front face of the housing. In other embodiments, the system may further include at least one additional imaging device mounted to the housing. In certain embodiments the system may also include an additional drawer positioned below the drawer and an additional imaging device that is positioned on a front surface of the drawer. The additional imaging device may be directed downward such that a field of view of the additional imaging device covers at least a portion of a space that is occupied by the additional drawer when the additional drawer is in an open position.

In another embodiment, an inventory control system includes a housing defining an interior and a drawer that may be positioned within the interior and that is moveable between a closed position and an open position. The drawer may define a storage region. The system may also include a lid coupled with the drawer. The lid may be movable between a closed state in which the lid covers the storage region and an open state in which the storage region is accessible. The system may include an imaging device coupled with a bottom surface of the lid. The imaging device may be angled such that when the lid is in the open state, the imaging device is directed at the storage region. The system may further include at least one processor that is configured to analyze one or more images taken from the imaging device to identify items present within the storage region and determine an inventory of the items present within the storage region. In some embodiments, the lid may be spring biased toward the open state. In other embodiments, when in the open state, the lid is at an angle between about 30 and 60 degrees relative to the drawer. In certain embodiments, when in the open state, the lid is at a substantially perpendicular angle relative to the drawer.

In another embodiment, an inventory control system includes a housing defining an interior and a drawer that may be positioned within the interior and that is moveable between a closed position and an open position. The drawer may define a storage region having a transparent base. The system further includes an imaging device positioned below the drawer. The imaging device may be directed upward such that a field of view of the imaging device covers at least a portion of a space that is occupied by the drawer when the drawer is in the open position. The system also includes at least one processor that is configured to analyze one or more images taken from the imaging device to identify items present within the storage region and determine an inventory of the items present within the storage region. In some embodiments, the imaging device may be positioned on a protrusion that extends forward from the housing.

In another embodiment, an inventory control system may include a housing defining an interior and a plurality of drawers that are positionable within the interior. Each drawer may be moveable between a closed position and an open position and may define a storage region. The system includes one or more imaging devices. At least one imaging device may be positioned above each of the plurality of drawers and may be directed downward. The at least one imaging device may be configured to image the storage region of a next drawer down. The system includes at least one processor that is configured to analyze one or more images taken from the one or more imaging devices to identify items present within the storage region of at least one of the plurality of drawers and determine an inventory of the items present within the storage region of the at least one of the plurality of drawers.

In some embodiments, the one or more imaging devices may include line scanners. In some embodiments, the system may include an additional plurality of imaging devices. At least one imaging device of the additional plurality of imaging devices may be positioned below each of the plurality of drawers and is directed downward. The at least one imaging device of the additional plurality of imaging devices may be configured to image the storage region of a next drawer down as the next drawer down is opened, closed, or both opened and closed. In some embodiments, at least some of the one or more imaging devices may be coupled with a base of one of the plurality of drawers. In some embodiments, the at least one imaging device may be configured to image the storage region of the next drawer down as the next drawer down is being opened, closed, or both opened and closed. In some embodiments, the at least one imaging device may be configured to image the storage region of the next drawer down when the next drawer down is in the closed position. In some embodiments, the one or more imaging devices may be translatable along one or more axes to image different portions of the storage region.

In another embodiment, an inventory control system includes a housing defining an interior and a plurality of drawers that are positionable within the interior. Each drawer may be moveable between a closed position and an open position and may define a storage region. The system includes a plurality of imaging devices. At least one imaging device may be positioned on a front surface of each of the plurality of drawers and is directed downward. The at least one imaging device may be configured to image the storage region of a next drawer down when the next drawer down is in the open position. The system includes at least one processor that is configured to analyze one or more images taken from the plurality of imaging devices to identify items present within the storage region of at least one of the plurality of drawers and determine an inventory of the items present within the storage region of the at least one of the plurality of drawers.

In another embodiment, an inventory control system includes a housing defining an interior and a drawer that is positionable within the interior and that is moveable between a closed position and an open position. The drawer may define a storage region. The system includes one or more imaging devices positioned within the housing and configured to image at least a portion of the storage region of the drawer. The system includes one or more mirrors that are positioned within the housing. The one or more imaging devices may be directed toward the one or more mirrors. At least one of the one or more mirrors may be movable to adjust an image position of the imaging device within the storage region. The system includes at least one processor that is configured to analyze one or more images taken from the imaging device to identify items present within the portion of the storage region and determine an inventory of the items present within the portion of the storage region.

In some embodiments, at least one of the imaging devices may be translatable along one or more axes to image different portions of the storage region. In some embodiments, the system may further include a light element that is configured to illuminate a portion of the storage region when the drawer is in the closed position. The imaging device may be configured to image the storage region when the drawer is in the closed position.

In another embodiment, an inventory control system includes a housing defining an interior and a drawer that is positionable within the interior. The drawer may be moveable between a closed position and an open position and may define a storage region. The system includes at least one load sensor positioned on a base of the drawer. The at least one load sensor may be configured to detect the presence of one or more items within at least a portion of the storage region of the drawer based on a detected change in load measurement. The system includes at least one processor that is configured to receive a load measurement from the at least one load sensor and determine an inventory of the one or more items present within the portion of the storage region based at least in part on the load measurement.

In some embodiments, the at least one load sensor may include a strain gauge. In other embodiments, the at least one load sensor may include a capacitive sensor. In certain embodiments, the capacitive sensor may include two metal plates that are separated by an inert material. In some embodiments, the portion of the storage region may include a partitioned area of the storage region. In other embodiments, the partitioned area of the storage region may include a removable bin. In some embodiments, the at least one load sensor may include an array of load sensors positioned about a base of the storage region.

In another embodiment, an inventory control system includes a housing defining an interior and a drawer that may be positioned within the interior. The drawer may be moveable between a closed position and an open position and may define a storage region. The system includes a bin disposed within the drawer. The bin includes a bin body defining a storage area, a lid that is coupled with the bin body and that is moveable between a closed state in which the lid covers the storage area and an open state in which the storage area is accessible, an electronically-actuated locking mechanism that is configured to lock and unlock the lid, and an imaging device positioned on an underside of the lid. The imaging device may be configured to image an interior of the storage area. The system includes at least one processor that is configured to analyze one or more images taken from the imaging device to identify items present within the storage area and determine an inventory of the items present within the storage area.

In some embodiments, the imaging device may be configured to image the interior of the storage area when the lid is in the open state. In other embodiments, the bin may further include a lighting element. The imaging device may be configured to image the interior of the storage area when the lid is in the closed state. In yet other embodiments, the bin further includes a load sensor coupled with a base of the storage area. The load sensor may be configured to detect the presence of one or more items within the storage area of the bin.

In another embodiment, an inventory control system includes a housing defining an interior and a drawer that is positionable within the interior. The drawer may be moveable between a closed position and an open position and may define a storage region. The system includes a radio frequency (RF) reader having an RF antenna that is coupled with the drawer. The RF antenna may be configured to detect the presence of one or more RF-tagged items within at least a portion of the storage region of the drawer. The system includes at least one processor that is configured to receive information from the RF reader related to the one or more RF-tagged items and determine an inventory of the one or more RF-tagged items based on the information. In some embodiments, the system may include RF shielding on one or both of a top and a bottom of the drawer.

In another embodiment, an inventory control system includes a housing having a storage area. The housing includes a work surface that includes one or more sensors that are configured to monitor use of one or more items taken from the storage area. The one or more sensors may be selected from the group consisting of a load sensor, an imaging device, a radio frequency reader, and an optical reader. The system includes at least one processor that is configured to receive information from the one or more sensors and determine an inventory of the one or more items based on the information.

In some embodiments, the load sensor is positioned beneath at least a portion of the work surface. In other embodiments, the imaging device may be positioned above the work surface. In yet other embodiments, the work surface may include a transparent portion. The imaging device may be positioned beneath the transparent portion. In some embodiments, the optical reader may include an omnidirectional reader. In other embodiments, the omnidirectional reader may be provided within a recess formed in a top of the work surface. In certain embodiments, the system may also include one or more of a waste bin, a sharps bin, and a return bin. In some embodiments, the system may also include a label printer. The label printer may be automatically triggered based on the one or more sensors detecting a particular item.

In another embodiment, an inventory control system includes a housing defining an interior, at least one drawer positioned within the interior, and at least two different types of sensors that are configured to monitor an inventory of one or more items stored within the at least one drawer. The system further includes a processor that is configured to generate inventory counts of each of the one or more items stored within the at least one drawer based on data from a first type of sensor and a second type of sensor of the at least two different types of sensors, compare the inventory counts from the first type of sensor and the second type of sensor, and determine an inventory of each of the one or more items based on the comparison. In some embodiments, the one or more sensors are selected from the group consisting of a load sensor, an imaging device, and a radio frequency reader.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label. Additionally, where similar components include the same first reference label, the similar components may have similar structure and operation except where explicitly stated otherwise.

FIG. 7A illustrates a perspective view of an inventory control system having imaging devices mounted on an exterior of the drawers according to embodiments of the present invention.

FIG. 7B illustrates a side elevation view of the inventory control system of FIG. 7A.

FIG. 7C illustrates a top view of the inventory control system of FIG. 7A.

FIG. 8A illustrates a perspective view of an inventory control system having imaging devices coupled with a top of a housing according to embodiments of the present invention.

FIG. 8B illustrates a top view of the inventory control system of FIG. 8A.

FIG. 16A illustrates an inventory control system having an underside imaging system according to embodiments of the present invention.

FIG. 16B illustrates a side elevation view of the inventory control system of FIG. 16A with the drawers in a closed position.

FIG. 16C illustrates a side elevation view of the inventory control system of FIG. 16A with one of the drawers in an open position.

FIG. 25C illustrates a perspective view of a drawer and motor assembly of the inventory control system of FIG. 25A.

FIG. 29B illustrates a perspective view of the bin of FIG. 29A.

FIG. 35A illustrates an open-topped bin according to embodiments of the present invention.

FIG. 35B illustrates the open-topped bin of FIG. 35A having one or more load sensors.

FIG. 35C illustrates the open-topped bin of FIG. 35A having one or more load sensors.

FIG. 36A illustrates a perspective view of an omnidirectional reader having a central imaging device according to embodiments of the present invention.

FIG. 36B illustrates a side elevation view of the omnidirectional reader of FIG. 36A.

FIG. 46A illustrates a mobile storage module having an overhead imaging unit according to embodiments of the present invention.

FIG. 46B illustrates the overhead imaging unit of FIG. 46A.

DETAILED DESCRIPTION OF THE INVENTION

Figure 1A:
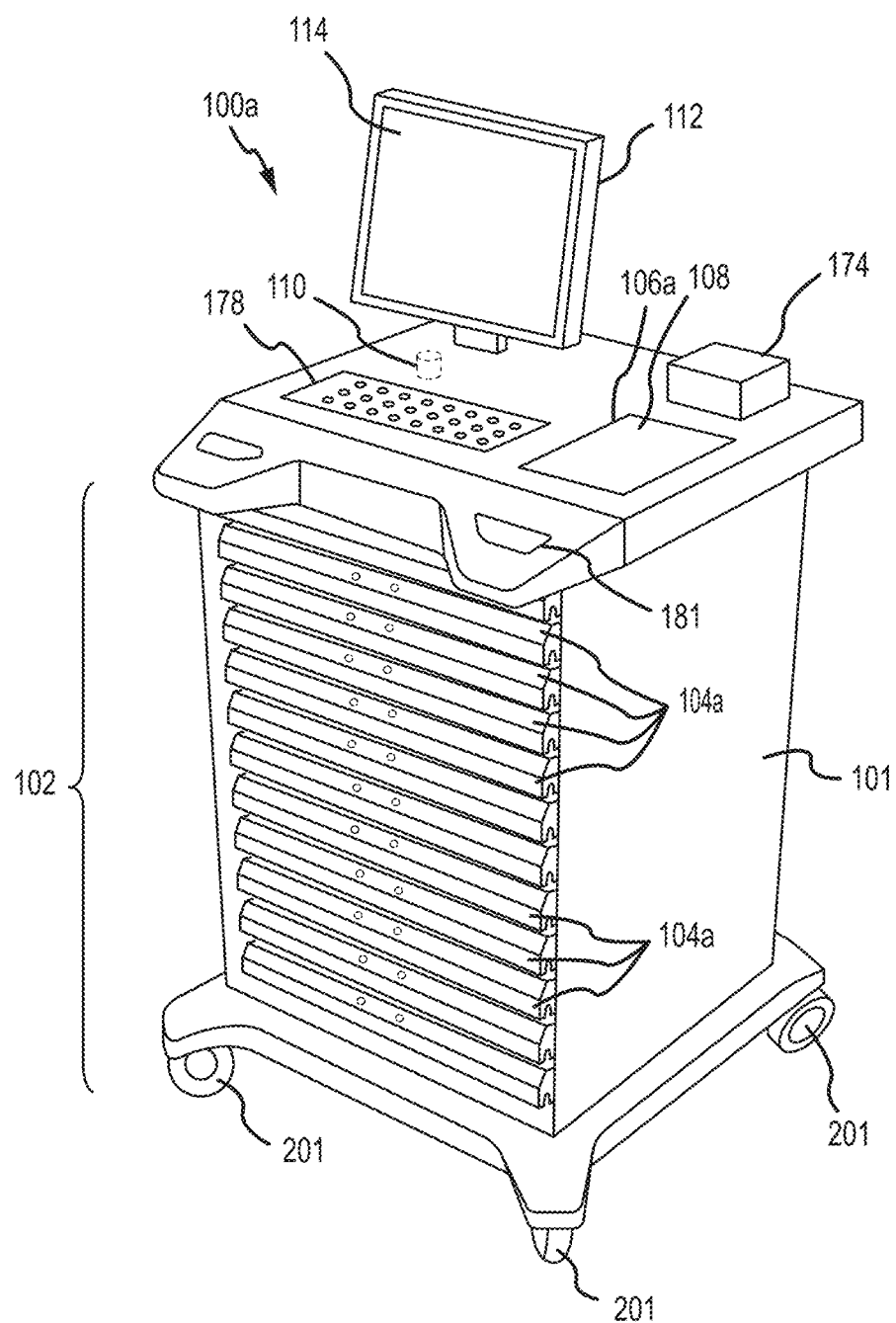
FIG. 1A illustrates an embodiment of an inventory control system according to embodiments of the present invention.

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It will be understood that various changes may be made in the function and arrangement of elements without departing from the spirit and scope of the invention as set forth in the appended claims. Merely by way of example, any embodiment described herein may or may not have any of the features discussed therewith, and may or may not have any feature discussed with respect to other embodiments.

Embodiments of the present invention are directed to inventory control systems and methods. Embodiments may be particularly useful in tracking the inventory and usage of individual items, such as those used in the healthcare environment, including medical supply items, pharmaceuticals, and the like. The inventory control systems and methods described herein provide greater ease of use and improved accuracy of inventory counts relative to existing systems. To achieve these results, the inventory control systems and methods may leverage multiple types of sensors and/or storage areas. While described primarily in relation to medical devices, medications, and/or other medical items, it will be appreciated that the inventory control systems described herein may be implemented with any other item, such as tools, instruments, consumable products, and the like.

In some embodiments, the inventory control systems may be integrated into medical storage units. These medical storage units may store and dispense or otherwise provide access to medical supplies, instruments, medications, and/or other medical items. For example, medical storage units are often utilized by nurses, physicians, and other medication personnel to prepare for and/or conduct a procedure. In medical scenarios, the inventory control systems not only track the quantity of items present, but also track the usage of such items by requiring a registered user to log what items are to be removed and assign the items to a particular patient and/or procedure.

In operation, the inventory control systems described herein typically involve several processes that allow the items stored therein to be accurately counted and dispensed. For example, in medical applications, the inventory control systems may be utilized to 1) identify a user who is interacting with the system, 2) identify a patient associated with the item (or multiple items) being dispensed, 3) identify a task or other procedure with which the item is to be used, 4) dispense the item, 5) and track which items have actually been taken from the inventory control system. By completing each of these processes, the inventory control system is able to track not only what items have been dispensed, but also which personnel received the items and for what purpose (e.g., for which patient/procedure). By associating the dispensed items with individuals, the inventory control systems may help with the identification of improper usage of items, including diversion, improper usage/wasting, etc., and may associate such behavior with a particular user.

Figure 1B:
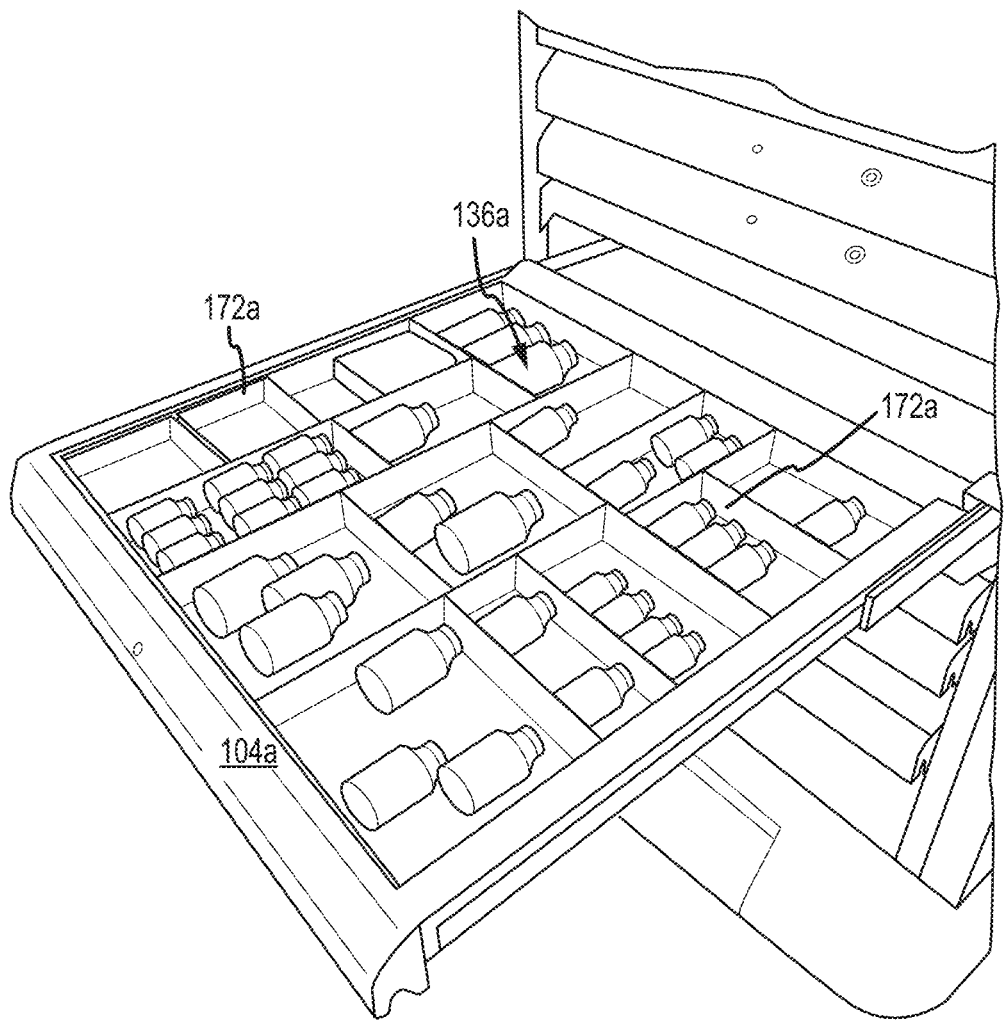
FIG. 1B illustrates an open drawer of the inventory control system of FIG. 1A.

Turning now to FIG. 1A, one embodiment of an inventory control system 100a is illustrated. Inventory control system 100a includes cabinet 101 that defines a storage area 102 that is used to store any number of items, such as tools, vials, ampoules, ointments, tablets, syringes, instruments, paints, medications, and the like. As illustrated, the storage area 102 includes a number of drawers 104a. However, other storage areas such as shelves, racks, carts, and the like are possible in some embodiments. Optionally, the cabinet 101 may include wheels 201. The cabinet 101 defines an open interior that receives drawers 104a. Drawers 104a may be of different sizes and shapes to accommodate items of various sizes and/or shapes and/or to accommodate various equipment, such as sensors, security features, climate control equipment, and the like. As illustrated, different sizes of drawers 104a may be included in a single inventory control system 100a. In other embodiments, an inventory control system 100a may include drawers of uniform sizes. As illustrated in FIG. 1B, one of drawers 104a may include a storage region 136a that is configured to receive a number of items, such as the items described above. As illustrated, the storage region 136a is divided into a number of bins 172a or other partitions. These bins 172a may be open topped (as shown) and/or have lockable lids (not currently shown). In some embodiments, the bins 172a may be removable containers, while in other embodiments the bins 172a may be formed by arranging partition members atop a bottom surface of the drawer 104a. It will be appreciated that other variations and/or arrangements of the bins 172a are possible. In one instance, the geometry of the bins 172a may be fixed while in other instances the geometry of the bins 172a may be configurable. Some embodiments may forego the use of bins 172a and may include an open interior within the storage region 136a.

Returning back to FIG. 1A, drawers 104a may be under the control of computing device 112 and/or another controller (that may be physically detached from the inventory control system 100a but communicatively connected with the inventory control system 100a). In some embodiments, each of drawers 104a may include an electronically controllable locking mechanism (not shown), and may only be openable under the control of computing device 112. In some embodiments, the environment within some or all of the drawers 104a may be controlled for desired levels of temperature and/or humidity.

The computing device 112 may perform or enable the performance of certain functions within the inventory control system 100a. For example, the computing device 112 may allow an authorized user to access the inventory control system 100a and any of the contents stored within any of the drawers 104a. In another example, the computing device 112 may store inventory information about the quantity of one or more items stored within any or all of the drawers 104a. In another example, the computing device 112 may be communicatively linked with a central inventory system (not shown) to provide visibility of the inventory held within the inventory control system 100a. Such information is meant to allow a central warehouse, for example, to view the contents of each of the inventory control systems 100a and determine when and what quantities of specific items to replenish and avoid a situation where the inventory level (within the inventory control system 100a and/or a medical facility) drops below minimum requirements.

Figure 2:
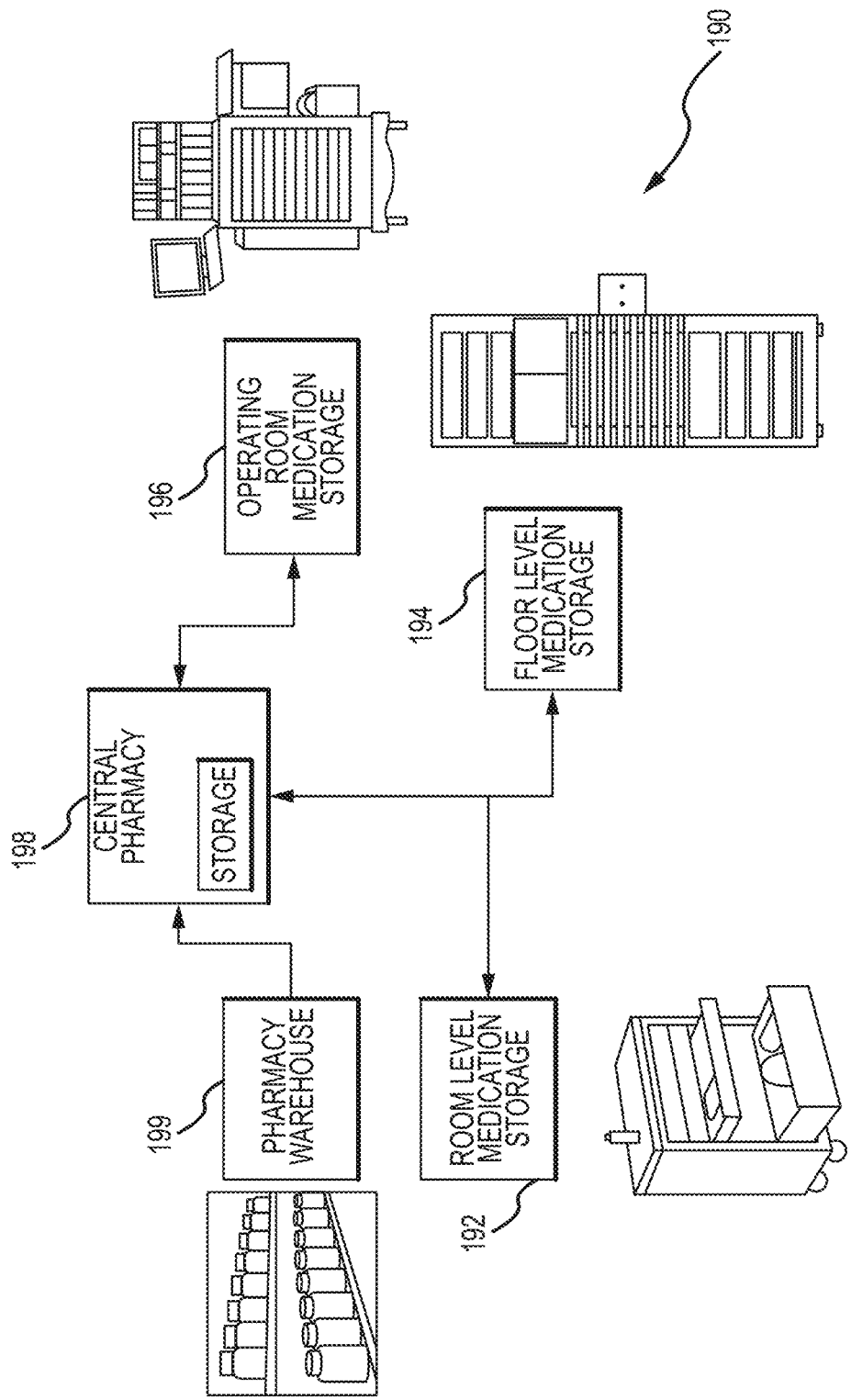
FIG. 2 illustrates a system diagram of an inventory control system in a medical facility application according to embodiments of the present invention.

FIG. 2 illustrates a hospital system 190 that may include a number of inventory control systems (such as inventory control system 100a as shown in FIG. 1A). In some embodiments, one or more of the inventory control systems are implemented in the form of a room level medication storage unit 192, a floor level medication storage unit 194, and/or an operating room medication storage unit 196, each positioned at a particular room, ward, and/or floor within the hospital. In this application, each storage unit 192, 194, 196 may be in communication with a computing device of a central pharmacy 198 of the hospital over a network, such that each storage unit 192, 194, 196 may provide information about the inventory to the central pharmacy 198. As a result of the visibility of the inventory, the central pharmacy 198 may determine what medications or supply items need to be replenished in the storage units 192, 194, 196 so that the doctors and nurses can continue to deliver the proper levels of care and treatment. The central pharmacy 198 may be in communication with a pharmacy warehouse computer 199 and/or database in order to monitor the inventory of medications and/or other supplies on hand for reordering purposes. In another example, the storage units 192, 194, 196 may keep track of information about what medications or supply items were removed or restocked, when such action was performed, and also by whom. Such information provides additional levels of accountability and tracking. In yet another example, the storage units 192, 194, 196 may record information such as the patient for whom medication was retrieved and/or dispensed. In a further example, the storage units 192, 194, 196 may also have the ability to warn if an improper medication (wrong type, wrong medication, wrong quantity, and the like) was retrieved for a patient. In yet a further example, the storage units 192, 194, 196 may have the ability to warn the user (such as a nurse or other medical personnel) about possible drug interactions based on patient specific information such as drug allergies or adverse drug interactions due to drugs taken for pre-existing conditions. It is also envisioned that storage units 192, 194, 196 may benefit from having access to capabilities such as artificial intelligence/machine learning to provide such insights with a greater accuracy and speed. It will be appreciated by those skilled in the art that such capabilities require access to patient information, doctor prescription information, and perhaps even access to the patient's health record in electronic or non-electronic forms. Similar techniques for providing inventory information to a central computing system that may be used are described in U.S. patent application Ser. No. 16/834,950, filed Mar. 30, 2020 and titled SENSOR DRIVEN SECURE DISPENSING UNIT, the entire contents of which are herein incorporated by reference.

Returning to FIG. 1A (and applying the principles of the embodiment of FIG. 2 to the inventory control system 100*a* of FIG. 1A), computing device 112 may store information about what supplies are stored in which compartments of inventory control system 100*a*. In one typical basic medical usage scenario, a user may enter, using an input device of the computing device, an identification of a patient who is under the care of the user, and who will need medication during the user's current rounds. Computing device 112 may access the patient's medical file and determine what medications have been prescribed for that patient. Computing device 112 may then open only the drawer 104*a* or drawers 104*a* containing the prescribed medications for the patient. In some embodiments, one or more lighted indicators may direct the user to a correct drawer 104*a*. A particular compartment within the correct drawer 104*a* may be highlighted, for example, with a lighted indicator, to draw the user to the correct medication. The user can then remove the patient's prescribed medication. The level of control exercised by computing device 112 may help in preventing medication and dosing errors, by reducing the likelihood that a user will remove an incorrect medication from inventory control system 100*a*. In addition, computing device 112 may document and record which item was dispensed, how much was dispensed, which patient the item was dispensed for, and/or which user the item was dispensed to, and may forward that information to inventory and accounting systems.

As will be discussed in greater detail below, some or all of the drawers 104*a* may include one or more sensors that track the inventory and usage of items stored within the drawers 104*a*. Capability of the various sensors may include, for example: measuring the presence or absence of items, measuring the mass and/or weight of an object, measuring the volume of an object, identifying an object, measuring the displacement of an object, determining a position of an object, and/or determining a shape of an object as non-limiting capabilities. Any sensor available in the state of the art to provide at least these capabilities may be included in the systems as envisioned herein. In many cases, these sensors may operate not individually but as a group of two or more, delivering the ability to derive information as a result of fusing the sensor output from the two or more sensors. Some non-limiting examples of sensors include: accelerometers, inertial measurement units (IMU), piezoelectric sensors, piezoresistive sensors, pressure sensors, temperature sensors, volume measurement sensors (such as ultrasound), and/or imaging sensors (including visible and invisible spectrum such as near/far-infrared, ultraviolet). In some embodiments, such sensors may be specific to a particular drawer 104*a*, bin, cassette, and/or portion thereof. In other embodiments, a single sensor and/or group of sensors may be used to monitor multiple drawers 104*a*, bins, and/or cassettes, and possibly an entire interior of the inventory control system 100*a*, such as the entire storage area 102. In some embodiments, the drawers 104*a* may include retractable covers that provide access only to selected items. Such covers are described in U.S. patent application Ser. No. 16/834,950, filed Mar. 30, 2020, previously incorporated by reference. It will be appreciated that various arrangements and designs of drawers 104*a* may be used in conjunction with inventory control system 100*a*.

In some embodiments, the inventory control system 100*a* may include a work surface 106*a*. The work surface 106*a* may be considered as a temporary area available to a user of the inventory control system 100*a* for the purposes of placement of the picked/selected items from the storage area 102. The work surface 106*a* is typically used as a location on which to place selected items during a procedure, such as preparation of a prescribed medication (such as drawing a medication from a vial or an ampoule into a syringe). The work surface 106*a* serves as the space to initially place a sealed syringe and selected vials or ampoules. The work surface 106*a* may further serve as a space for placement of opened seals or wrappers that sometimes cover syringes (for example) or tools used in such preparation. In some embodiments, the work surface 106*a* may be a top surface of the inventory control system 100*a*, while in other embodiments, the work surface 106*a* may positioned at an intermediate height of the inventory control system 100*a*. Additionally, while illustrated as forming substantially all of the top surface of the inventory control system 100*a*, it will be appreciated that in some embodiments, the work surface 106*a* may not be present or may take up only a portion of the footprint of the inventory control system 100*a*. In some embodiments, other than just providing a work area for a user, the work surface 106*a* may include additional features. For example, the work surface 106*a* may include one or more sensors that the inventory control system 100*a* may utilize in monitoring inventory and usage of items stored therein. For example, one or more imaging devices and/or other optical sensors, load sensors, and/or other sensors may be included on or integrated into the work surface 106*a*. As used herein, imaging devices include still and/or video cameras, depth cameras (such as 3D cameras), barcode readers, IR cameras and/or other IR imaging sensors, line scanners, and the like. In some embodiments, these sensors may include a load sensor pad 108 and/or an omnidirectional optical reader 110 as will be discussed in greater detail below. In other embodiments, additional imaging sensors and/or RFID sensors may be incorporated into the work surface 106*a*. Such features allow the user to quickly and easily have items identified for inventory and usage monitoring purposes. Furthermore, in some embodiments, the work surface 106*a* may also be a moveable surface whose position may be adjusted for height and/or location to suit the needs of the user.

The inventory control system 100*a* may also include and/or be in communication with the computing device 112. The computing device 112 may include and/or be communicatively coupled with a display screen 114 and at least one input device 178. While illustrated with the display screen 114 coupled with the work surface 106*a* of the inventory control system 100*a*, it will be appreciated that in some embodiments the display screen 114 may be integrated into a body of the inventory control system 100*a* and/or positioned at other locations (such as extending laterally from or sitting atop a nearby structure) relative to the inventory control system 100*a*. The input device 178 may include a keyboard, mouse, credential reader, microphone, imaging device, biometric reader, and/or other device that enables a user to interact with the computing device 112. In some embodiments, the input device 178 may be incorporated into the display screen 114 by using a touchscreen display screen. In some embodiments, a credential reader may include a wireless reader, such as a Bluetooth, RFID, NFC, and/or other wireless reader that may read information from an active or passive user credential, such as a wearable or device that can be carried (such as a fob, mobile phone, ID, a badge, and/or any other credential device as known in the art). In other embodiments, the credential reader may include a contact reader, such as a chip or magnetic stripe reader. In yet other embodiments, the credential reader may include a biometric reader 181, such as an imaging device or other optical sensor for facial, iris, and/or palm vein authentication, a microphone for voice authentication, a fingerprint reader, and/or other biometric sensor.

The input devices 178 and 181 of computing device 112 allow a user to interact with the inventory control system 100a. For example, the user may interact with the input devices 178 and/or 181 to log in, select a patient and/or procedure, and/or gain access to items stored within the inventory control system 100a. For example, to log into the inventory control system 100a, a user may enter a user name, password, and/or other access credential (which may include a biometric credential) into the computing device 112 to verify that the user is authorized to access the inventory control system 100a and/or a particular item stored therein. In other embodiments, a user may be logged in automatically if a wireless credential of the user is brought within range of a wireless credential reader of the computing device 112. Once a user is logged into the computing device 112, a graphical user interface (GUI) may be presented on the display screen 114 that allows the user to make selections about a patient, procedure, and/or items to be removed or otherwise dispensed from the inventory control system 100a. These selections may be made using any of the input devices 178 and 181 of the computing device 112. In other embodiments, rather than navigating a GUI to make a patient, procedure, and/or item selection, the user may use alternative selection means, such as voice commands, to make the necessary selections.

In some embodiments, the selection of items may begin with the user selecting a patient name. The inventory control system 100a may then provide a list of medications and/or other items that are available for selection for the selected patient at the display 114. In some embodiments, the inventory control system 100a may also provide information about what medications need to be picked from a separate location either due to the nature of the medication or its unavailability at the inventory control system 100a. In some embodiments, the user does not have to select any items prior to being given access to the inventory control system 100a. For example, upon logging into the inventory control system 100a, some items may be readily available (by virtue of drawers 104a being unlocked upon login, for example).

In some embodiments, once the user has selected which items are to be removed from the inventory control system 100a, the inventory control system 100a may provide access to the items, such as by unlocking a drawer 104a and/or otherwise providing access to the storage area 102. Before, during, and/or after the user has removed any items from the inventory control system 100a, the computing device 112 and/or other computer system may use any number of sensors to monitor the removal process, including which items were actually removed from the inventory control system 100a. In some embodiments, the items that are actually removed are correlated with the items that the user originally selected for removal using the GUI. Such sensors may involve sensors integrated into the drawers 104a, those integrated into the work surface 106, and/or any other sensors associated with the inventory control system 100a. In some embodiments, if there is a discrepancy between selected items and the items removed, an indication of the discrepancy may be stored and/or sent to another device, as such behavior may be indicative of diversion behavior, improper use of the items, and/or other improper usage of the inventory control system 100a. The indication may also be presented at the display 114 to notify the user of the discrepancy. The indication may include information, such as which user selected the items and which items were taken that did not match the selections.

In some embodiments, one or more external bins 174 may be provided on or near the work surface 106 that provide locations to discard items for various reasons. For example, the external bins 174 may include a waste bin, a sharps bin, and/or a returns bin. Waste bins may be utilized to discard all or parts of items that cannot be reused, such as some preservative free medication vials that have been opened and/or packing materials. The sharps bins may be used to discard sharp objects such as needles and razors. Return bins may be used to store items that a user wishes to have returned to inventory of the inventory control system 100a at a later time. In accordance with some embodiments of the invention, specifically pertaining to the use of the external bin 174 to receive unopened/sealed items, the inventory control system 100a includes sensors included as part of the external bin 174 to detect what items are returned. Typically, the items returned are intact and sealed and are in condition for being re-used when required. In the present embodiment, the sensors may be adapted to identify one or more of the following: the identity of the returned item, a shape of the returned item, a weight of the returned item, and/or a chemical composition of the returned item. While information from any one of such sensors may be sufficient, it is also envisioned that in some embodiments, final identification of the returned item may depend upon one or more of such sensors. Identity of the returned item may be determined by using image recognition of the label in human-readable form (such as text labels) and/or machine-readable form (such as a barcode or an RFID tag). A shape of the returned item may be determined using an optical means, such as imaging devices (including image and video), with the ability to distinguish between shapes such as a tube, a vial, a tablet, a capsule, a bottle, and/or an ampoule, as non-limiting examples. A weight of the returned item may be directly or indirectly measured. In direct measurement, the returned item is separately measured using means known and available in the art. Indirect measurement of weight of the returned item may be performed by knowing the weight of the external bin 174 before and after the returned item is placed into it. Identification of chemical composition of a sealed item may be performed using spectroscopy (as an example). In yet another embodiment, the external bin may include a chute with one or more sensors integrated within or around it. In order for an item to be returned, the user drops the item into the chute and as the item moves down the chute to the return bin, the one or more sensors are able to identify the returned item by reading the labels around the item as the item moves to the return bin.

In accordance with another aspect of the invention, particularly pertaining to the use of the external bin 174 as a waste collection unit, the external bin 174 may include sensors that are able to distinguish the physical and chemical characteristics of the wasted item. For example, when an empty vial of a particular medication is discarded, the external bin 174 would be able to identify the vial using one sensor type (such as optical) and verify that it is empty using a different sensor type (such as weight). In another example, when unused medication from a syringe has to be discarded into the external bin 174, there may be chemical verification of the unused medication (to confirm that what appears to be a particular medication is actually what it is supposed to be). This feature is particularly useful for the discard of unused controlled substances like propofol or morphine, etc. The above-mentioned sensors and examples of use cases may be used separately or in conjunction with one another. This description should not be construed as limiting.

In yet another embodiment of the inventory system, the external bin 174 may include portions or compartments that allow a return as well as a discard. In certain other embodiments, the portions for return and discard may be subdivided compartments, or they may be spatially separated to allow a user to separately handle each compartment based on its usage. All these variations should be considered as being part of the presently disclosed inventory control system 100*a*.

Know the User

As discussed above, many applications of inventory control systems, such as inventory control system 100*a*, may require a user to log into the inventory control system 100*a* prior to gaining access to the storage area 102. Other log in and authentication processes that may be used are described in U.S. patent application Ser. No. 16/834,950, filed Mar. 30, 2020, which was previously incorporated by reference. Several types of access credentials may be utilized. In some embodiments, logging in may be done by a user entering access credentials, such as a user name, password, and/or other credential. However, it may be desirable for a user to gain access quicker and/or easier than is achievable with manually keying in access credentials into a keyboard, keypad, and/or touchscreen. In such embodiments, other forms of access credentials may be utilized. For example, possession-based credentials may be utilized. In some embodiments, a possession-based credential may be in the form of a universal serial bus (USB) dongle, chip card, magnetic stripe card and/or other device that may be inserted into a port of a credential reader and/or otherwise scanned by a credential reader of the computing device 112. Once inserted or read by the computing device 112, the credential device may provide access to the patient, procedure, and/or item selection systems and may retrieve one or more items from the inventory control system 100*a*.

In other embodiments, a possession-based access credential may be in the form of a contactless device, such as a radio frequency (RF) wireless device that may be wirelessly read by a credential reader of the computing device 112. For example, the credential may be in the form of a card (such as an employee identification card), mobile phone, wristband, watch, other wearable, and/or other high integrity possession-based authentication object that may have an integrated RF chip. This enables the user to approach the inventory control system 100*a* while in possession of one of these RF-enabled access credentials and gain access to the inventory control system 100*a* with little to no log in action necessary by the user. For example, the RF-enabled access credential may include a Bluetooth® enabled device (which may include smart phones and tablet computers), RFID chip or tag, and/or other short range RF communication protocol that enables the access credential to be read by the credential reader of the computing device 112 as soon as the user is within a signal or detection range of the credential reader. In other embodiments, the access credential may operate using a shorter range communications protocol, such as near field communication (NFC). In such embodiments, the user may need to actively bring the access credential within signal range of an NFC credential reader of the computing device 112. In some embodiments, an access credential may be configured to emit sound (including ultrasound and/or other frequency ranges), such as audio chirps, that are detectable by a credential reader of the inventory control system 100*a* to authenticate a user. For example, a user's smart phone and/or other credential may emit a particular sound signal that is used to unlock the computing device 112 for use. Similarly, some embodiments may use credentials that emit light waves (in the visible and/or invisible spectrum) that are useable as a signature to gain access to the inventory control system 110*a*.

In some embodiments, the RF chip of the access credential may be a passive chip that is powered by electromagnetic energy transmitted from an RFID reader/antenna of the credential reader of the computing device 112 and or by harvesting ambient light. In other embodiments, the access credentials may include active RFID chips or tags that are powered by a battery (either a dedicated battery or a battery of a device containing the RFID chip or tag) and may continuously broadcast a signal containing the necessary access credentials for a particular user. Typically, such active RFID tags have a longer range at which the data can be read than the passive RFID tags. In some embodiments, the credential reader of the computing device 112 may be designed to have a predetermined signal/detection range that ensures that a user is sufficiently close to the inventory control system 100*a* prior to reading a possession-based access credential. For example, a signal strength of the credential reader and/or RFID tag may be adjusted such that a desired signal range is achieved that helps prevent the computing device 112 from attempting to log in multiple users or an incorrect user when multiple people are positioned proximate the inventory control system 100*a*. In other embodiments, the range of the inventory control system 100*a* may be limited to a particular room or area in which the inventory control system 100*a* is located. For example, RF shielding and/or other materials may be provided around a periphery of the room to ensure that only access credentials within the room may be detected by the credential reader of the inventory control system 100*a*. In other embodiments, location beacons may be provided in an area around each inventory control system 100*a*. GPS signals from each beacon may be used to provide locations to each RFID device, and the inventory control system 100*a* may only interact with devices that are nearby.

In some embodiments, rather than using a knowledge-based or possession-based access credential, the inventory control system 100*a* may include one or more biometric readers that enable users to log in without carrying a physical access credential device. For example, the computing device 112 of inventory control system 100*a* may include or be communicatively coupled with biometric reader 181 such as a fingerprint reader, a speaker for voice recognition, one or more optical sensors (such as imaging devices, infrared (IR) scanners) for iris scanning, facial detection, palm vein recognition, and/or other biometric authentication techniques.

When using biometric authentication techniques that involve imaging a portion of a user (such as, but not limited to, facial recognition) anti-spoofing measures may be taken to help thwart fraudulent authentication attempts, such as when one user attempts to present a photograph, video, and/or mask of a different person who is an authorized user of the inventory control system 100a to an image sensor of the inventory control system 100a. Such anti-spoofing measures may include, for example, active face liveness detection and/or passive face liveness detection. For active face liveness detection, the user may be asked to perform a specific action, such as nodding, blinking, smiling, and/or other facial pattern or gesture. If the computing device 112 determines that the user has performed the requested action, the computing device 112 may determine that the user being imaged is real and may be authenticated properly. In some embodiments, the facial pattern or gesture may be the same each time a user logs on, while in other embodiments, any number of facial patterns and/or gestures may be cycled through and/or randomly assigned to a particular login attempt. Using multiple facial patterns and/or gestures adds an additional layer of security that helps prevent videos from being displayed to the imaging device of the computing device 112 in an attempt to fraudulently login to the inventory control system 100a.

Passive face liveness detection may involve various techniques. For example, some embodiments may utilize face flash liveness which uses a light element to illuminate the user (or copy of the user) with visual light or light not visible to a human eye, such as infrared light. The reflectance of the user is measured, allowing the imaging device to capture how the light from the screen and/or other light source reflects on the face. The computing device 112 can then determine whether the illuminated face belongs to a live person or a reproduction (such as a photo or a video) based on the measured reflectance. Some embodiments may perform passive face liveness detection using eye blink detection. For example, blinking by the user may be detected and timed. If no blinking is detected and/or the detected blinking is performed at a rate that is not common, the computing device 112 may deem the authentication attempt to be based on a reproduction of a user. Some embodiments may employ the use of trained convolutional neural networks (CNNs) to detect the authenticity of a user detected by an imaging device of the computing device 112.

Additional passive anti-spoofing techniques may involve the use of infrared and/or 3-dimensional imaging devices, which may be able to readily distinguish between human users and reproductions such as 2-dimensional photographs and/or videos, as well as both 2-dimensional and 3-dimensional masks. For example, 3-dimensional imaging devices may be able to measure the depth of various features of an image and be able to distinguish between flat objects (e.g., photographs and/or display screens that may be showing a user's image) and 3-dimensional objects (such as a user or 3-dimensional mask). IR imaging devices (or other IR sensors) are capable of determining whether an image being detected has a thermal profile that matches that of a specific user and/or generally matches that of a human. For example, the thermal profile of a photo or display screen will not match that of a human. Similarly, both 2-dimensional and 3-dimensional masks will not have a thermal profile similar to a human unless a very sophisticated mask is utilized.

The use of voice recognition as an access credential typically involves a user speaking a particular word or phrase into a speaker of the inventory control system 100a. The user's voice signature (tone, pitch, cadence, etc.) may be compared to a previously stored voice signature of known authorized users in order to detect whether the user can be authenticated. In some embodiments, rather than having a user speak a same predetermined word or phrase, the inventory control system 100a may prompt the user to speak a random one of a number of words or phrases in order to reduce the likelihood that someone could create an audio recording of an authorized user speaking a predetermined passphrase.

In some embodiments, multiple forms of credentials may be required to log into further enhance the security of the inventory control system 100a. For example, a physical access credential may be a chip card that requires the user to enter a personal identification number (PIN) in order to log in. Such embodiments require that the user have both possession of an access credential and knowledge of an alphanumeric login credential in order to be logged into the inventory control system 100a. In other embodiments, the inventory control system 100a may require both a biometric credential (such as facial recognition) and a physical credential (such as a contactless credential device) in order to log into the inventory control system 100a. It will be appreciated that any combination of knowledge-based, possession-based, and/or biometric access credentials may be utilized to meet the security needs of a particular application. Additionally, in some embodiments, multiple types of a single type of credential may be utilized. For example, multiple forms of biometric credentials may be utilized (such as fingerprint and voice) to help further reduce the likelihood of fraudulent authentication.

Additionally, in some embodiments, backup authentication means (biometric and/or otherwise) may be assigned in the instance that a particular access credential is not available at a particular time. For example, if a user has a respiratory illness and cannot speak or can only speak with noticeable changes to his voice, an alternative to a voice recognition system (such as an alternative biometric credential, a knowledge-based credential, and/or a possession-based credential) may be utilized. Similarly, if a possession-based credential is not available, such as if an RF chip is not functioning properly or a user forgets a physical access credential, the inventory control system 100a may provide an alternative authentication process that does not involve the unavailable access credential device. In some embodiments, a user may select an alternative authentication process, while in other embodiments such processes may be automatically provided by the inventory control system 100a upon one or more failed attempts at successful authentication.

In some embodiments, the inventory control system 100a may provide multiple levels of credential security to simplify re-logging in of active users. For example, at a first login, a strong biometric and/or credential security is required. Once that user has been authenticated, the user can re-login with a less secure biometric, such as voice recognition. At the end of the procedure and/or after a predetermined timeout, this less secure login would expire. This may be particularly useful in a use case involving an anesthesiologist. For example, the anesthesiologist may not have a mask on when the anesthesiologist first logs in and starts prepping for a procedure. Once the patient arrives and sterile field is established, all medical personnel put masks and gloves on. At this point, fingerprint and face recognition are not available. If, during the procedure the anesthesiologist is auto-logged out, the anesthesiologist can easily re-login with a less secure voice authentication. At the end of the procedure, the anesthesiologist logs out of the system and use of less secure credentials expire. This revocation of less secure credentials can also be on a predetermined expiration time out, and not be dependent on the anesthesiologist remembering to logout.

In one particular application, the inventory control system 100a may be utilized as a cart for a physician, such as an anesthesiologist. Oftentimes, such users have a need to access medications and/or equipment stored within an inventory control system 100a quickly. Additionally, these users typically do not view the tracking of inventory as part of their duties. As a result, in such applications, the inventory control system 100a may be operated in a manner that ensures that the user may be logged on quickly and efficiently, with as little interaction as possible by the user. For example, in such embodiments, the inventory control system 100a may require hands free authentication credentials, such as possession-based wireless and/or contactless credential devices and/or biometric authentication credentials. Oftentimes, there may be a desired to utilize a contactless biometric authentication credential (i.e., not fingerprint) as such contact may be time consuming and/or less ergonomic than contactless biometric credentials. As a result, an inventory control system 100a for a physician-based application may be configured to utilize facial, iris, palm vein, and/or voice credentials as login credentials. Additionally, hands free authentication credentials (possession-based and/or biometric-based) may be particularly useful in applications in which some or all of the users will be accessing the inventory control system 100a with gloved hands, as gloves may make it more difficult for a user to key in access credentials, manipulate a contact-based credential device, and/or supply contact-based biometric credentials such as fingerprints. While discussed with using hands free authentication credentials for inventory control systems 100a that are accessed by physicians, it will be appreciated that in many applications authentication forms that require user actions and/or hand usage may be utilized in some embodiments.

Selecting a Patient

Once a user is logged into the inventory control system 100a, the user may be prompted to enter additional details regarding what items are to be removed. For example, one or more items may be associated with a particular location and/or task. This may be particularly relevant in medical applications in which medications and/or other medical items are to be used in conjunction with a particular treatment and/or a particular patient. To enter these details, a user may interact with the computing device 112 using one or more input devices, such as input device 178 including a keypad, a keyboard, a mouse, a touchscreen display 114, and/or other input device. In some embodiments, the selection procedure may be voice controlled such that a user may select one or more items, tasks, patients, etc. Oftentimes, voice controlled systems may also include a manual entry selection system as a backup in case the voice control system is not functioning properly or in the event that a user has a respiratory illness or other cause of voice change or voice loss that may make it difficult to operate a voice controlled selection system.

In some embodiments for medical applications, a procedure list may be provided to the inventory control system 100a that includes a limited number of patients, procedures (e.g., treatments), locations, and/or users (nurses, techs, physicians, orderlies, and the like) to choose from. In some embodiments, the procedure list may be populated by scanning information from a patient wristband, chart, and/or other data source. In some embodiments, the procedure list may be manually populated at the inventory control system 100a and/or at a remote computing device that then communicates the procedure list to the inventory control system 100a. In other embodiments, the procedure list may be automatically populated using a hospital (or other facility) scheduling system. For example, an electronic health records (EHR) system may be used to automatically populate the procedure list with data regarding specific patients and/or procedures that are currently on a schedule. In some embodiments, the EHR system may utilize knowledge about where a particular inventory control system 100a is located in order to populate the procedure list. For example, if an inventory control system 100a is located in an intensive care unit (ICU), the procedure list for the inventory control system 100a may only be populated with only patients and/or procedures that correspond to patients present in the ICU, procedures performed in the ICU, and/or medical personnel staffing the ICU. Similarly, procedure lists may be provided for each inventory control system 100a in a designated area of a facility (NICU, maternity ward, operating room, etc.). In other embodiments, an inventory control system 100a may include a procedure list that contains data about each patient and/or scheduled procedure in an entire facility. In other embodiments, the procedure list may be populated with any procedure that may be performed in the facility, regardless of likelihood or location of the inventory control system 100a. The procedure list for a given inventory control system 100a may be presented on a GUI displayed on the display screen 114, allowing a logged in user to access the procedure list and make selections of items to access for one or more patients and/or procedures using a variety of methods, including touch screen, voice commands and/or other input techniques.

In some embodiments, a location of the inventory control system 100a may be preprogrammed into the inventory control system 100a (such as by tagging the inventory control system 100a as being associated with a particular facility and/or portion thereof). In other embodiments, the EHR system and/or other central computing system may be programmed with a location of each respective inventory control system 100a in a given facility. For example, a location may be associated with a serial number and/or other unique identifier of the inventory control system 100a such that the EHR system has knowledge of the location of each inventory control system 100a in a facility. In other embodiments, the location may be determined based on a wireless connection (such as a Bluetooth beacon) and/or other RFID tag that is usable to determine a location of each inventory control system 100a in a facility and associate the location with an identifier of the respective inventory control system 100a. In other embodiments, each inventory control system 100a may include one or more other location determining features, such as a global positioning satellite (GPS) sensor and/or other location sensor that may determine where in a facility the inventory control system 100a is located.

In some embodiments, not only may a procedure list be populated based on a location and/or known patients and/or procedures, but the storage area 102 of the inventory control system 100a may be populated with items, such as tools, medications, instruments, and the like based on the location and/or expected function of the inventory control system 100a. For example, in a neonatal ward, only items and/or medications (and doses) that are relevant to the treatment of infants may be stored within the inventory control system 100a. Similarly, an inventory control system 100a in an operating room may be stocked with items and medications that may be used during surgical and/or other procedures. In some embodiments, such as where a procedure list is not used, is out of date, is incomplete, etc., a user may manually enter data about a patient and/or procedure into the computing device 112.

Logged in users may interact with the procedure list (or other selection menu) to select item criteria (patient, case, expected procedure, location, medical personnel, etc.) using the GUI presented on the display screen 114. For example, the user may select and/or key in any necessary data and/or selections using the input device 178 of the computing device 112 and/or may navigate the selection process using voice commands.

In some embodiments, rather than needing to select a patient and/or procedure, once a user is logged into the inventory control system 100a only an item to be removed need be selected. This may be particularly useful in non-medical applications and/or other applications that do not involve patients and/or do not need to associate a particular item with recipients associated with the task being performed using the particular item. While patients and/or other recipients may not be involved, the inventory control system 100a may oftentimes still require a selection of a task, project, and/or location associated with the use of an item. For example, if a tool is being removed from an inventory control system 100a in a construction application, the user may need to select a particular project that the tool is being used on. This ensures that not only may the use of the item be attributed to the logged in user, but also that a specific task may be associated with the tool, which may better help track the usage of the tool. This may also make tracking down lost items easier, as a last known location and/or project associated with the item may be known.

In some embodiments, once a user is logged into the inventory control system 100a, the user may gain access to all of the contents within the storage area 102. In other embodiments, one or more users of the inventory control system 100a may have clearance levels that provide access to only a subset of the storage area 102. For example, a nurse may have access to only non-controlled substances, while a physician may have access to an entirety of the storage area 102, including controlled substances such as narcotics. In some embodiments, such controlled items may be housed in separate containers (such as high security drawers) while in other embodiments, controlled and non-controlled substances and/or other items may be stored within a single area, such as in a single drawer 104a. In some embodiments, to further enhance security of these controlled items when placed in drawers 104a with less secure items, the controlled items may be placed in lockable bins that are secured within and/or otherwise provided within a drawer 104a and/or other feature of the storage area 102. In other applications, each user may have access to items that pertain to their particular job function and/or training specialties. For example, if a user has not been certified to administer a particular form of treatment and/or perform a type of procedure, the user may not be given access to portions of the storage area 102 that contain items that are used only in the particular treatment and/or procedure.

Access

Once a user has selected any items to be retrieved from the inventory control system 100a (as well as entering any other data, such as patients, procedures, tasks, locations, personnel, and the like), the inventory control system 100a may provide access to the interior of the storage area 102 to allow the user to take the items that the user is authorized to possess and/or administer. In some embodiments, this may be achieved by the computing device 112 sending an unlock command to one or more drawers 104a positioned within the storage area 102. The unlock command may cause a locking mechanism, such as a solenoid-actuated lock, to disengage and allow the drawer 104a to be opened. In some embodiments, one or more bins within a cassette of the drawer 104a may be unlocked to provide access to controlled items (such as narcotics).

Once the user gains access to the storage area 102, the user may take the selected items. In some embodiments, multiple drawers 104a and/or other storage units may need to be accessed by a user to retrieve all of the items that have been selected for use. Once the items have been taken, the user may close the drawer 104a and/or other portion of storage area 102. The drawers 104a and/or other partitions may be locked again by the inventory control system 100a to secure any remaining items within the storage area 102.

Inventory Management

The inventory control system 100a is also configured to conduct inventory of the contents of the storage area 102. This inventory may be performed before, during, and/or after a user has accessed the storage area 102. For example, counts performed before and after a user accesses the storage area 102 can be compared to determine what items were removed and/or added to the storage area 102. In some embodiments, a count before the user access is performed after the user selects one or more items for removal at the computing device 112, while in other embodiments the inventory control system 100a may only utilize count data from drawer-close events. Typically, this inventory may be conducted based on data from one or more sensors that are positioned within and/or proximate the interior of the storage area 102, such as by placing one or more sensors within or near each of a number of drawers 104a and/or other objects. In some embodiments, the inventory may be performed in whole or in part by using one or more sensors that are integrated into and/or coupled with the work surface 106a of the inventory control system 100a.

In some embodiments, the inventory sensors of the inventory control system 100a may include vision sensors, such as imaging devices, IR sensors, and the like that are capable of optically counting and/or confirming the presence of one or more items present within the storage area 102 of the inventory control system 100a. These vision sensors may be positioned such that an inventory of an entirety of the storage area 102 and/or work surface 106a may be monitored for changes to the inventory of the inventory control system 100a.

In some embodiments, the contents of an inventory control system 100a can also be scanned remotely to confirm inventory. A remote computing device may request an inventory count from one or more idle inventory control systems 100a. Both processed inventory results and compressed drawer images can be uploaded to a server. The results may be tagged with metadata that identifies the user, the date, and/or the medications that the inventory control system 100a determined to have been dispensed. This metadata may allow users to lookup previous transactions and/or may allow a computing device, such as computing device 112 and/or a remote device, such as the central pharmacy 198 to determine an inventory of one or more items within the respective inventory control system 100a. Additionally, by tagging the transactions with metadata, information about which users accessed the various items, as well as when such access was provided, may be used, for example, to help identify possible diversion behavior.

Figure 3A:
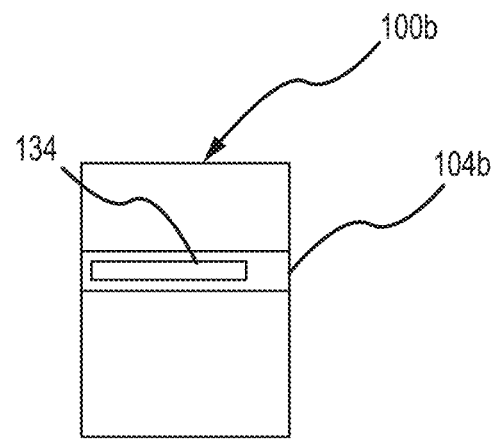
FIG. 3A illustrates a side view of an inventory control system having imaging devices mounted on pivoting arms according to embodiments of the present invention.
Figure 3B:
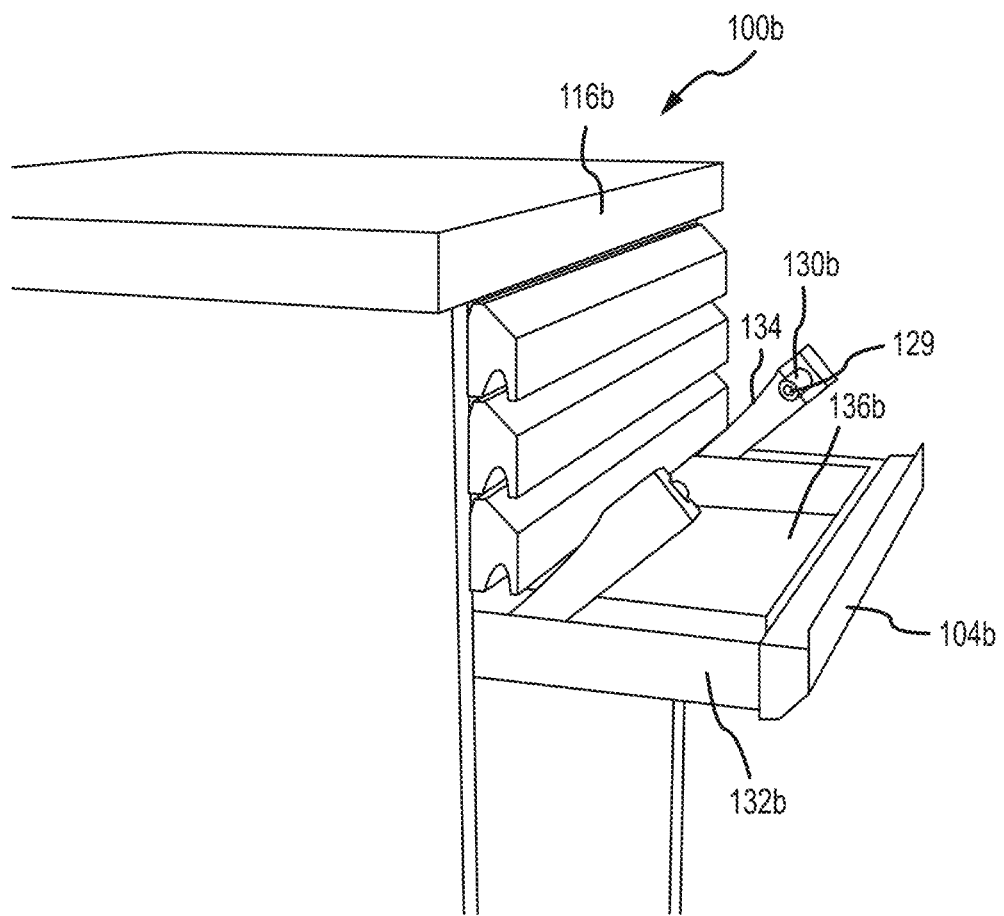
FIG. 3B illustrates a side view of the inventory control system of FIG. 3A with the pivoting arms in an intermediate position.
Figure 3C:
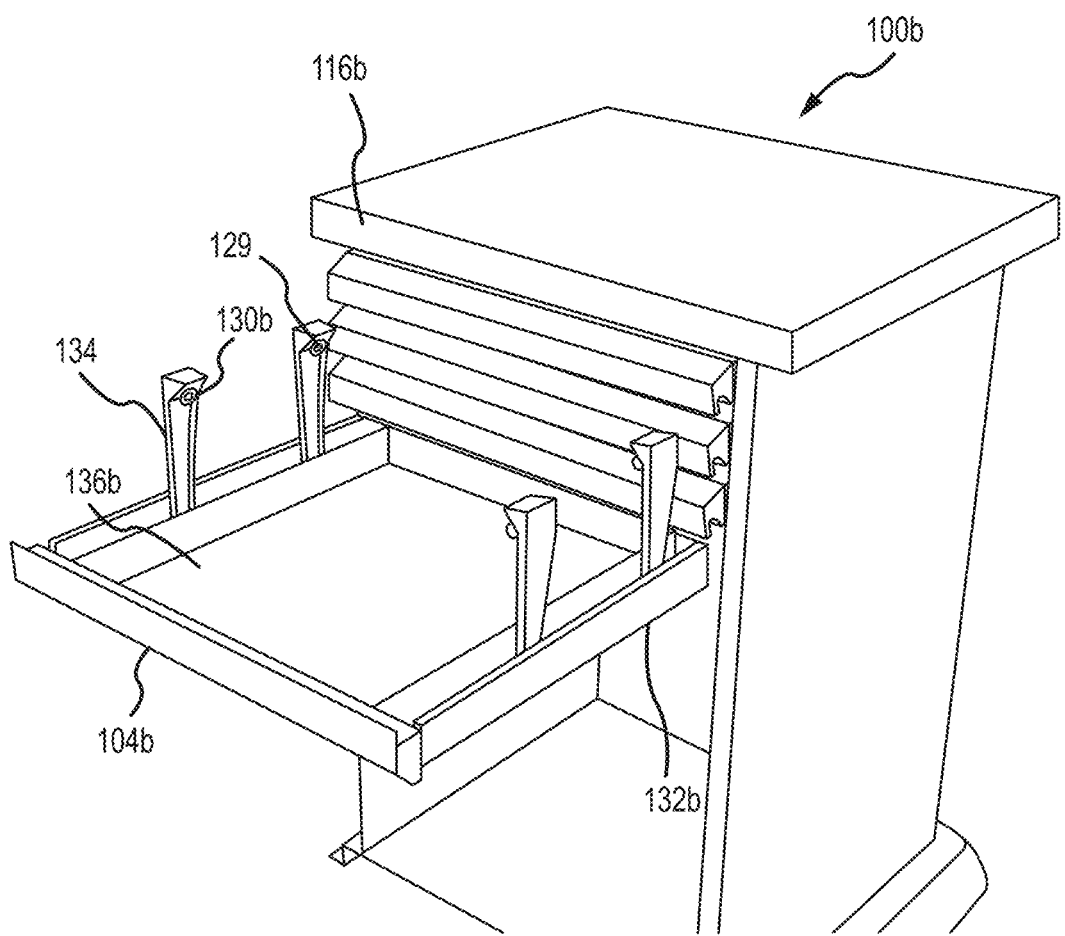
FIG. 3C illustrates a perspective view of the inventory control system of FIG. 3A with the pivoting arms in an elevated position.

In some embodiments, image capture devices (e.g., vision scanners such as imaging devices, IR sensors, and the like) may be configured to monitor the inventory of an inventory control system while a drawer is open. FIGS. 3A-3C illustrate one embodiment of an inventory control system 100b, which may be similar to the inventory control system 100a described above, and includes a vision sensor system. As illustrated, inventory control system 100b includes one or more drawers 104b (which may be similar to other drawers described herein) that may be provided within a storage area of the inventory control system 100b (which may be similar to storage area 102) and that may contain one or more items. In the present embodiment, some or all of the drawers 104b include a number of imaging devices 130b. Each imaging device 130b is coupled with a lateral side 132b of the respective drawer 104b via a pivoting arm 134. In some embodiments, the pivoting arms 134 may be coupled with the lateral sides 132b at positions that are outside of a storage region 136b of the drawer 104b, while in other embodiments, the pivoting arms 134 may be coupled within an interior of the storage region 136b. The pivoting arms 134 are designed to maneuver the imaging devices 130b between a storage position and an active position. As best illustrated in FIG. 3A, the pivoting arms 134 may be pivoted downward such that the pivoting arms 134 are at least substantially parallel to the lateral sides 132b of the drawer 104b. This orientation allows the pivoting arms 134 to fit within a height of a respective drawer 104b such that the drawers 104b of the inventory control system 100b may be stowed adjacent one another in the storage area.

As the drawer 104b is being drawn out of the interior of the storage area, the pivoting arms 134 may begin pivoting upward away from a base of the drawer 104b as illustrated in FIG. 3B. For example, the pivoting arms 134 may be spring biased to pivot upward and in a direction of a central axis of the inventory control system 100b when not constrained by features positioned above the pivoting arms 134 (such as drawers 104b positioned above the pivoting arms 134, a frame of the inventory control system 100b that defines the storage area, a bottom surface of a work surface (which may be similar to work surface 106), and/or other structure. The pivoting arms 134 may be configured to pivot to the active position in which the pivoting arms 134 are at least substantially perpendicular with a sliding axis of the drawer 104b as best illustrated in FIG. 3C. Once any items are removed from the drawer 104b, the drawer 104b may be pushed and/or otherwise maneuvered back into the storage area. As the drawer 104b moves inward, an inward facing side of each of the pivoting arms 134 may contact a front face of one or more drawers 104b positioned above the pivoting arms 134, a frame 116b of the inventory control system 100b that defines the storage area, the work surface, and/or other structure of the inventory control system 100b. This contact may cause the pivoting arms 134 to pivot downward away from the central axis of the inventory control system 100b in an opposite direction of the spring force until the pivoting arms 134 are again in the storage position shown in FIG. 3A.

When in the active position, a lens 129 of each imaging device 130b is positioned proximate a top of each respective pivoting arm 134 which elevates the imaging devices 130b to a sufficient height to achieve a viewing angle that is able to capture all or a substantial portion of the storage region 136b of the drawer 104b. In the present embodiment, the imaging devices 130b work to image and inventory the contents of the drawer 104b while the drawer 104b is in an open position. In some embodiments, the entire storage region 136b may be imaged using a single imaging device 130b, while in other embodiments, each imaging device 130b may be focused to capture an image of only a portion of the storage region 136b. In such embodiments, the various images of portions of the storage region 136b may be stitched together as described herein to form a single image showing the entire storage region 136b. In yet other embodiments, rather than relying on image stitching, each imaging device 130b may be positioned to image an entirety of one or more sections (such as individual bins) of the storage region 136b. In such embodiments, a computing device of the inventory control system 100b (similar to computing device 112) may analyze the images, detect section partitions (such as bin edges), and determine which sections of the storage region 136b are entirely within a single image and analyze these image regions to conduct an inventory count while ignoring incomplete sections of the storage region 136b found in a given image. In some embodiments, each image may include only a single full bin, while in other embodiments some or all of the images may include multiple full bins.

While illustrated here with four imaging devices 130b (two on either lateral side 132b of the drawer 104b), it will be appreciated that any number of imaging devices 130b may be utilized in various embodiments, including the use of a single imaging device 130b in some embodiments. While illustrated with a symmetrical arrangement of imaging devices 130b, it will be appreciated that in some embodiments the imaging devices 130b on opposite lateral sides 132b of the drawer 104b may be staggered and/or otherwise offset from one another. Additionally, some embodiments may utilize different numbers of imaging devices 130b on each lateral side 132b of the drawer 104b. Additionally, in some embodiments, multiple imaging devices 130b may be provided on a single pivoting arm 134. For example, two or more imaging devices 130b may be positioned side by side and/or arranged above or below one another on one or more of the pivoting arms 134. Oftentimes, these imaging devices 130b may be oriented at different angles to image different sections of the storage region 136b.

In some embodiments, lighting elements (not shown) may be provided to illuminate some or all of the contents in order to improve the clarity of images captured by one or more of the imaging devices 130b. For example, a lighting element may be provided on a surface of the drawer 104b, on a lid covering the drawer 104b, on an internal vertical surface of the drawer 104b, and/or proximate a front end of another drawer 104b that is positioned higher than the opened drawer 104b. In yet other embodiments, the lighting element(s) may be positioned on the pivoting arm 134 above, below, and/or laterally relative to any imaging devices 130b provided on the pivoting arms 134.

Figure 4A:
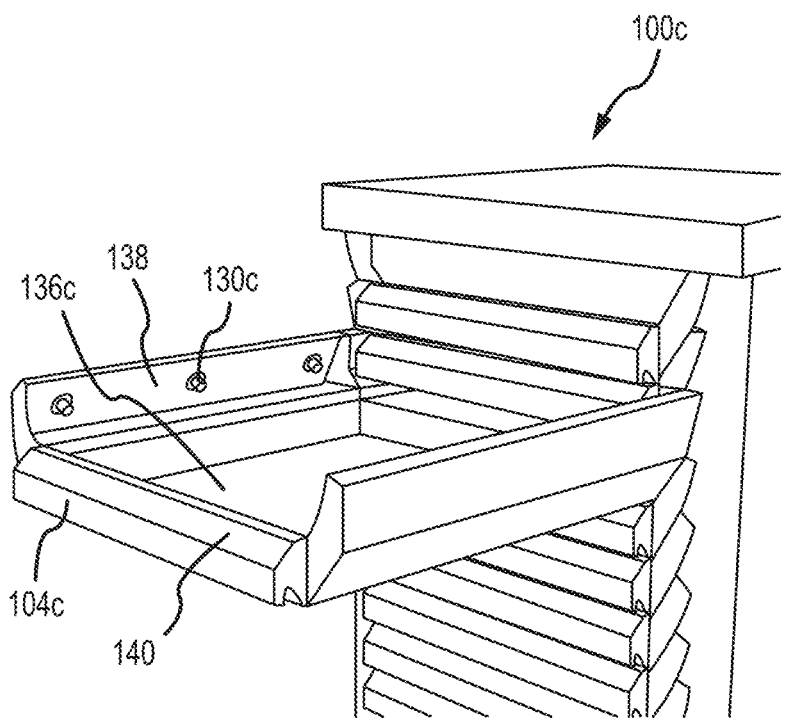
FIG. 4A illustrates a perspective view of an inventory control system having imaging devices mounted on wings of a drawer according to embodiments of the present invention.
Figure 4B:
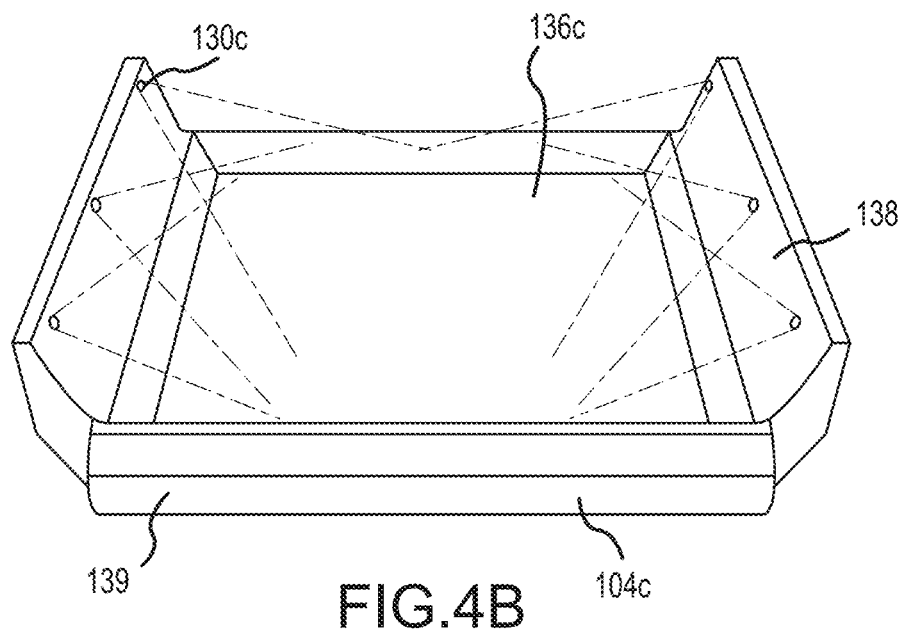
FIG. 4B illustrates the drawer of the inventory control system of FIG. 4A.

FIGS. 4A and 4B illustrate another embodiment of an inventory control system 100c (which may be similar in various respects to the other the inventory control systems described herein). Inventory control system 100c includes one or more drawers 104c that contain one or more imaging devices 130c. Each drawer 104c includes a wing 138 and/or other upward projection positioned on lateral sides of the drawer 104c. A base 139 of each drawer 104c has a lower profile, allowing the base 139 of one drawer 104c to nest between the wings 138 of the drawer 104c below it. A number of imaging devices 130c may be positioned on an interior-facing surface of one or both of the wings 138, with the imaging devices 130c being angled down and in toward the interior of the storage region 136c of the drawer 104c. Here, six imaging devices 130c are provided (three on each lateral side of the drawer 104c) that produce overlapping images of various portions of the storage region 136c. In some embodiments, the entire storage region 136c may be imaged using a single imaging device 130c, while in other embodiments, images from multiple imaging devices 130c may be stitched together to form a single image showing the entire storage region 136c. In yet other embodiments, each imaging device 130c may be positioned to image an entirety of one or more sections of the storage region 136c. Due to the nesting nature of the drawers 104c of the present embodiment, the imaging devices 130c may be configured to image the storage region 136c when the drawer 104c is in an open or partially open state that exposes at least one of the imaging devices 130c to the interior of the storage region 136c.

Figure 5A:
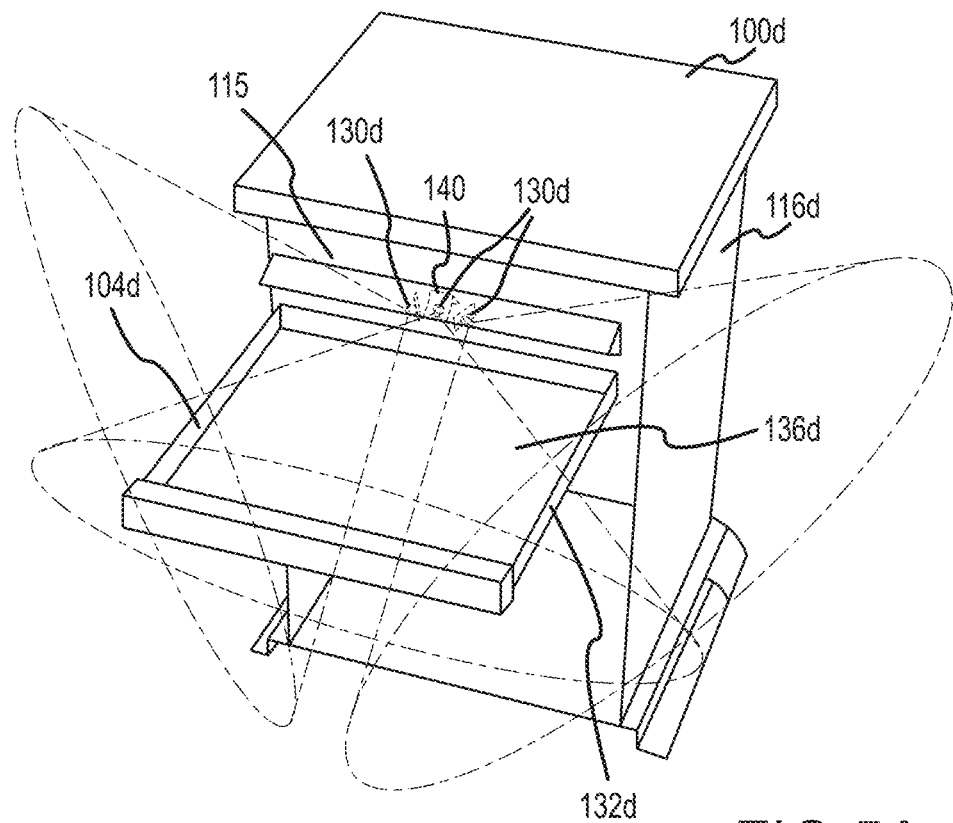
FIG. 5A illustrates a top perspective view of an inventory control system having imaging devices mounted on a housing of the inventory control system according to embodiments of the present invention.
Figure 5B:
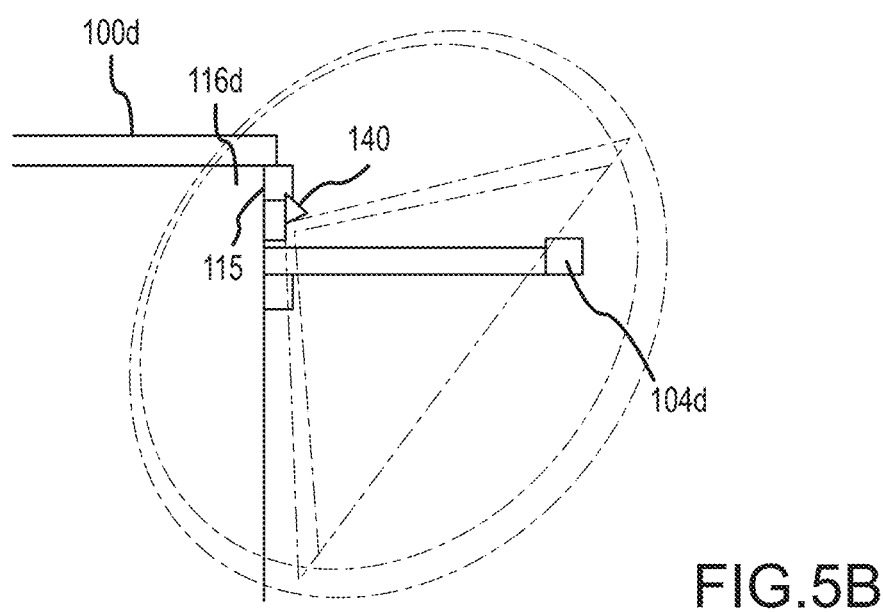
FIG. 5B illustrates a side elevation view of the inventory control system of FIG. 5A.

FIGS. 5A and 5B illustrate an embodiment of inventory control system 100d. Inventory control system 100d operates using principles similar to those described above and uses multiple imaging devices 130d to conduct inventory of a storage area of the inventory control system 100d. For example, rather than having imaging devices 130d that are dedicated to a particular drawer 104d, imaging devices 130d are mounted on a front surface 115 of a housing 116d of the inventory control system 100d that is above the drawers 104d to capture images of the interiors of one or more drawers 104d. In the present embodiment, imaging devices 130d are wide angle imaging devices that have a field of view of at least about 100 degrees (although the use of more imaging devices 130d may reduce the necessary field of view of some or all of the imaging devices 130d) and are positioned such that the imaging devices provide images that overlap with one another. As shown, three downward-pointing imaging devices 130d are utilized, with a lateral imaging device 130d directed at either lateral side 132d of the drawer 104d and a third center imaging device 130d pointed outward along a central longitudinal axis of the drawer 104d. Such an arrangement of imaging devices 130d enables the image fields of the two lateral imaging devices 130d to overlap at least partially with the image field of the central imaging device 130d. As described in relation to other embodiments, individual images from the imaging devices 130d may be stitched together to form a single image showing the entire storage region 136d and/or may include an entirety of one or more sections of the storage region 136d.

In some embodiments, the imaging devices 130d may include and/or be mounted on an adjustable frame 140 which allows a vertical angle of the imaging devices 130d to be adjusted. In particular, the adjustable frame 140 allows the imaging devices 130d to be pivoted up and down to capture images of the storage regions 136d of drawers 104d of various heights on the inventory control system 100d. In some embodiments, operation of the adjustable frame 140 may be automated, such as using an electric motor that is operated using a controller (such as computing device 112). In such embodiments, as a particular drawer 104d is unlocked and/or otherwise accessed, the computing device 112 or other controller may cause the motor of the adjustable frame 140 to adjust a vertical angle of the imaging devices 130d such that the image fields of the imaging devices 130d cover an entirety of the storage region 136d of the respective drawer 104d that is being accessed. In such a manner, the imaging devices 130d may be fixed at a single height/position on the housing 116d of the inventory control system 100d while still being able to capture images of the contents of each of the drawers 104d. For example, each drawer 104d may be associated within the computing device 112 (or other controller) with a particular angle for the adjustable frame 140.

It will be appreciated that in some embodiments, a single adjustable frame 140 may house or otherwise support multiple imaging devices 130d. In other embodiments, the adjustable frame 140 may support all of the imaging devices 130d on the inventory control system 100d. In other embodiments, some or all of the imaging devices 130d may be positioned on a dedicated adjustable frame 140. Additionally, while illustrated with three imaging devices 130d, it will be appreciated that in some embodiments, more or fewer imaging devices 130d may be utilized, with different number of imaging devices 130d requiring different lens capture angles to capture the entire contents of the various drawers 104d. Additionally, while illustrated with the imaging devices 130d positioned proximate one another near a center of the inventory control system 100d, the imaging devices 130d may be spread out from one another and/or positioned at non-central locations of the inventory control system 100d in some embodiments.

Figure 6A:
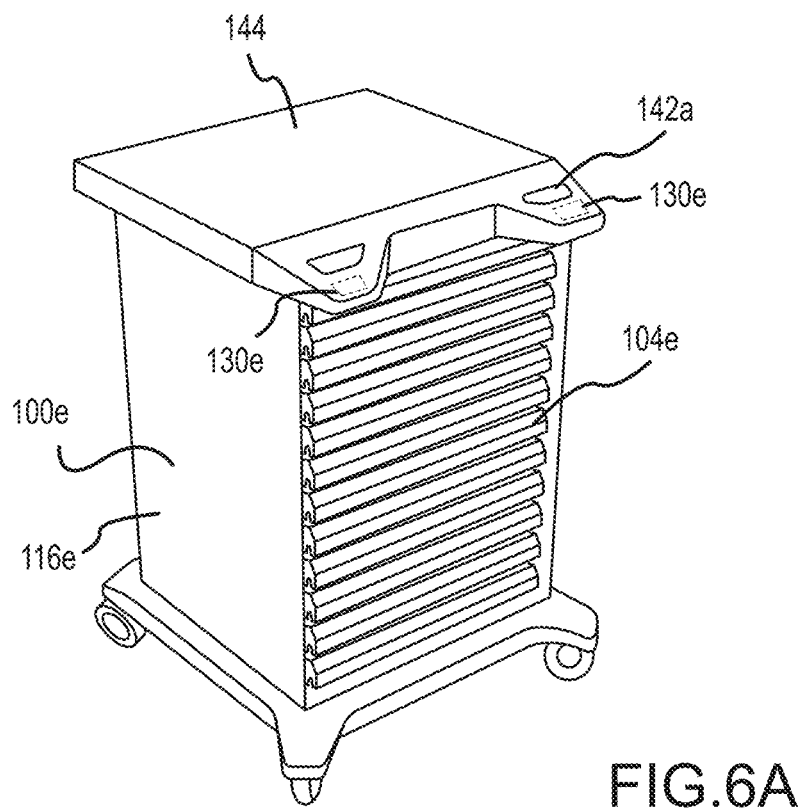
FIG. 6A illustrates a perspective view of an inventory control system having imaging devices mounted on an alternative protrusion of a housing of the inventory control system according to embodiments of the present invention.
Figure 6B:
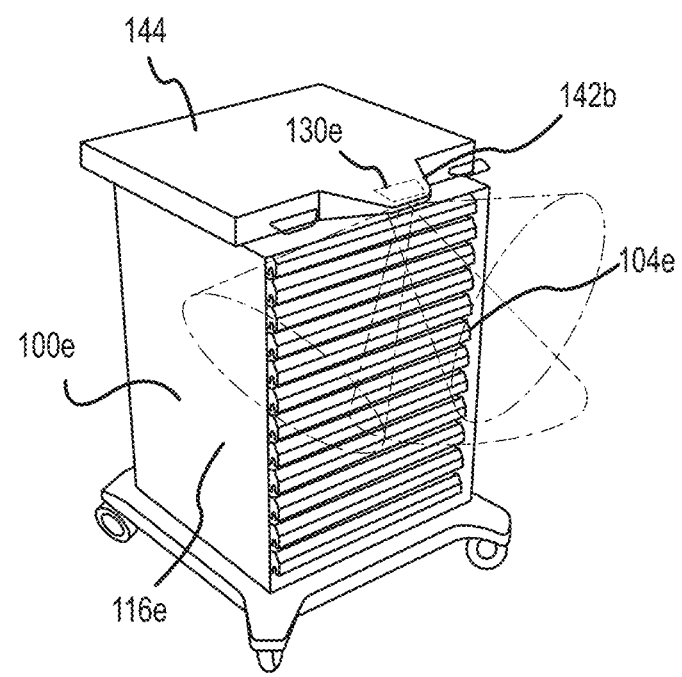
FIG. 6B illustrates a perspective view of an inventory control system having imaging devices mounted on alternative protrusions of a housing of the inventory control system according to embodiments of the present invention.

FIGS. 6A and 6B illustrate alternative embodiments in which one or more imaging devices 130e are mounted on a housing 116e of an inventory control system 100e. Inventory control system 100e may be similar and operate using the same principles as those described above. In the present embodiment, one or more extensions 142a, 142b are provided that extend from an upper surface 144 of the inventory control system 100e. In some embodiments, the upper surface 144 may be the same as work surface 106. The extensions 142a, 142b protrude laterally outward from the housing 116e of the inventory control system 100e and provide mounting locations for one or more imaging devices 130e on an underside of the extensions 142. The imaging devices 130e may be fixedly and/or adjustably (such as to adjust a vertical angle of one or more of the imaging devices 130e) mounted on an underside and/or edge of each extension 142a, 142b. The extensions 142a, 142b (and imaging devices 130e mounted thereto) extend over the drawers 104e when one of the drawers 104e is opened, providing the imaging devices 130e line of sight to the open drawer 104e and allowing the contents of the drawer 104e to be imaged. As shown in FIG. 6A, the inventory control system 100e may include two extensions 142a that are spaced apart and positioned on opposite sides of the inventory control system 100e. One or both of the extensions 142a may include one or more imaging devices. The embodiments of FIGS. 6A and 6B are essentially identical, except for extensions 142a and 142b, and thus will use the same reference numerals except for the extensions 142a and 142b. As illustrated in FIG. 6B, the inventory control system 100e may include a single extension 142b positioned centrally along the front of the inventory control system 100e and that includes one or more imaging devices 130e. It will be appreciated that any combination of extensions 142a, 142b and/or imaging devices 130e may be utilized in a particular application. Individual images of the imaging devices 130e may include an entire storage region of each drawer 104e, may be stitched together to form a single image showing the entire storage region and/or may include an entirety of one or more sections of the storage region.

FIGS. 7A-7C illustrate an embodiment of the inventory control system 100f, which may be similar to and operate on the principles of those described above. Inventory control system 100f includes one or more imaging devices 130f mounted on an exterior of each drawer 104f that are capable of imaging the contents of an open drawer 104f positioned below the imaging devices 130f For example, in some embodiments, a front of some or all of the drawers 104f may include a mounting site 146 for one or more imaging devices 130*f*. In some embodiments, the mounting sites 146 may be angled inward and/or downward to direct the imaging devices 130*f* in a direction of where one or more of the lower drawers 104*f* is to be opened. In other embodiments, the mounting sites 146 may be oriented in other directions and the imaging devices 130*f* themselves may be mounted in a manner that allows the imaging devices 130*f* to point toward the location at which the lower drawers 104*f* are to be opened. As illustrated, the mounting sites 146 are directed both downward and inward and house and/or otherwise support two imaging devices 130*f* on either side of the drawer 104*f*. The two imaging devices 130*f* positioned on a same side of the drawer 104*f* are oriented at different angles. As just one example, the innermost imaging device 130*f* is angled inward toward a central portion of the drawer 104*f* while the outermost imaging device 130*f* is angled directly outward along a sliding axis of the drawer 104*f*, although the opposite orientations are possible in some embodiments. Such arrangements of imaging devices provide considerable overlap in field of view to ensure that there is imaging coverage of the entire storage region 136*f*. It will be appreciated that other arrangements of imaging devices 130*f* is possible in some embodiments.

The use of fixed imaging devices 130*f* on each drawer 104*f* allows the imaging devices 130*f* to capture at least a portion of the storage region 136*f* of a lower drawer 104*f* when the lower drawer 104*f* is opened. If only a portion of the storage region 136*f* of the lower drawer 104*f* is detectable using the imaging devices 130*f* on a single drawer 104*f*, images from imaging devices 130*f* of one or more other drawers 104*f* that are positioned above the open lower drawer 104*f* may be used to image the remaining portions of the storage region 136*f*. In some embodiments, the entire storage region 136*f* may be imaged using only imaging devices 130*f* from a single higher-positioned drawer 104*f*. By using a known vertical distance between a given imaging device 130*f* and/or set of imaging devices 130*f* and the opened drawer 104*f*, the inventory control system 100*f* may determine which imaging devices 130*f* are needed to image the storage region 136*f* of the open drawer 104*f*. The inventory control system 100*f* may also determine which of the imaging devices 130*f* is directed at a particular portion of the storage region 136*f* based on these distances and/or the arrangement of imaging devices 130*f* on the various drawers 104*f*.

The width of the field of view of the imaging devices 130*f* may be selected based on a size (area, weight, length, depth, etc.) of each drawer 104*f*, number of imaging devices 130*f*, the orientation of each imaging device 130*f*, the downward angle of the imaging devices 130*f*, and/or other factors. In some embodiments, some or all of the drawers 104*f* may have different depths. In such embodiments, the arrangements of the imaging device may be adjusted to ensure that adequate imaging coverage is provided. While shown here with four imaging devices 130*f* per drawer 104*f*, it will be appreciated that other numbers and arrangements of imaging devices 130*f* are possible. In some embodiments, a bottommost of the drawers 104*f* may have a different design and/or may not include imaging devices 130*f*, as there is no lower drawer 104*f* to be imaged. Individual images captured by the imaging devices 130*f* may include the entire storage region 136*f*, may be stitched together to form a single image showing the entire storage region 136*f* and/or may include an entirety of one or more sections of the storage region 136*f*.

FIGS. 8A and 8B illustrate an embodiment of an inventory control system 100*g*, which may be similar and operating using the principles described in relation to the inventory control systems 100 above. Inventory control system 100*g* may include one or more imaging devices 130*g* positioned at a top of the housing 116*g* of the inventory control system 100*g* and/or additional imaging devices 131*g* positioned on or proximate to edges of some or all of the drawers 104*g*. The imaging devices 131*g* may function similar to those imaging devices 130*f* described in relation to FIGS. 7A and 7B. The imaging device 130*g* positioned on top of the housing 116*g* may be similar to those described in relation to FIGS. 4A-5B. By utilizing a combination of imaging devices 130*g* and 131*g*, the inventory control system 100*g* may be better able to image each of the drawers 104*g* housed therein. For example, when using only imaging devices 130*g* it may be difficult to get sufficient resolution of drawers 104*g* that are positioned far away from the imaging devices 130*g*, such as those drawers 104*g* positioned at a bottom of the inventory control system 100*g*. However, imaging devices 130*g* are able to scan the uppermost drawers 104*g* of the inventory control system 100*g*. Conversely, using only imaging devices 131*g* that are positioned to image drawers 104*g* that are beneath the respective imaging devices 131 may not be able to image one or more drawers 104*g* at the top of the inventory control system 100*g*. For example, the topmost drawer 104*g* of the inventory control system 100*g* will not have a drawer 104*g* positioned above it and may require a different imaging device arrangement. However, all lower drawers 104*g* may have one or more imaging devices 131*g* positioned above. When implemented together, the imaging devices 130*g* and 131*g* enable all drawers 104*g*, including the top and bottom drawers 104*g*, to be imaged. While shown here with two imaging devices 131*g* per drawer 104*g*, it will be appreciated that other numbers and arrangements of imaging devices 131*g* are possible. Individual images captured by the imaging devices 130*g*, 131*g* may include the entire storage region 136*g*, may be stitched together to form a single image showing the entire storage region 136*g* and/or may include an entirety of one or more sections of the storage region 136*g*.

In embodiments, rather than using a combination of different imaging device arrangements to enable the imaging of each drawer 104*g* in a particular inventory control system 100*g*, one or more of the drawers 104*g* may have a different design and/or may be used to store items that are not under inventory control. For example, in a medical setting, tongue depressors, cotton swabs, and the like may be stored in one of the drawers 104*g* to eliminate the need for a certain set of imaging devices 130*g*, 131*g*. In other embodiments, rather than using multiple imaging device arrangements, one or more of the drawers 104*g* may utilize a different type of sensor for inventory control purposes.

Figure 9A:
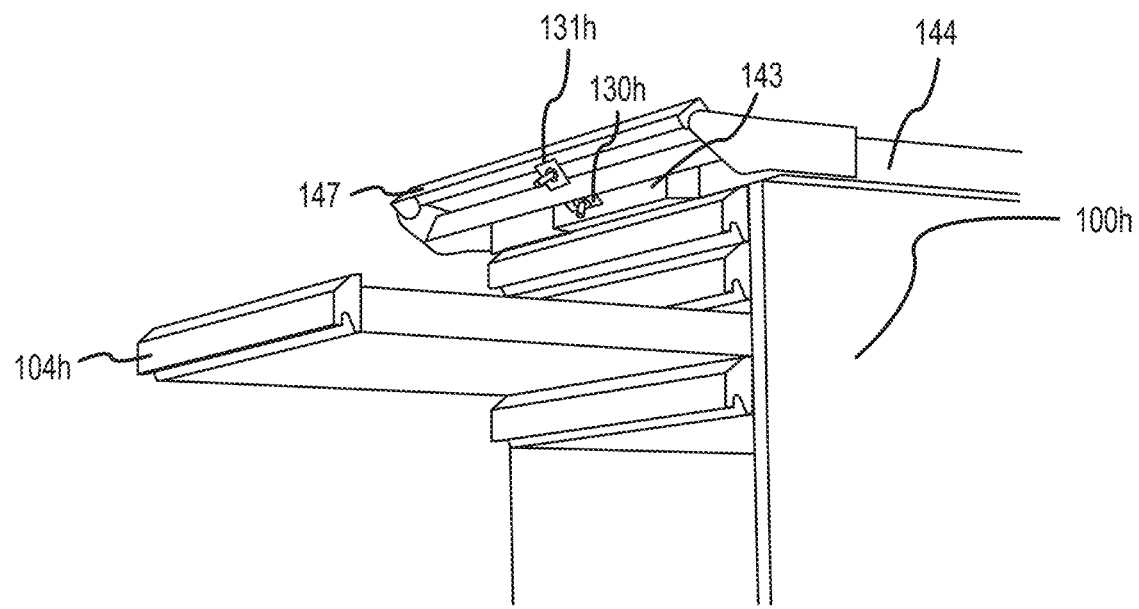
FIG. 9A illustrates an inventory control system having imaging devices positioned on a front of a housing according to embodiments of the present invention.
Figure 9B:
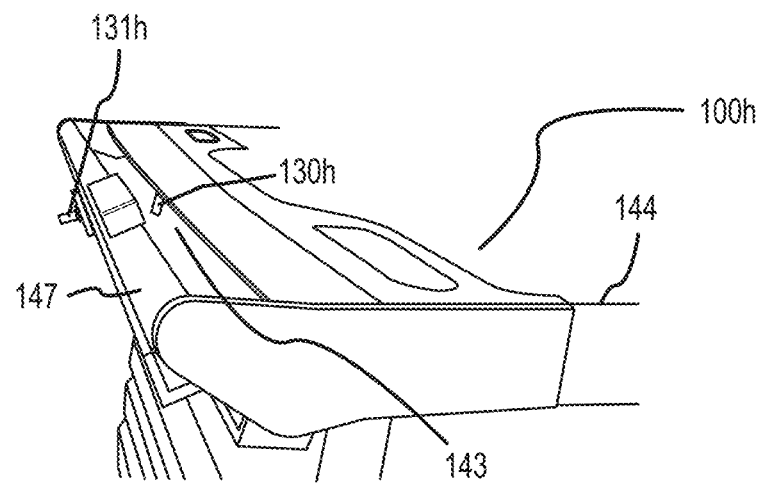
FIG. 9B illustrates an alternative placement of the imaging devices of the inventory control system of FIG. 9A.

FIGS. 9A and 9B illustrate another embodiment of an inventory control system 100*h*, which may be similar to and operate on the principles described in accordance with those above. Inventory control system 100*h* may have one or more imaging devices 130*h* and 131*h* positioned on a housing of the inventory control system 100*h*. A first of the imaging devices 130*h* is positioned on or proximate to a front 143 of an upper surface 144 (such as work surface 106) of the inventory control system 100*h*, while another of the imaging devices 131*h* is positioned on an arm or other extension 147 that is coupled with and/or extends from the upper surface 144. As illustrated, the first imaging device 130*h* is angled generally downward to have a field of view that captures the innermost portion of each drawer 104*h* when the drawer 104*h* is fully opened. The additional imaging device 131*h* is angled down and outward along a sliding axis of the drawer 104*h* and is aimed to have a field of view that captures and outermost portion of each drawer 104*h* when the drawer 104*h* is fully opened. While shown here with two imaging devices 130*h*, 131*h*, it will be appreciated that other numbers and arrangements of imaging devices 130*h*, 131*h* are possible. Individual images captured by the imaging devices 130*h*, 131*h*, may include an entire storage region of drawer 104*h*, may be stitched together to form a single image showing the entire storage region and/or may include an entirety of one or more sections of the storage region.

Figure 10A:
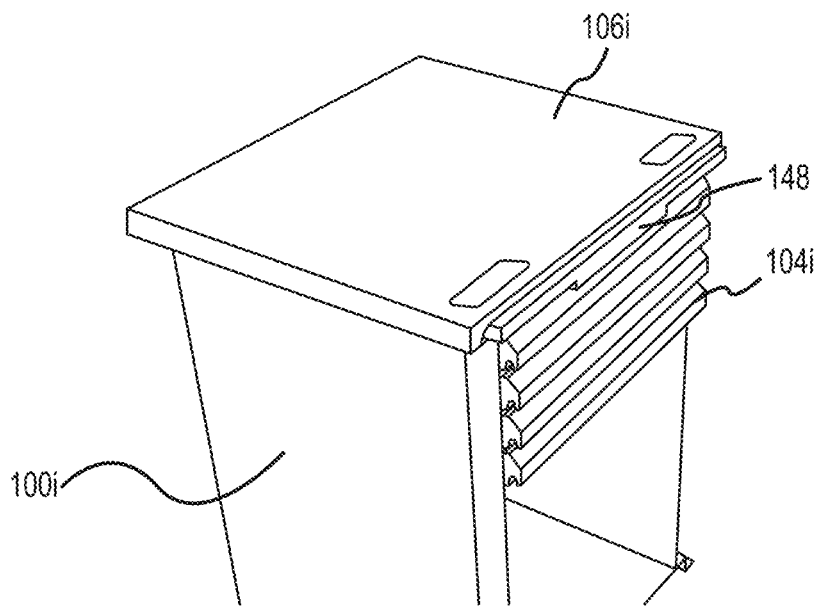
FIG. 10A illustrates a perspective view of an inventory control system having imaging devices mounted on a movable extension according to embodiments of the present invention.
Figure 10B:
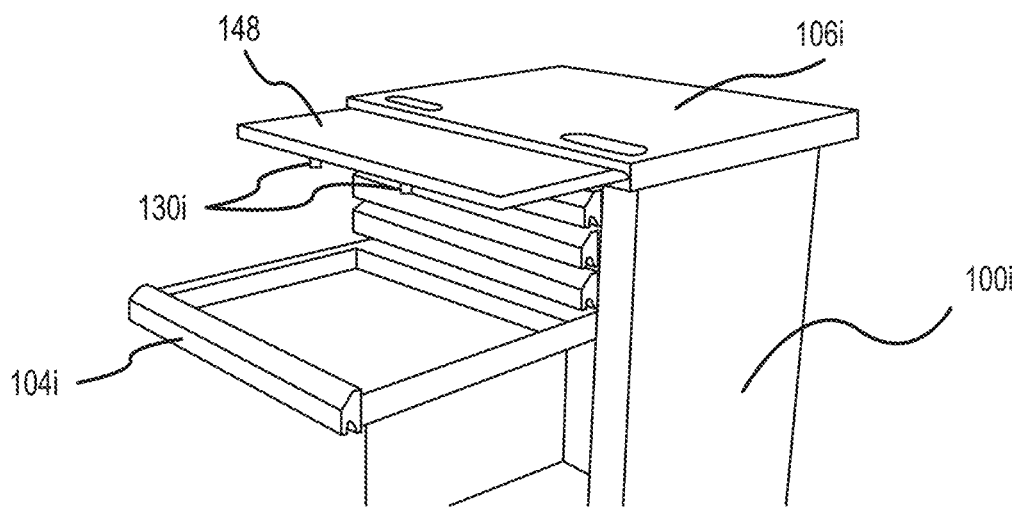
FIG. 10B illustrates a top perspective view of the inventory control system of FIG. 10A with an extension fully extended.
Figure 10C:
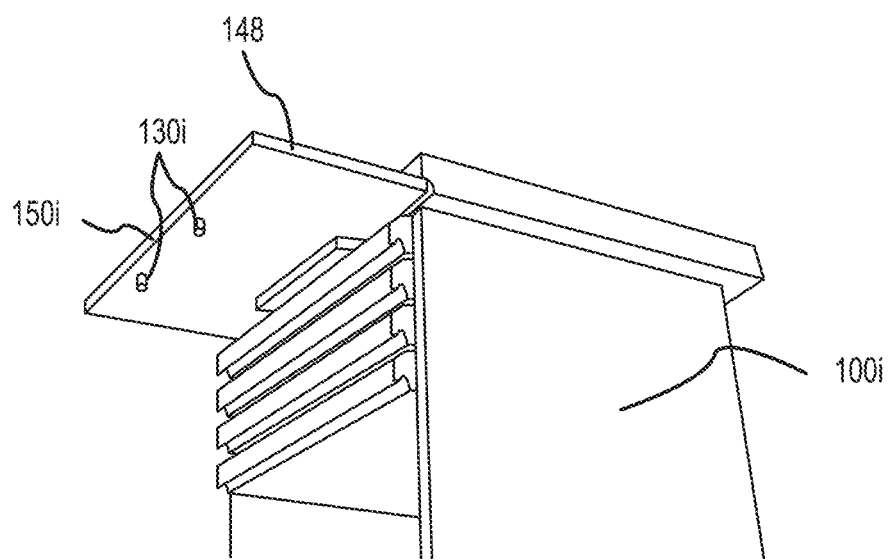
FIG. 10C illustrates a lower perspective view of the inventory control system of FIG. 10A with an extension fully extended.

FIG. 10A-10C illustrate an embodiment of the inventory control system 100*i* that is similar to and operates on similar principles as those described above. Inventory control system 100*i* includes a slide out work surface 148 that may include a number of imaging devices 130*i* incorporated therein to inventory drawers 104*i* positioned below the slide out work surface 148. As illustrated in FIG. 10A, the slide out work surface 148 may be fully stowable within a recess formed within a housing of the inventory control system 100*i* when not in use. When pulled out and/or otherwise extended, the slide out work surface 148 provides a surface on which a user may set items and/or otherwise prepare for a task. In some embodiments, the slide out work surface 148 may be parallel to and/or substantially in line with any existing work surface 106*i* such that the slide out work surface 148 effectively operates as an extension of the work surface 106*i* as best illustrated in FIG. 10B. While shown as sliding out from a recess formed in the housing, it will be appreciated that in some embodiments the slide out work surface 148 may be pivotally coupled upward or downward such that the slide out work surface 148 sits substantially parallel to a front vertical face or horizontal surface of the inventory control system 100*i*. In some embodiments, the slide out work surface 148 may be motorized. In some such embodiments, the slide out work surface 148 may be extended to predetermined intervals based on a height of a drawer 104*i* that is being scanned.

As best illustrated in FIG. 10C, one or more imaging devices 130*i* may be mounted on an underside of the slide out work surface 148. Two imaging devices 130*i* are positioned proximate a distal edge 150*i* of the slide out work surface 148 and are aimed downward to capture images of storage regions of opened drawers 104*i*. It will be appreciated that any number of imaging devices 130*i* (including a single imaging device 130*i*) may be provided on the underside of the slide out work surface 148. Additionally, some or all of the imaging devices 130*i* may be positioned at other locations on the slide out work surface 148. For example, in some embodiments, an array of imaging devices 130*i* may be provided at various positions on the underside of the slide out work surface 148, including positions that are inward from the distal edge 150*i*. The array of imaging devices 130*i* may include any number of imaging devices 130*i* in any arrangement and may be symmetrical or asymmetrical. Individual images captured by the imaging devices 130*i* may include the entire storage region, may be stitched together to form a single image showing the entire storage region and/or may include an entirety of one or more sections of the storage region.

In operation, once a user makes a selection of items, the user may maneuver the slide out work surface 148 into an extended position in which the slide out work surface 148 and imaging devices 130*i* overhang an area in which drawers 104*i* may be opened. In some embodiments, the unlocking of a given drawer 104*i* may be prevented until the slide out work surface 148 is in the extended position such that the maneuvering of the slide out work surface 148 effectively triggers the unlocking of the drawer 104*i*. Such a design ensures that the imaging devices 130*i* are in place to image the contents of the opened drawer 104*i* before the drawer 104*i* is opened and any items are removed. Once the user places the slide out work surface 148 in the extended position, the user may open a drawer 104*i* and remove items. The imaging devices 130*i* may take images of the contents of the drawer 104*i* during this time (before, during, and/or after the user has removed items). The drawer 104*i* may then be closed and if no other drawers 104*i* are accessed, the user may maneuver the slide out work surface 148 back into a stowed position.

Figure 11A:
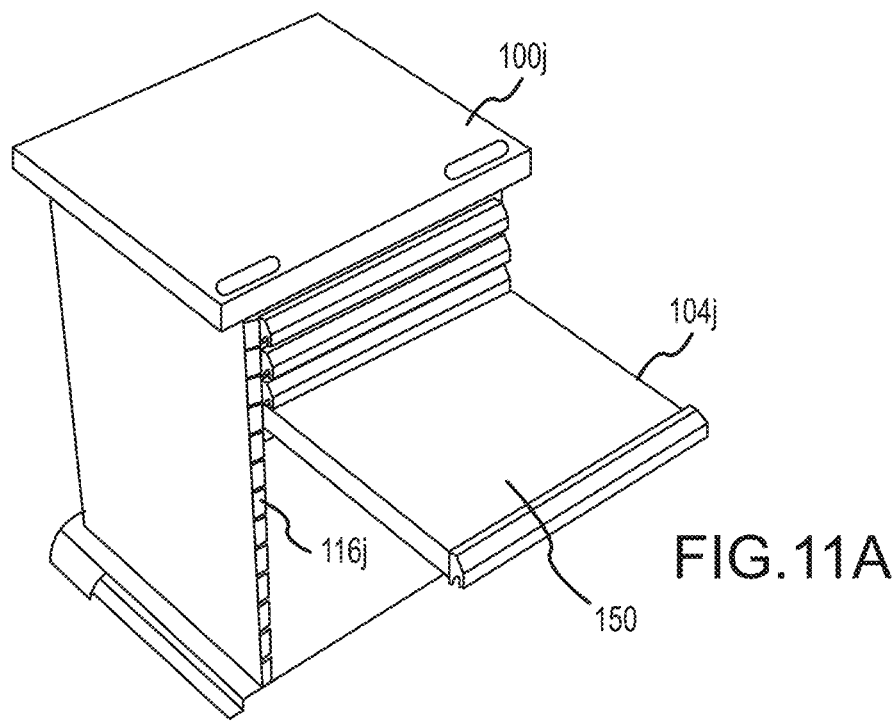
FIG. 11A illustrates an inventory control system having imaging devices positioned on a drawer lid according to embodiments of the present invention.
Figure 11B:
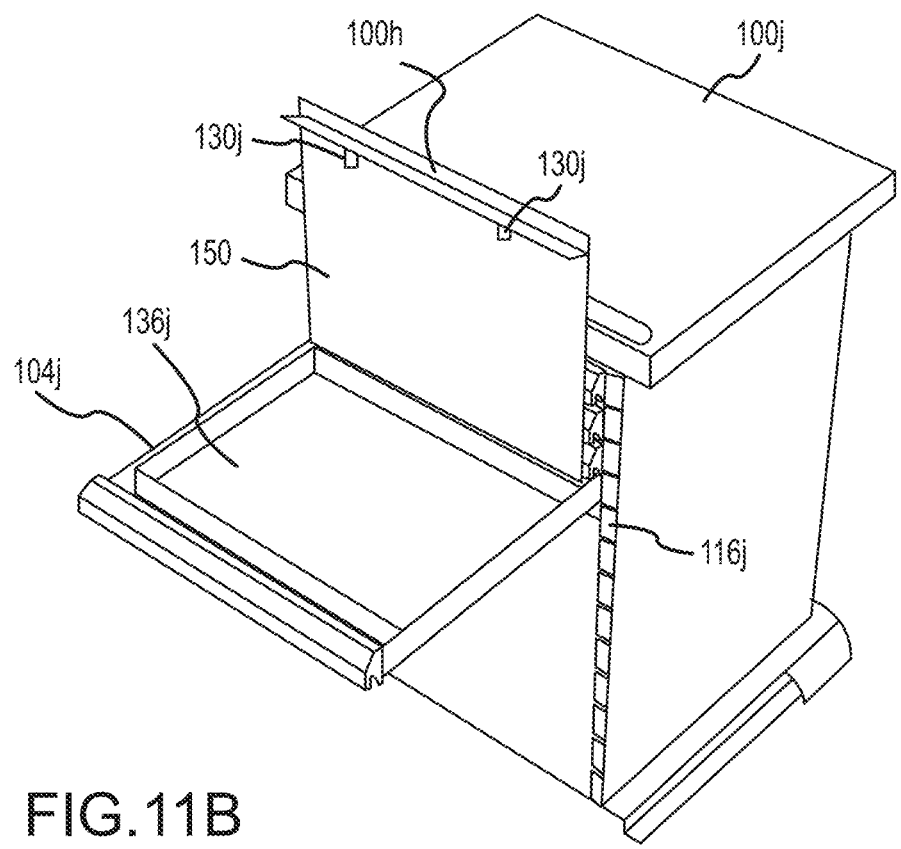
FIG. 11B illustrates the inventory control system of FIG. 11A with the lid in an open position.

FIGS. 11A and 11B illustrate an embodiment of an inventory control system 100*j* that is similar to and operates using similar principles as those described above. Inventory control system 100*j* includes lidded drawers 104*j*. As best illustrated in FIG. 11A, as the drawer 104*j* is drawn out from the housing 116*j* of the inventory control system 100*j*, a lid 150 is positioned over all or a portion of the storage region 136*j* of the drawer 104*j*. In some embodiments, the lid 150 may be transparent to allow users to see the contents of the drawer 104*j* prior to opening the lid 150, while in other embodiments the lid 150 may be opaque. To access the contents of the drawer 104*j*, the user must raise the lid 150 to an access position. In the access position, the lid 150 may be pivoted to an angle relative to the drawer 104*j*. Oftentimes, this angle may be approximately 90 degrees relative to the drawer 104*j*, however other angles are possible. In some embodiments, once the lid 150 is in the access position, one or more imaging devices 130*j* positioned on an underside of the lid 150 will be in an imaging position, with the imaging devices 130*j* being directed downward and forward to image the contents of the open drawer 104*j*. In such embodiments, the lid 150 may optionally include sensors that can detect when the lid 150 has been moved into the imaging position. The aiming of the imaging devices 130*j* may be linked to the position of the lid 150 (either mechanically or via sensors and motors) to increase the angle of lid opening that can acquire useful images. Once the lid 150 is in the imaging position, the imaging devices 130*j* may be activated to monitor the contents of the drawer 104*j*. Once the user has taken the desired items from the drawer 104*j*, the lid 150 may be closed, the imaging devices 130*j* may be deactivated, and the drawer 104*j* may be closed and/or locked. In other embodiments, the imaging devices 130*j* may be in an imaging position (facing an interior of the drawer 104*j*) when the lid 150 is closed. In such embodiments, the lid 150 may optionally include sensors (not shown) that can detect when the lid 150 has been closed. Once the lid 150 is in the closed position, the imaging devices 130*j* may be activated to monitor the contents of the drawer 104*j*.

While illustrated with two imaging devices 130*j* spaced apart from one another along a width of the lid 150, it will be appreciated that any number and/or arrangement of imaging devices 130*j* is possible. Individual images captured by the imaging devices 130*j* may include the entire storage region 136*j*, may be stitched together to form a single image showing the entire storage region 136*j* and/or may include an entirety of one or more sections of the storage region 136*j*.

Figure 12A:
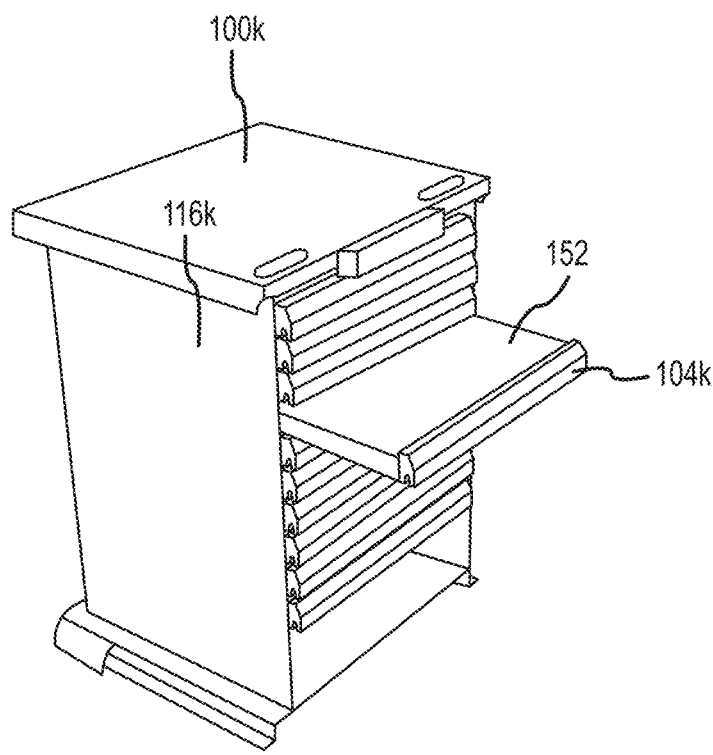
FIG. 12A illustrates an inventory control system having imaging devices positioned on a drawer lid according to embodiments of the present invention.
Figure 12B:
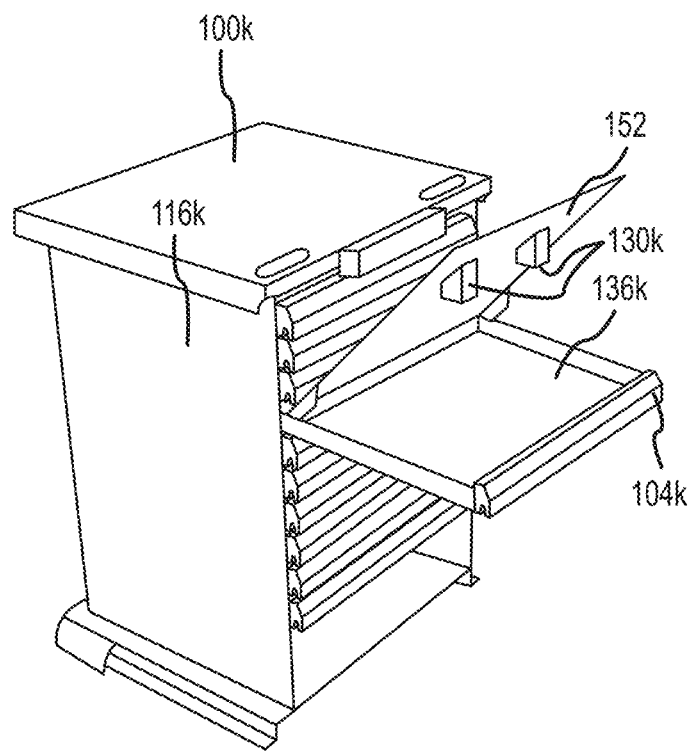
FIG. 12B illustrates the inventory control system of FIG. 12A with the lid in an open position.

FIGS. 12A and 12B illustrate an embodiment of an inventory control system 100*k* that is similar to and operates using similar principles as those described above. Inventory control system 100*k* includes lidded drawers 104*k*. As best illustrated in FIG. 12A, as the drawer 104*k* is drawn out from the housing 116*k* of the inventory control system 100*k*, a lid 152 is positioned over all or a portion of the storage region 136k of the drawer 104k. In some embodiments, the lid 152 may be transparent to allow users to see the contents of the drawer 104k prior to opening the lid 152, while in other embodiments the lid 152 may be opaque. To access the contents of the drawer 104k, the user must raise the lid 152. When open, the lid 152 may be pivoted to an angle relative to the drawer 104k. Oftentimes, this angle may be approximately 45 degrees relative to the drawer 104k, however other angles are possible. Once the lid 152 is in the access position, one or more imaging devices 130k positioned on an underside of the lid 152 will be in an imaging position (or any position capable of capturing the contents of the drawer 104k), with the imaging devices 130k being directed downward to image the contents of the open drawer 104k. In some embodiments, the lid 152 may include sensors that can detect when the lid 152 has been moved into the imaging position. Once the lid 152 is in the imaging position, the imaging devices 130k may be activated to monitor the contents of the drawer 104k. Once the user has taken the desired items from the drawer 104k, the lid 152 may be closed, the imaging devices 130k may be deactivated, and the drawer 104k may be closed and/or locked.

In some embodiments, rather than being actively raised by the user, the lid 152 may be automatically raised to a position that allows imaging of the drawer 104k via the imaging devices 130k as the drawer 104k is drawn out from the housing 116k of the inventory control system 100k. The images may be captured while the lid 152 is stationary and/or while the lid 152 is opening and/or closing. As just one example, the lid 152 may be spring-biased to open to the imaging position when unconstrained. In operation, as the user draws the drawer 104k out of the housing 116k, a spring (not shown) will force the lid 152 upward into the imaging position. Once the user is done accessing items from within the drawer 104k, the user will close the drawer 104k. As the drawer 104k is closed, a top surface of the lid 152 contacts the next drawer 104k up and/or the housing 116k and is forced downward into a closed position. In some embodiments, once the lid 152 is no longer in the imaging position, the imaging devices 130k may be deactivated.

While illustrated with two imaging devices 130k spaced apart from one another along a width of the lid 152, it will be appreciated that any number and/or arrangement of imaging devices 130k is possible. Individual images captured by the imaging devices 130k may include the entire storage region 136k, may be stitched together to form a single image showing the entire storage region 136k and/or may include an entirety of one or more sections of the storage region 136k.

Figure 13A:
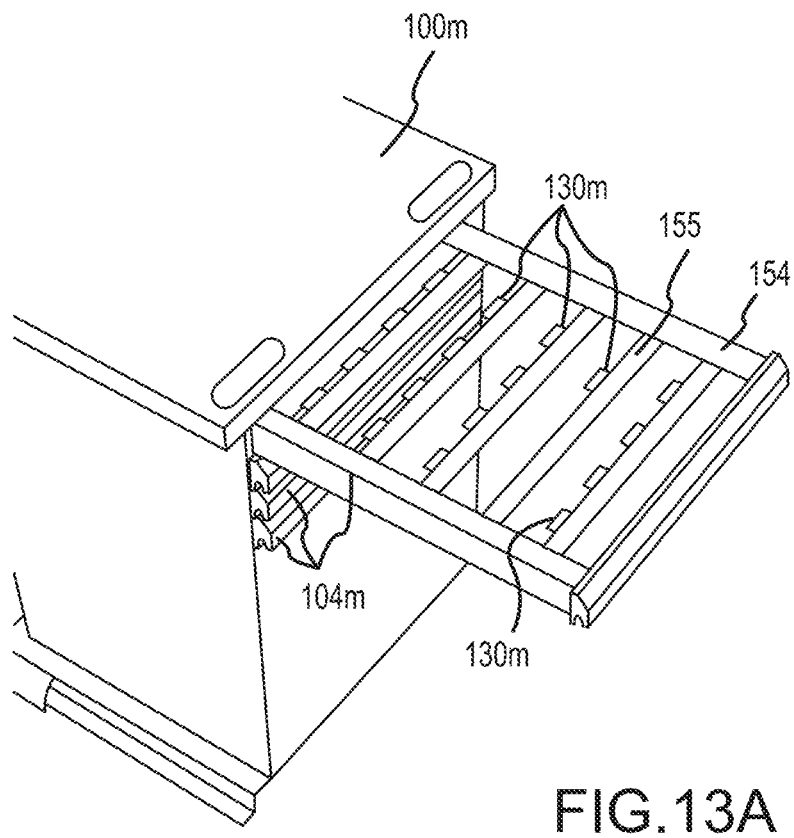
FIG. 13A illustrates a top perspective view of an inventory control system having an array of imaging devices positioned below each drawer according to embodiments of the present invention.
Figure 13B:
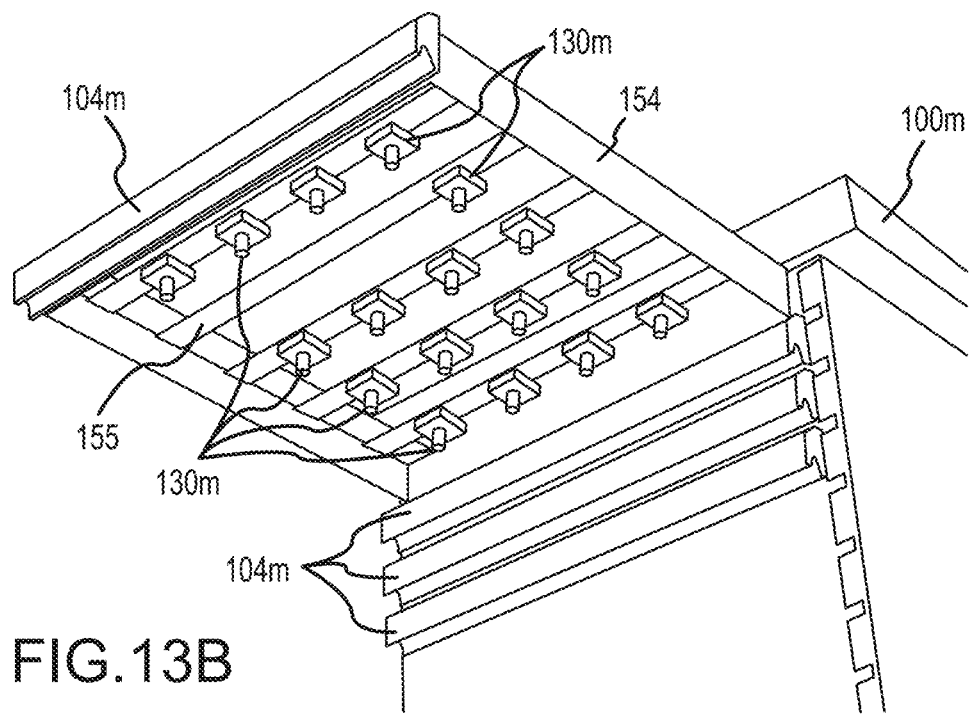
FIG. 13B illustrates a lower perspective view of the inventory control system of FIG. 13A.

In some embodiments, vision scanners (such as imaging devices, IR sensors, and the like) may be configured to monitor the inventory of the inventory control system 100 while a drawer 104 is closed or not fully open. FIGS. 13A-13D illustrate an embodiment of an inventory control system 100m that is configured to image contents of each drawer 104m while the drawers 104m are closed. Inventory control system 100m is similar to and operates using similar principles as those described above. As best illustrated in FIGS. 13A and 13B, a frame 154 that includes an array of imaging devices 130m is positioned above each respective drawer 104m of the inventory control system 100m. The array of imaging devices 130m may be positioned to provide complete imaging coverage of a storage region of a respective one of the drawers 104m. Oftentimes, the imaging devices 130m in the array are positioned at fixed locations that are set to image specific regions of the storage region. In other embodiments, one or more of the imaging devices 130m in the array may be configured to move laterally along one or more axes while the drawer 104m is closed to image different positions of the storage region and to reduce the number of imaging devices 130m needed for each frame 154. While shown here with imaging devices 130m mounted on a number of laterally extending support members 155, it will be appreciated that the imaging devices 130m may be mounted on support members that extend front to back and/or in other orientations. In some embodiments, one or more lighting elements (not shown) will be positioned on the frame 154 and/or within each drawer 104m. The lighting elements are used to provide additional light for the imaging devices 130m to image the interior contents of the drawer 104m while the drawers 104m are closed.

Figure 13C:
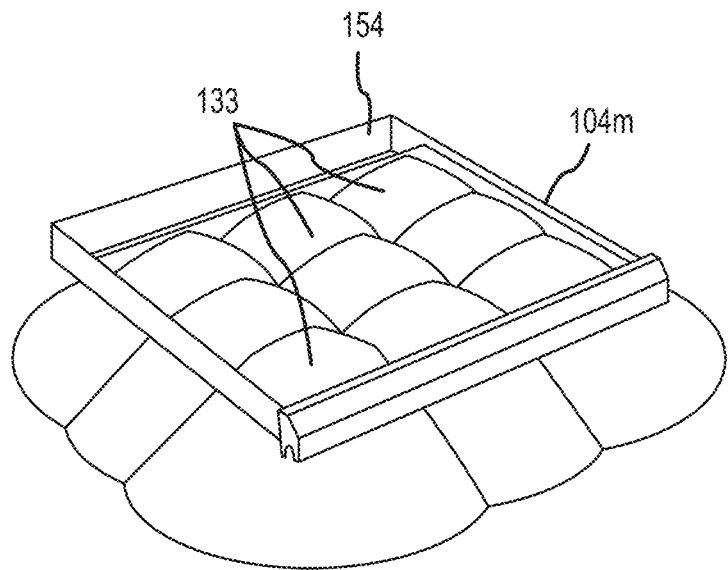
FIG. 13C illustrates overlapping image fields from the array of imaging devices of FIG. 13A.
Figure 13D:
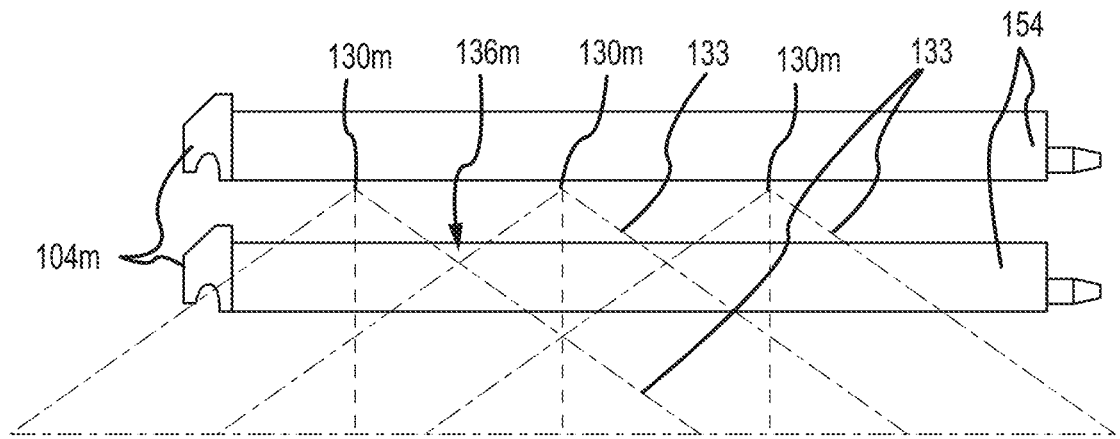
FIG. 13D illustrates drawer spacing of the inventory control system of FIG. 13A.

FIGS. 13C and 13D illustrate the imaging capabilities of an array of imaging devices 130m. As shown in FIG. 13C, image fields 133 of the imaging devices 130m shown in FIGS. 13A and 13B have some overlap with image fields 133 with one another and provide coverage of an entirety of the storage region of each drawer 104m. As illustrated in FIG. 13D, the number of imaging devices 130m needed in the array may be based on a surface area of the drawer 104m, a depth of the drawer 104m and/or vertical distance between the imaging devices 130m and the base of the drawer 104m, a field of view of the imaging devices 130m, and/or other factors. In some embodiments, the drawers 104m may be spaced apart from one another in a vertical direction, oftentimes by a small distance. This provides additional space to house the array of imaging devices 130m between each drawer 104m, as well as increases the vertical distance between the imaging devices 130m and the drawer 104m below. This increased distance enables fewer imaging devices 130m to be used and/or imaging devices 130m with smaller fields of view to be used.

In some embodiments, each frame 154 may be formed into a housing (such as housing 116) of the inventory control system 100m. In other embodiments, each frame 154 may be slidably mounted to the housing such that the frame 154 can be drawn out of the housing, such as for replacement, repair, and/or adjustment of one of more of the imaging devices 130m and/or lighting elements. In other embodiments, some or all of the frames 154 may be formed into a bottom surface of one of the drawers 104m, such that each drawer 104m is imaged by imaging devices 130m mounted on a frame 154 of the drawer 104m above. Oftentimes, in such a configuration, the topmost frame 154 may be mounted to the housing to provide imaging devices 130m for imaging the topmost drawer 104m. Similarly, the bottommost drawer 104m may not include a frame 154 and/or imaging devices 130m as such features are not necessary on the bottommost drawer 104m. Individual images of the imaging devices 130m may include an entire storage region of the drawer 104m, may be stitched together to form a single image showing the entire storage region and/or may include an entirety of one or more sections of the storage region.

Figure 14A:
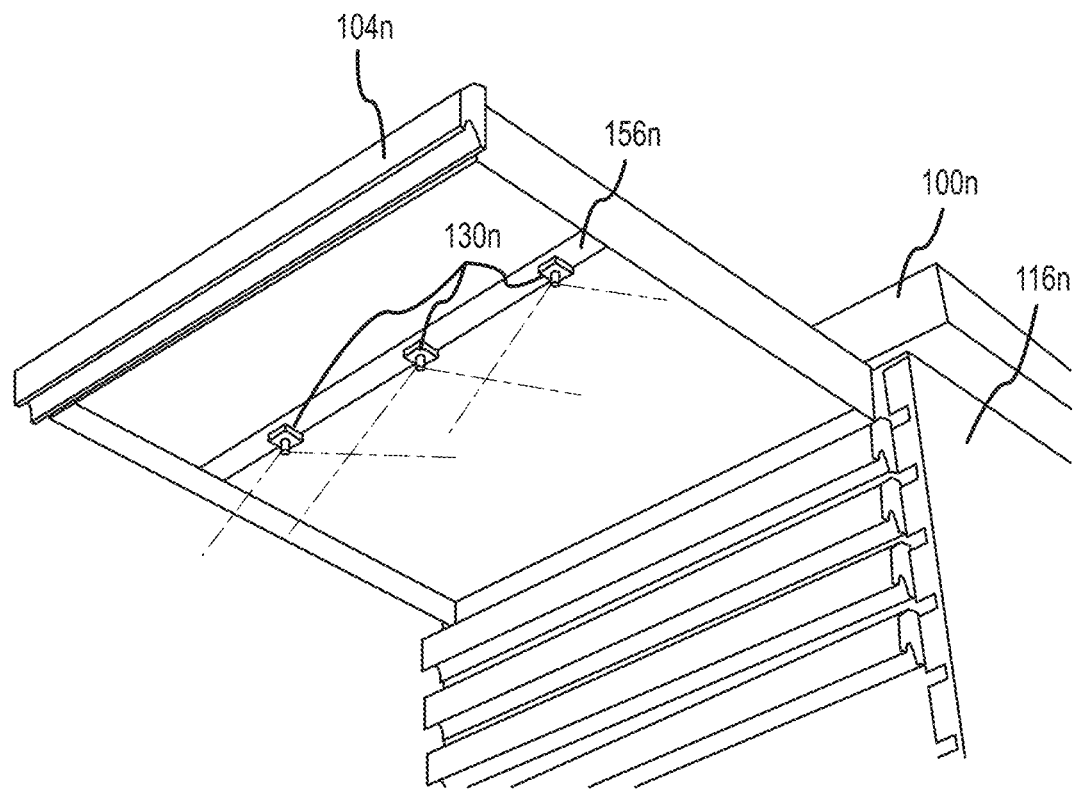
FIG. 14A illustrates an inventory control system having a line scanning device according to embodiments of the present invention.
Figure 14B:
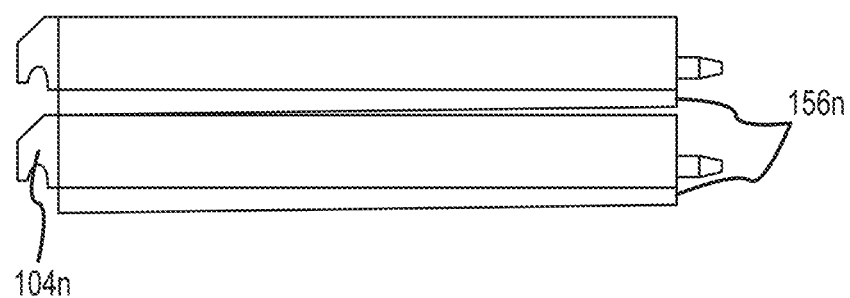
FIG. 14B illustrates drawer spacing of the inventory control system of FIG. 14A.

FIGS. 14A and 14B illustrate an inventory control system 100n that is similar to and operates using similar principles as those described above. Inventory control system 100n utilizes one or more line scanners 156n to image the contents of each drawer 104n. In some embodiments, each line scanner 156n may be movable along a length or width of the drawer 104n to image the contents of the drawer 104n. For example, the line scanner 156n may include one or more imaging devices 130n and/or other image sensors that are positioned on a track for translation along one or more axes of the drawer 104n. In other embodiments, the line scanners 156*n* may be at fixed locations such that as each drawer 104*n* is opened, images are taken of different segments of the drawer 104*n* from the front to the back to get a complete image of a storage region of each drawer 104*n*. In other embodiments, the line scanners 156*n* may be at fixed locations such that as each drawer 104*n* is closed, images are taken of different segments of the drawer 104*n* from the back to the front to get a complete image of the storage region. In embodiments where the line scanner 156*n* is at a fixed location, the line scanner 156*n* may be positioned at a front distal end of the drawer 104*n* and/or housing 116*n* such that an entirely of the storage region of a lower-positioned drawer 104*n* must pass below the line scanner 156*n*.

In some embodiments, each line scanner 156*n* may be formed into the housing 116*n* of the inventory control system 100*n*. In other embodiments, each line scanner 156*n* may be slidably mounted to the housing 116*n* such that the line scanner 156*n* can be drawn out of the housing 116*n*, such as for replacement, repair, and/or adjustment of one of more of the imaging devices 130*n* and/or lighting elements. In other embodiments, some or all of the line scanner 156*n* may be formed into a bottom surface of one of the drawers 104*n*, such that each drawer 104*n* is imaged by a line scanner 156*n* mounted on a drawer 104*n* above. Oftentimes, in such a configuration, the topmost line scanner 156*n* may be mounted to the housing 116*n* to provide imaging devices 130*n* for imaging the topmost drawer 104*n*. Similarly, the bottommost drawer 104*n* may not include line scanner 156*n* as such features are not necessary on the bottommost drawer 104*n*.

Figure 14C:
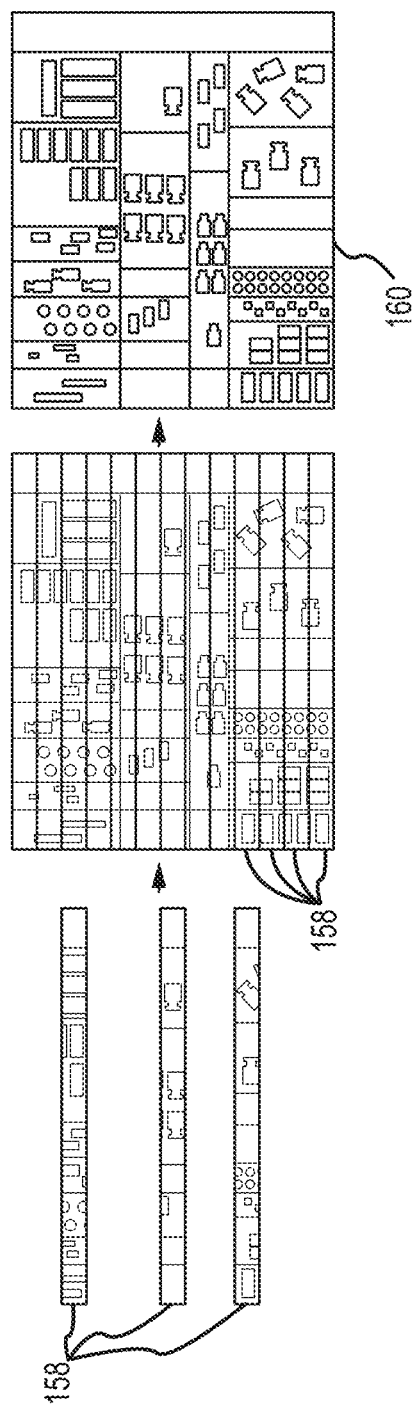
FIG. 14C illustrates an image generated by the inventory control system of FIG. 14A.

In some embodiments, the imaging devices 130*n* may include one or more charge coupled devices (CCDs), complementary metal oxide semiconductor (CMOS) sensors, time delay integration (CCD) sensors, and/or other imaging sensors that are capable of producing clear images of moving objects and/or objects during movement of the imaging devices 130*n*. These imaging devices 130*n* may be used in conjunction with a clock or other timing mechanism to image strips 158 or thin segments of the storage region of a drawer 104*n* as illustrated in FIG. 14C. These image strips 158 may be pieced together for forming a composite image 160 showing a seamless view of the entire storage region of the drawer 104*n*. For example, each image strip 158 may be associated with a timestamp and may cover a particular area of the storage region. A computing device (such as computing device 112) of the inventory control system 100*n* may take the timestamp of each image strip 158, the area of the image strip 158, known dimensions of the drawer 104*n* (or just the storage region), a rate of speed of opening or closing the drawer 104*n*, a rate of movement of the line scanner 156*n*, and/or other information to arrange the image strips 158 into the composite image 160. Any seams and/or overlap in the image strips 158 may be removed in the composite image 160.

Figure 15A:
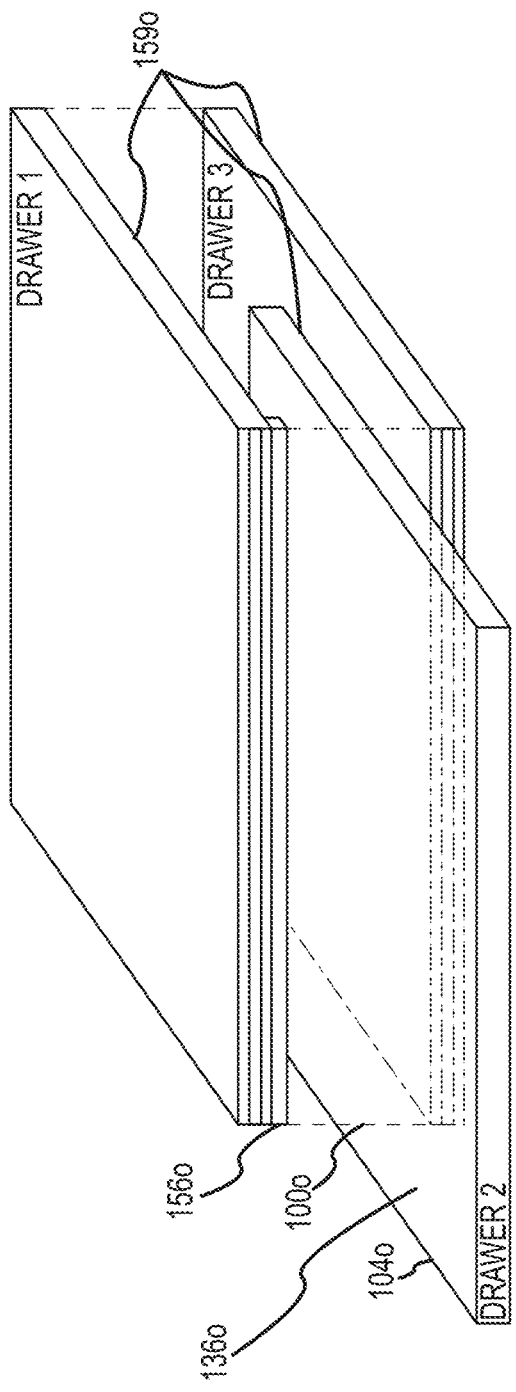
FIG. 15A illustrates an inventory control system having a line scanning device according to embodiments of the present invention.
Figure 15C:
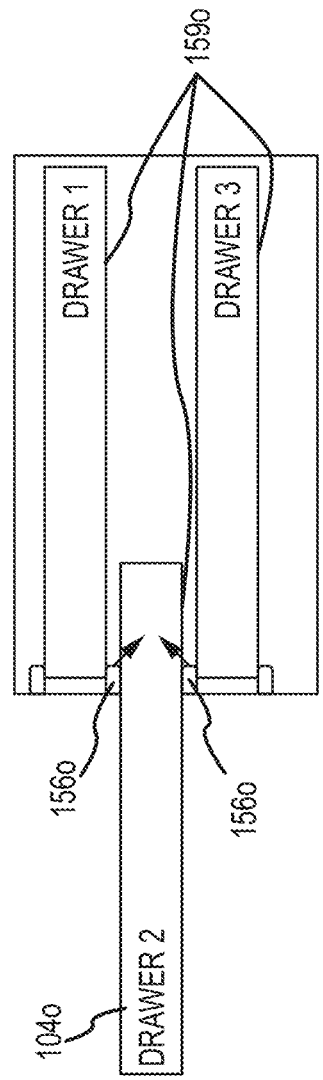
FIG. 15C illustrates a side elevation view of the inventory control system of FIG. 15A with one of the drawers in an open position.
Figure 15B:
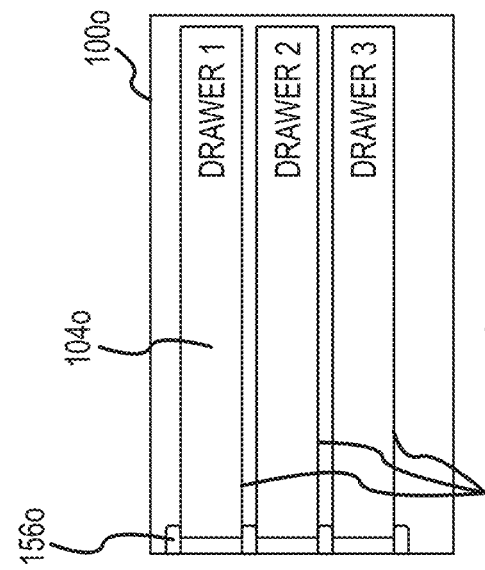
FIG. 15B illustrates a side elevation view of the inventory control system of FIG. 15A with the drawers in a closed position.

FIGS. 15A-15C illustrate another embodiment of inventory control system 100*o* that is similar to and operates using similar principles as those described above. Inventory control system 100*o* utilizes line scanners 156*o*. Each drawer 104*o* includes a transparent bottom surface 159*o*. Line scanners 156*o* are positioned above and below each drawer 104*o*. As a drawer 104*o* is drawn out of a housing of the inventory control system 100*o*, the line scanners 156*o* above and below the drawer 104*o* scan the contents of the drawer 104*o* from both the top and the bottom sides of the drawer 104*o*. For example, the line scanners 156*o* may scan the portion of the drawer 104*o* that is proximate to the front end of the housing, but that is not yet exposed to the user. The contents of the drawer 104*o* may be scanned in a similar manner as the drawer 104*o* is pushed back or otherwise moved into the housing. The primary difference between the embodiment of scanning in FIGS. 15A-15C and that described in relation to FIGS. 14A and 14B is that the embodiment of FIGS. 15A-15C scans the drawers 104*o* using line scanners 156*o* for each drawer 104*o*, and these scanners scan only a portion of the unexposed drawer 104*o* (i.e., the portion that is still inaccessible to a user). This determines the starting "available" list. Once a user has viewed the contents of the drawer 104*o* and determined which items to select (or not) and has completed the task of picking (or not), the drawer 104*o* can be pushed back. During push back, the scanners 156*o* inside the drawer 104*o* are able to re-scan the drawer 104*o* to determine the new "available" list. By comparing the starting available list and the ending available list, the system is able to determine which items have been removed. Discrepancies in item counts may be used to determine which items have been removed from the drawer 104*o*. For example, if there were six vials of a particular medication during the opening scan and four vials remaining during the closing scan, the inventory control system 100*o* may determine that the user removed two vials of the medication.

In some embodiments, the line scanners 156*o* may only scan the drawer 104*o* during one of opening or closing. For example, the line scanners 156*o* may only image the drawer 104*o* when the drawer 104*o* is being pushed back and/or otherwise closed. In such embodiments, the inventory control system 100*o* may use the difference in item counts from the previous push back count and the current push back count to determine which items were taken from the drawer 104*o* while it was open.

In operation, the inventory control system 100*o* derives an inventory from the last push back scan on record. This may be done, for example, using computing device 112 or other processor. The user may then access the drawer 104*o* and remove any items needed. As the user pushes the drawer 104*o* back in, the line scanners 156*o* above and below the drawer 104*o* scan sections of a storage region of each drawer 104*o*, which are used to generate a composite image of the storage region. The inventory control system 100*o* may then analyze the composite image to generate a new inventory. Any items that have different counts from the two push back scans may be determined to have been taken by the user during the last access of the drawer 104*o*. The inventory control system 100*o* as embodied in FIGS. 15A-15C shows the presence of dual scanners 156*o*. In this embodiment, each of the drawers 104*o* are considered to be have a fully or partially transparent bottom surface. The ability of the dual scan is most advantageous when the contents of the drawer 104*o* are more visible when viewed from one direction than when viewed from the other. The inventory control system 100*o* uses identification algorithms that determine the portions of particular scans that are to be used for determining the actual content/inventory of the drawer 104*o*. A secondary advantage of the embodied inventory control system 100*o* is that each of the scanners 156*o* is shared by two drawers 104*o* (except the scanner 156*o* on the top side of the topmost drawer 104*o* and the scanner 156*o* on the bottom side of the bottommost drawer 104*o*). The transparency of the drawer 104*o* may be selected based on the wavelength of the light from the scanner 156*o*.

FIGS. 16A-16C illustrate an embodiment of an inventory control system 100*p* that is similar to and operates using similar principles as those described above. Inventory control system 100*p* includes a single set of imaging sensors 160

(such as line scanners 156 and/or other imaging devices 130). As illustrated, the imaging sensors 160 are positioned on an extension 162 that protrudes forward from a housing of the inventory control system 100*p* at a height that is lower than a bottommost drawer 104*p* that is to be automatically inventoried. For example, as illustrated, the extension 162 is positioned below the bottommost drawer 104*p*, however in other embodiments the extension 162 may be positioned higher on the inventory control system 100*p* (or multiple extensions 162 and sets of imaging sensors 160) and may be used to scan drawers 104*p* at various positions on the inventory control system 100*p*. Each drawer 104*p* includes a fully or partially transparent bottom 159*p*. The imaging sensors 160 may be positioned on a topside of the extension 162 and may be aimed upward such that as a drawer 104*p* is pulled out, the imaging sensors 160 are aimed at an underside of the drawer 104*p*. Such positioning enables the use of a single set of imaging sensors 160 to be used to scan the contents of any drawer 104*p* of the inventory control system 100*p* through the transparent bottom of the drawer 104*p*.

It will be appreciated that numerous other techniques for imaging the contents of drawers, such as drawers 104, while the drawers are in a closed or partially closed state are possible. Several of these techniques may involve the use of a single imaging device, such as imaging devices 130 and/or 160 (although any of these techniques may be adapted to utilize multiple imaging devices). For example, some embodiments utilize a one or more mirrors to enable a single imaging device to capture images of the entire storage area of a given drawer. In some embodiments, an imaging device may be directed at a mirror. The mirror may be configured to rotate and/or otherwise move, thereby altering the image field captured by the imaging device by reflecting a different segment of the storage region into the imaging device's lens. The mirror may be positioned on a side of the drawer opposite of the imaging device, enabling the imaging device to image objects that are distant from the imaging device. Images from the imaging device with the mirror at different angles may be combined to form a composite image showing the entire contents of the storage region. In some embodiments, the imaging device may include a TDI sensor that is able to create a smooth image of the contents of the drawer as the mirror is rotated.

In other embodiments, a stationary mirror may be used with a rotatable and/or otherwise movable imaging device, such as image devices 130 and/or 160. The imaging device may be moved or rotated about the interior of a drawer, such as one of drawers 104, to capture different segments of the storage region as reflected in the mirror. In yet other embodiments, both a mirror and an imaging device may be fixed on a frame or on an underside of the drawer above. The imaging device may be focused on the mirror, which may be angled so as to reflect a view of what is below the mirror. As a drawer is opened and/or closed, the fixed imaging device may capture images the contents of the drawer as reflected by the mirror. In other embodiments, rather than angling the mirror, the mirror may be vertically oriented and the imaging device may be angled downward and/or both the imaging device and the mirror may be angled relative to the drawer.

Figure 17:
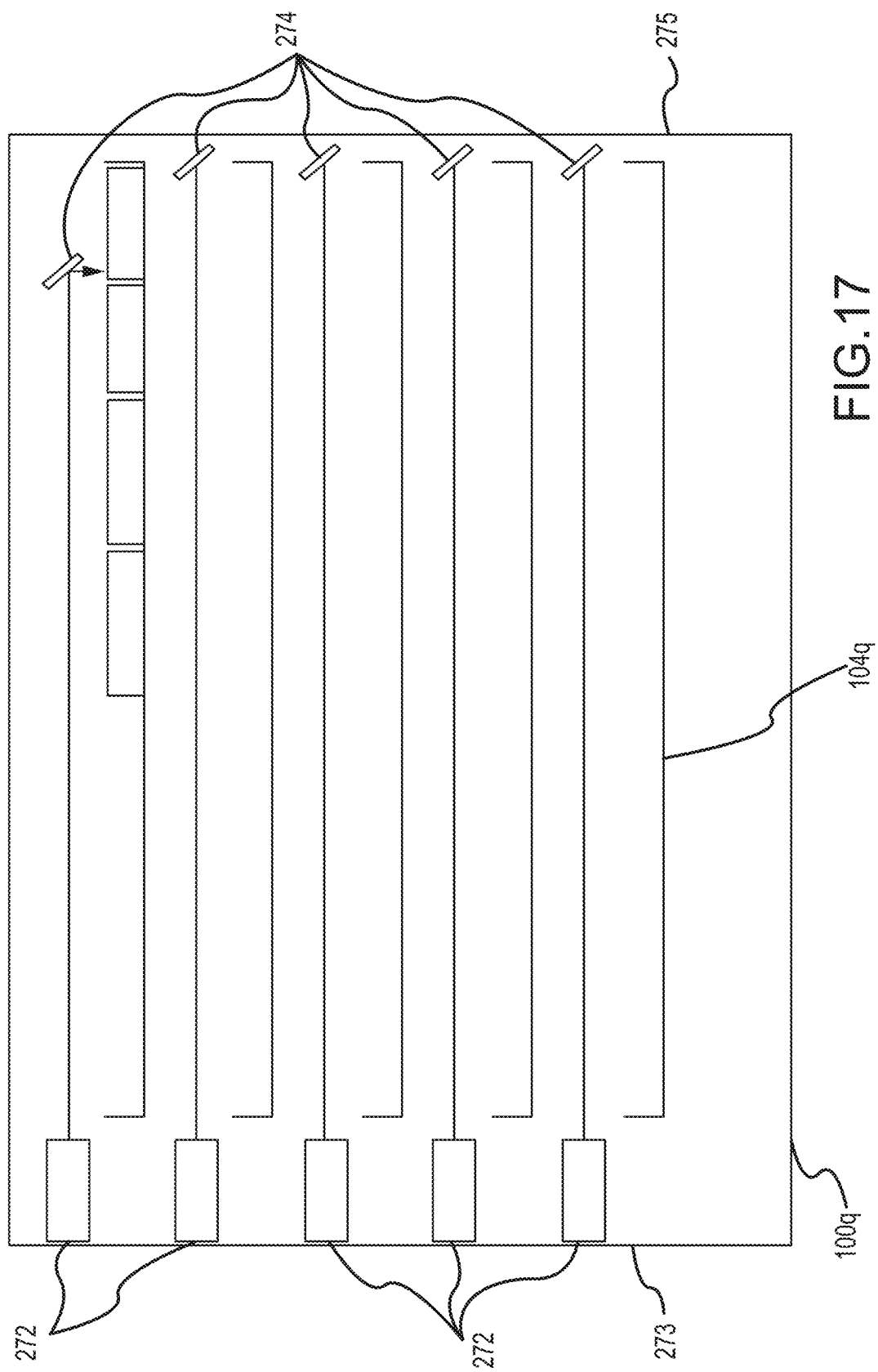
FIG. 17 illustrates an embodiment of an inventory control system that includes a dedicated imaging device and movable mirror for each drawer according to embodiments of the present invention.

In another embodiment, an inventory control system 100*q* may include drawers 104*q* that are each associated with a dedicated imaging device 272 as illustrated in FIG. 17. The imaging device 272 (such as a camera or line scanner) may be positioned within a rear 273 of the housing of the inventory control system 100*q* and may be aimed toward a front 275 of the housing of the inventory control system 100*q*. Each drawer 104*q* may include a mirror 274 that is translatable along a length of the drawer 104*q* (and the imaging axis of the imaging device 272) such that as the mirror 274 moves, the imaging device 272 is able to image the contents of the entire drawer 104*q*. In some embodiments, only a single one of the imaging devices 272 may image the contents of a drawer 104*q* at a given time, while in other embodiments multiple imaging devices 272 may image contents of the drawers 104*q* simultaneously.

Figure 18:
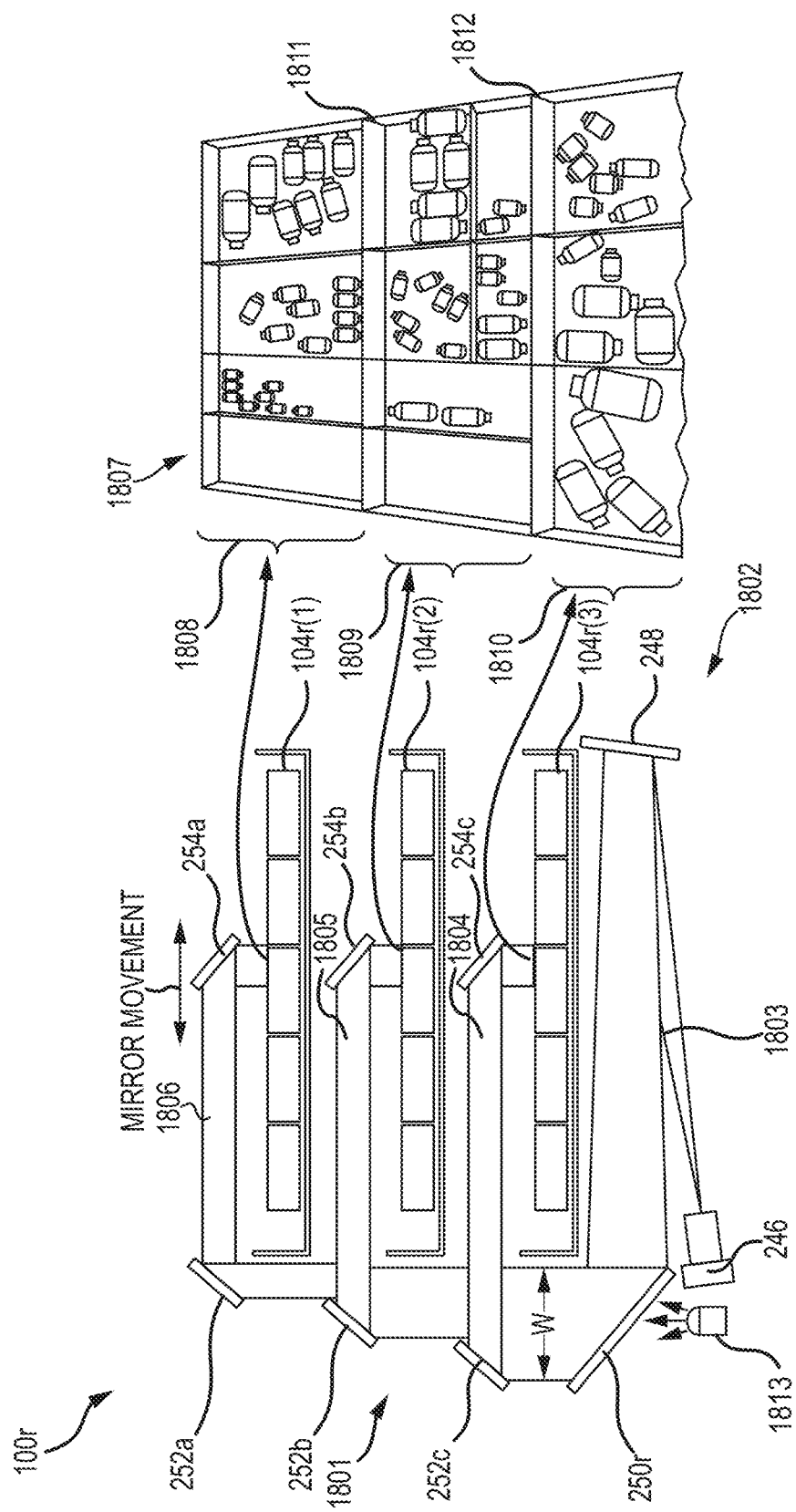
FIG. 18 illustrates an embodiment of an inventory control system that includes an area imaging device and moving mirrors to image contents of drawers according to an embodiment of the present invention.

FIG. 18 illustrates one embodiment of an inventory control system 100*r* that is similar to and operates using similar principles as those described above. Inventory control system 100*r* utilizes an area imaging device 246 to image contents of one or more drawers 104*r* while each of the drawers 104*r* is in a closed position. In FIG. 18, three drawers 104*r* are shown, a top drawer 104*r*(1), middle drawer 104*r*(2), and a bottom drawer 104*r*(3), although it will be recognized that more or fewer drawers 104*r* may be present. The height, width or the depth of the drawers 104*r* need not always be the same and may vary based on parameters such as user preference, sizes of the items to be stored within the drawer 104*r* and the quantities of the items to be stored within the drawer 104*r*.

In the embodiment of FIG. 18, the area imaging device 246 is positioned beneath the drawers 104*r* and a series of mirrors is used to reflect images of the interior of each drawer 104*r* to the area imaging device 246. The area imaging device 246 is preferably a color imaging device, so that items in the drawers 104*r* can be imaged in color, but this is not a requirement. In other embodiments, a monochrome imaging device may be used.

As just one example, the area imaging device 246 may be positioned near a rear of the drawers 104*r* and may be directed toward a front 1802 of the inventory control system 100*r*. Two fixed mirrors 248 and 250*r* may be used to direct reflections into the area imaging device 246. A series of staggered mirrors 252 may be included, with one of the mirrors 252 positioned just above a top surface of a respective one of the drawers 104*r*. In FIG. 18, the mirror 252*a* corresponds to the top drawer 104*r*(1), the mirror 252*b* corresponds to the middle drawer 104*r*(2), and the mirror 252*c* corresponds to the bottom drawer 104*r*(3). More or fewer staggered mirrors 252 may be present, in accordance with the number of drawers 104*r*.

The area imaging device 246 has a field of view 1803, determined in part by the size of the sensor used in the imaging device 246 and the focal length of a lens used in the imaging device 246. The field of view 1803 is redirected by the mirrors 248 and 250*r* toward the staggered mirrors 252. Because the area "seen" by the imaging device 246 grows with the distance from the area imaging device 246, the field of view 1803 has a substantial width W by the time it reaches the first staggered mirror 252*c*. The field of view grows in the direction perpendicular to the view of FIG. 18 as well. The first staggered mirror 252*c* is smaller than the width W of the field of view 1803, so only a first portion 1804 of the field of view 1803 is redirected by the first staggered mirror 252*c*. Similarly, a second portion 1805 of the field of view 1803 is redirected by the second staggered mirror 252*b*, and a third portion 1806 of the field of view 1803 is redirected by the third staggered mirror 252*c*.

The redirected portions 1804, 1805, 1806 are directed to respective movable mirrors 254*a*, 254*b*, and 254*c*, which in turn redirect the imaging device view downwards into the respective drawer 104*r*. In this way, the area imaging device 246 can image portions of the contents of some or all of the drawers 104*r* simultaneously.

The movable mirrors 254 can scan across the drawers 104r from front to back or back to front, while the area imaging device 246 records video or takes images. Thus, the entire contents of the drawers 104r can be scanned.

Also shown in FIG. 18 is a single image or video frame 1807, as may be taken during scanning. A first portion 1808 of the image 1807 corresponds to the portion of the top drawer 104r(1) encompassed by the field of view portion 1806. A second portion 1809 of the image 1807 corresponds to the portion of the middle drawer 104r(2) encompassed by the field of view portion 1805. A third portion 1810 of the image 1807 corresponds to the portion of bottom drawer 104r(3) encompassed by the field of view portion 1804. Darkened borders 1811 and 1812 between the portions of the image 1807 may be formed because the staggered mirrors 252 do not cover the entire field of view 1803 of the imaging device 246. The blackened borders may be helpful in identifying the image portions during later image processing. The borders 1811 and 1812 may be formed in other ways as well. For example, the staggered mirrors 252 may have non-reflective portions near their edges to reduce reflection of light from the drawers 104r to imaging device 246 in those areas. Or field stops may be provided near the staggered mirrors 252 or elsewhere in the cabinet of the inventory control system 100r to block transmission of light. In other embodiments, the borders 1811 and 1812 may be other than black.

The image 1807 is shown as exhibiting keystone distortion. That is, items in the top drawer 104r(1) are shown in the portion 1808 as being narrower than items in the bottom drawer 104r(3) shown in the portion 1810. (The actual full image 1807 will most likely be rectangular, but portions of the image outside of the drawers have been removed in FIG. 18.) This is because the working distance from the area imaging device 246 to the top drawer 104r(1) is longer than the working distance from the area imaging device 246 to the bottom drawer 104r(3), as traced through the various mirrors in the system. Similarly, the working distance from the area imaging device 246 to the front portion of any of the drawers 104r is longer than the working distance from the area imaging device 246 to the rear of the same drawer 104r. Thus, an image taken at the front of any drawer will show items in the drawer 104r as being smaller than in an image taken at the back of the same drawer 104r.

Because the drawers 104r of the inventory control system 100r are preferably closed during scanning, it may be necessary to provide illumination to the drawers 104r so that they can be imaged by the area imaging device 246. Illumination may be provided in any suitable way. For example, each of the movable mirrors 254 may also carry a strip light source that directs light downward into its respective drawer. In another embodiment, the mirror 250r may be only partially silvered, so that some light can be transmitted through it. A sufficiently bright light source 1813 placed under the mirror 250r can direct light upward through mirror 250r, to be reflected from the staggered mirrors 252 and the movable mirrors 254 to illuminate the interiors of the drawers 104r. In this case, the transmittance of the mirror may be selected based on the brightness of the available light, the desired scanning speed, the sensitivity of area imaging device 246 to light, and on other factors. In other embodiments, the light source 1813 can also be next to the mirror 250r, which eliminates the need for a beam splitter and may provide greater illumination than the illustrated placement of light source 1813.

Preferably any light source used is a white light source, so that color imaging of the interiors of the drawers 104r is enabled, but this is not a requirement. In some embodiments, monochromatic light may be used, or even light outside of the visible spectrum, for example infrared light.

Once a sufficient number of images or video frames have been collected to cover the desired portions of the drawers 104r (typically the entire drawers), the image data may be post-processed to reconstruct a complete image of the drawer contents. In other embodiments, image reconstruction may be performed during scanning. While the arrangements of FIG. 18 illustrate the positioning of the area imaging device 246 at the base of the inventory control system 100r, along with specific orientation of mirrors 252a-252c, 250r and 248, it may be construed that such relative positioning may be considered as being determined based on the ability to position the area imaging device 246 within the inventory control system 100r. In other embodiments, where the area imaging device 246 is positioned at the top portion of another embodiment of an inventory control system, the angles of orientation and/or tilt of the mirrors 252a-252c, 250r and 248 may be appropriately altered to allow proper imaging of the contents of the drawers. Other embodiments may also include positioning of the area imaging device 246 towards the rear-center position of the inventory control system or the top-front position of the inventory control system. Such modifications may be construed as being within scope of the present invention.

Figure 19:
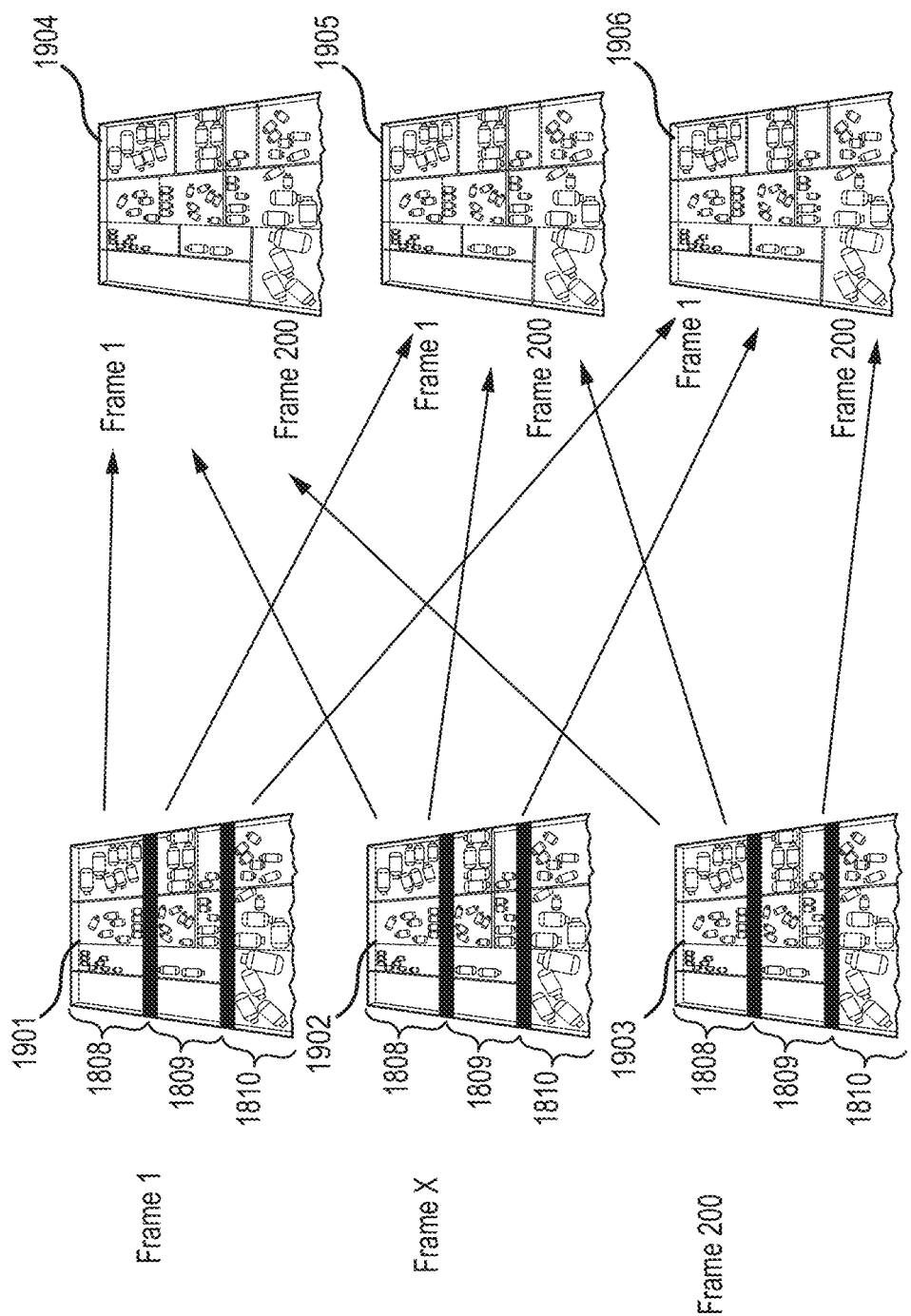
FIG. 19 illustrates a combination of a number of video frames into separate images of three drawers according to embodiments of the present invention.

FIG. 19 illustrates the combination of a number of video frames into separate images of three drawers 104r. As an example, the video frames 1901, 1902, and 1903 may be individual frames from a stream of 200 video frames taken while the drawers 104r are scanned by the movable mirrors 254. The video frame 1901 is the first frame of the 200, the video frame 1902 is the 200$^{th}$ frame, and the video frame 1903 is an intermediate frame.

Drawer image 1904 is an image of the top drawer 104r(1), constructed by digitally stitching the top portions 1808 of at least some of the video frames, for example including the video frames 1901, 1902, and 1903. Drawer image 1905 is an image of the middle drawer 104r(2), constructed by digitally stitching the middle portions 1809 of at least some of the video frames. And drawer image 1906 is an image of the bottom drawer 104r(3), constructed by digitally stitching the bottom portions 1810 of at least some of the video frames.

Figure 20:
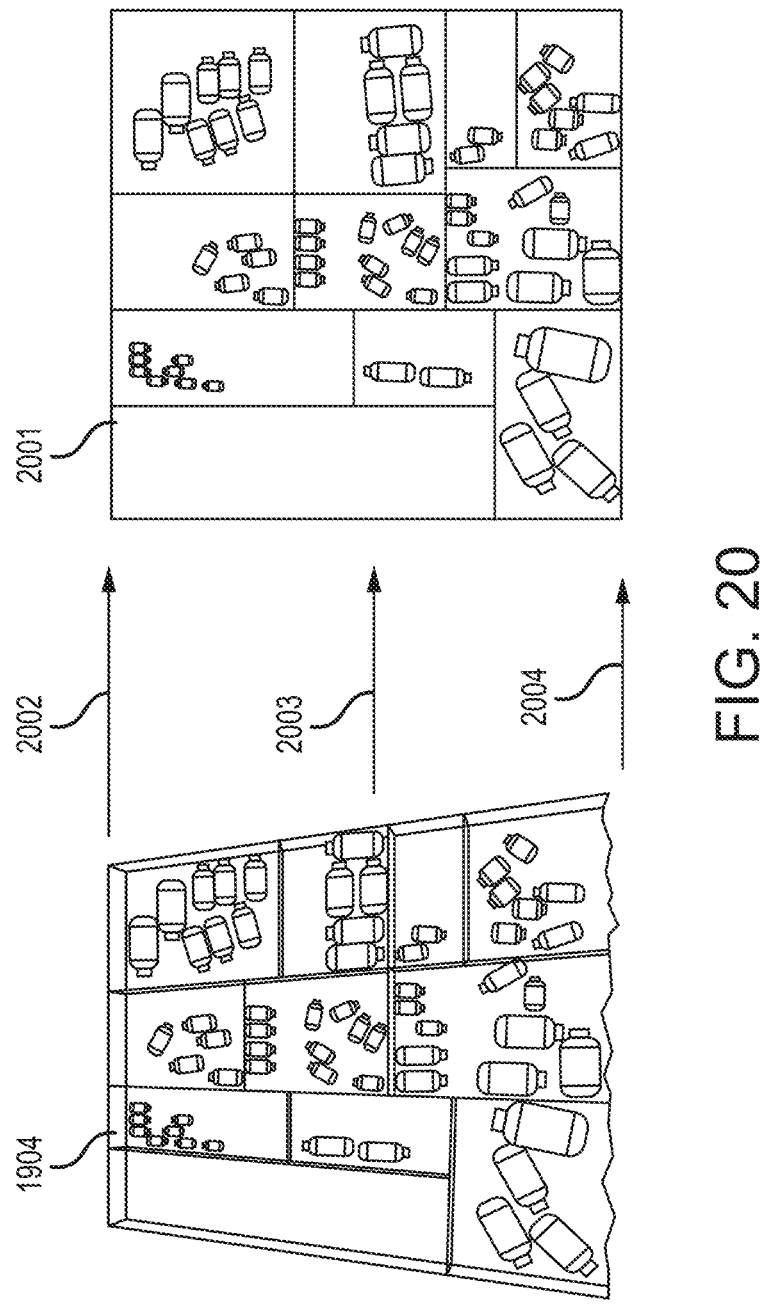
FIG. 20 illustrates one technique for correcting keystone distortion of a drawer image according to embodiments of the present invention.

Once the individual drawer images have been assembled, they may be further processed to remove the keystone distortion. FIG. 20 illustrates one technique for correcting keystone distortion of the drawer image 1904. In this technique, pixel rows of the drawer image 1904 are digitally scaled as needed to the length of the rows in the corrected image 2001. For example, the topmost pixel row may be expanded by pixel replication, interpolation, or another suitable technique, so that it has the correct number of pixels. The expanded row is copied 2002 into the corrected image. This expansion has the effect of making objects in that particular row look wider. The expansion and copying may be combined into a single operation, if desired.

Intermediate rows of the drawer image 1904 are also expanded and copied 2003 into the corrected image 2001. The intermediate rows are expanded to a lesser degree than the top row, in relation to their position in the image. The bottommost row of the drawer image 1904 may not need to be expanded at all, and may be copied 2004 directly into the corrected image 2001. In other embodiments, some degree of expansion may be used if desired. In some embodiments, the corrected image 2001 may be globally scaled up or down as well, either in post processing or as part of the scaling and copying of each pixel row.

In other embodiments, memory for the drawer image 1904 may be allocated as a rectangular image, and the scaling of the rows may be done in place within the allocated memory, without copying to a destination image.

The other drawer images 1905 and 1906 would be processed similarly. The resulting images may then be processed for counting items within the drawer. In some embodiments, the counting may be performed on the drawer images without correcting for keystone distortion.

While the inventory control system 100r has been described as imaging all of the drawers 104r simultaneously, this is not a requirement. For example, if it is known that only one drawer 104r has been opened since the most recent previous scan, then only that drawer 104r may be scanned for updating the drawer inventory. In other embodiments, the drawers 104r may be scanned one at a time for other purposes, for example to limit the peak power required for scanning, to limit the image processing bandwidth needed during scanning, or for other reasons. In some embodiments, more than one, but fewer than all of the drawers 104r may be scanned at a time.

Any suitable area imaging device 246 may be used, but in some embodiments, the area imaging device 246 is a digital imaging device using an electronic array light sensor such as a complementary metal oxide semiconductor (CMOS) sensor or a charge coupled device (CCD) sensor. An electronic array light sensor has an array of light-sensitive locations called "pixels" that accumulate electric charge when exposed to light. An image of a scene can be projected onto the sensor, and the charge accumulated by each of the pixels can be measured and converted to a digital value. An ordered array of these digital values may be called a digital image. The values in the digital image may also sometimes be called "pixels", and the meaning of "pixel" is generally apparent from the context of its use. In general, brighter parts of the scene result in more charges being accumulated in the corresponding pixels. The digital image thus is a digital representation of the brightness variations in the scene, and when properly displayed, replicates the scene. Some sensors can distinguish color, enabling color photography.

The area imaging device 246 may use an electronic array light sensor having between 1.5 and 25 megapixels, although imaging devices with more or fewer pixels may be used. The lens of the area imaging device 246 should have a focal length suitable for imaging the entire drawer width at the minimum working distance. In some embodiments, the lens may have a focal length of between 10 and 50 millimeters, depending on the size of the drawers and the physical dimensions of the imaging device sensor.

The table below illustrates one example imaging device configuration, for an inventory control system having eight drawers. Many other configurations are possible.

| Sensor Pixels (Horizontal × Vertical) | 2592 × 2048 |
|---|---|
| Pixel size | 4.8 micron |
| Sensor vertical dimension | 9.8 mm |
| Lens focal length | 20 mm |
| Number of drawers | 8 |
| Drawer separation | 60 mm |
| Drawer width | 500 mm |
| Drawer depth | 500 mm |
| Scan mirror height | 8 mm |

-continued

| Sensor Pixels (Horizontal × Vertical) | 2592 × 2048 |
|---|---|
| Working distance, closest drawer edge | 1000 mm |
| Working distance, farthest drawer edge | 1980 mm |
| Lens field of view needed | 26.6 degrees |
| Lens field of view provided | 27.6 degrees |
| Worst case resolution | 2.5 pixels/mm |

Using the above configuration, it may be possible to scan each drawer in about three seconds, gathering about 170 video frames at a frame rate of about 55 frames per second. The field of view at each drawer may be about 3 millimeters in the scanning direction, as the imaging device field of view is divided into 8 portions.

Referring again to FIG. 18, it will be observed that the optical path 1803 traverses most of the cabinet depth twice—from the area imaging device 246 to the mirror 248 and to the mirror 250r—before being directed upward to the staggered mirrors 252. This added optical path length may serve to reduce the ratio of the maximum and minimum working distances. This added length may allow the area imaging device 246 to have sufficient depth of field to clearly image objects at both the minimum and maximum working distances. The added length may also allow the optical path 1803 to grow sufficiently in width to be divided among the drawers 104r with the optical path portions 1804, 1805, and 1806 having reasonable widths.

Figure 21:
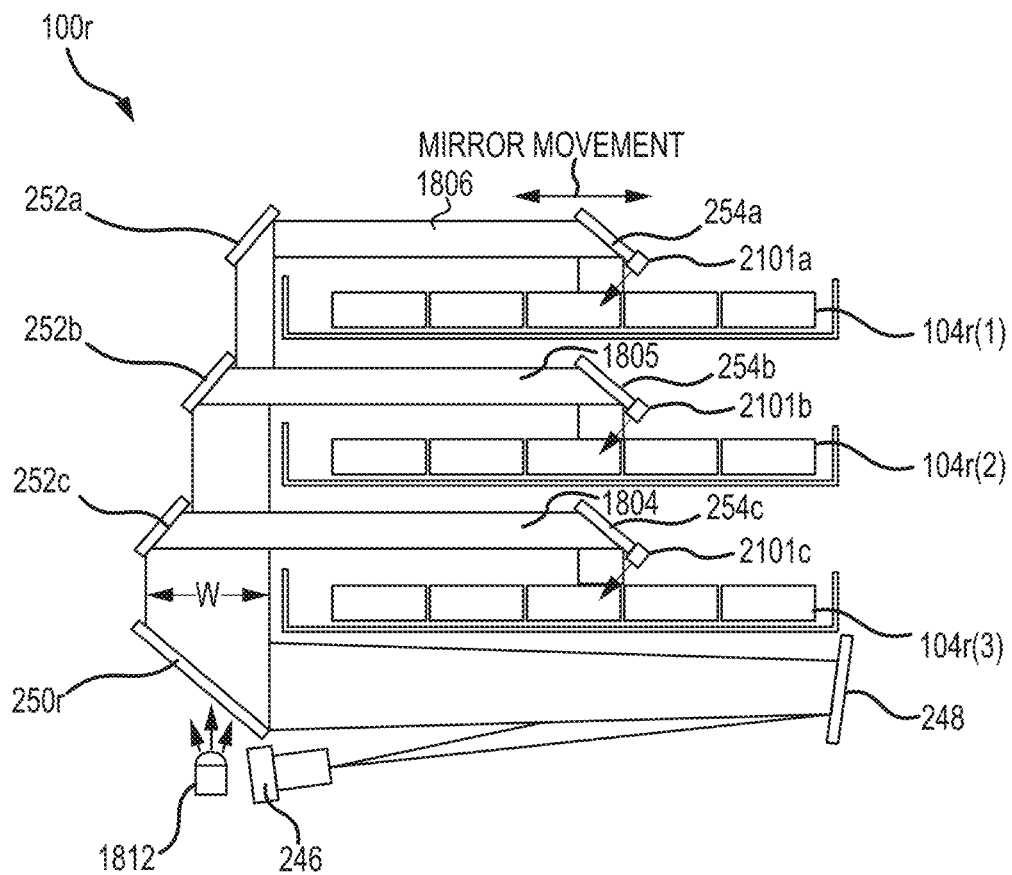
FIG. 21 illustrates an inventory control system with optical line generators attached respectively to movable mirrors according to embodiments of the present invention.

In other embodiments, at least some of the movable mirrors 254 may have optical line generators, which can be used for measuring the height of objects in the compartments of the drawers 104r. FIG. 21 illustrates an inventory control system 100r(1) with optical line generators 2101a, 2101b, and 2101c attached respectively to movable mirrors 254a, 254b, 254c. Each of the optical line generators directs a "curtain" of light diagonally downward toward the bins in the respective drawer 104r, forming a line of light on items in the bins. Because of the angular direction, the apparent front-to-back position of the line of light will vary depending on the heights of the items onto which the light falls.

Figure 22:
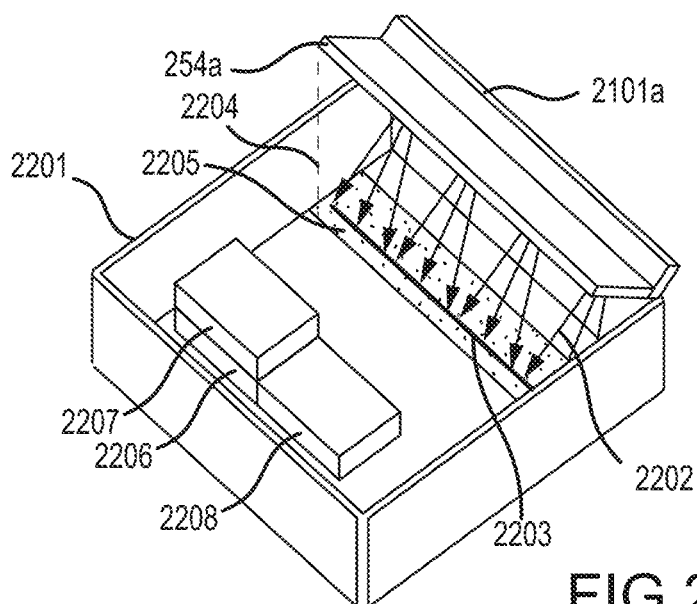
FIG. 22 illustrates a bin with optical line generators attached respectively to movable mirrors according to embodiments of the present invention.

FIG. 22 illustrates this capability in a single bin 2201 from the top drawer 104r(1). The movable mirror 254a is shown above the bin 2201, and the optical line generator 2101a is shown coupled to the movable mirror 254a. The optical line generator 2101a may use an array of lasers with diffractive or cylindrical optics to generate a curtain of light 2202, which casts a line of light 2203 on the floor of the bin 2201 if it is not interrupted by items in the bin 2201. Other kinds of line generators may also be used in other embodiments. The movable mirror 254a is preferably sufficiently wide to overhang the line of light 2203 on the floor of the bin 2201, as shown at 2204. The portion of the field of view of the area imaging device 246 directed to the movable mirror 254a is also preferably sufficiently wide to "see" the line of light 2203, in addition to "seeing" a portion of the bin 2201. The field of view is shown in FIG. 22 as the shaded area 2205.

The bin 2201 also contains three items 2206, 2207, and 2208. The item 2207 is on top of the item 2206. Because the system views the bins from above, it may not be able to determine that the item 2206 is in the bin 2201 based on image data alone. The system thus may have difficulty counting items that may be stacked. The use of the optical line generator 2101a can signal the presence of possible stacked items.

Figure 23:
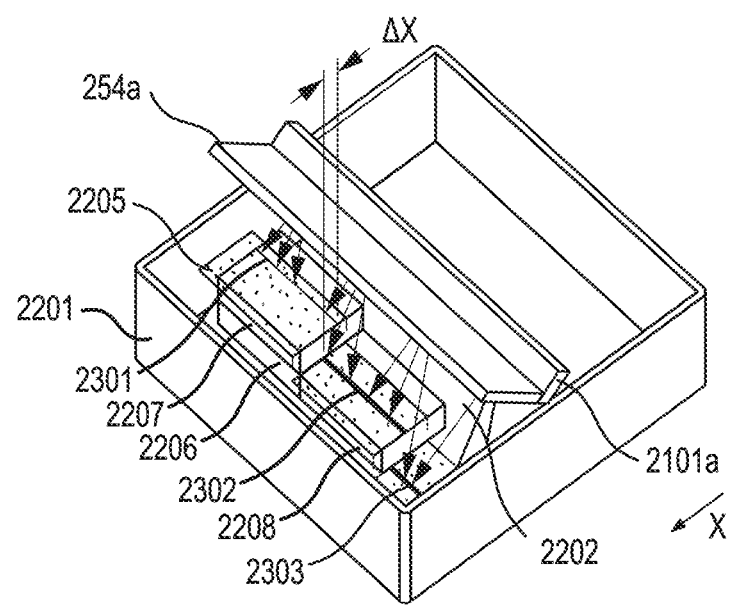
FIG. 23 illustrates the bin of FIG. 22 with a mirror positioned to reflect items of the bin.
Figure 24A:
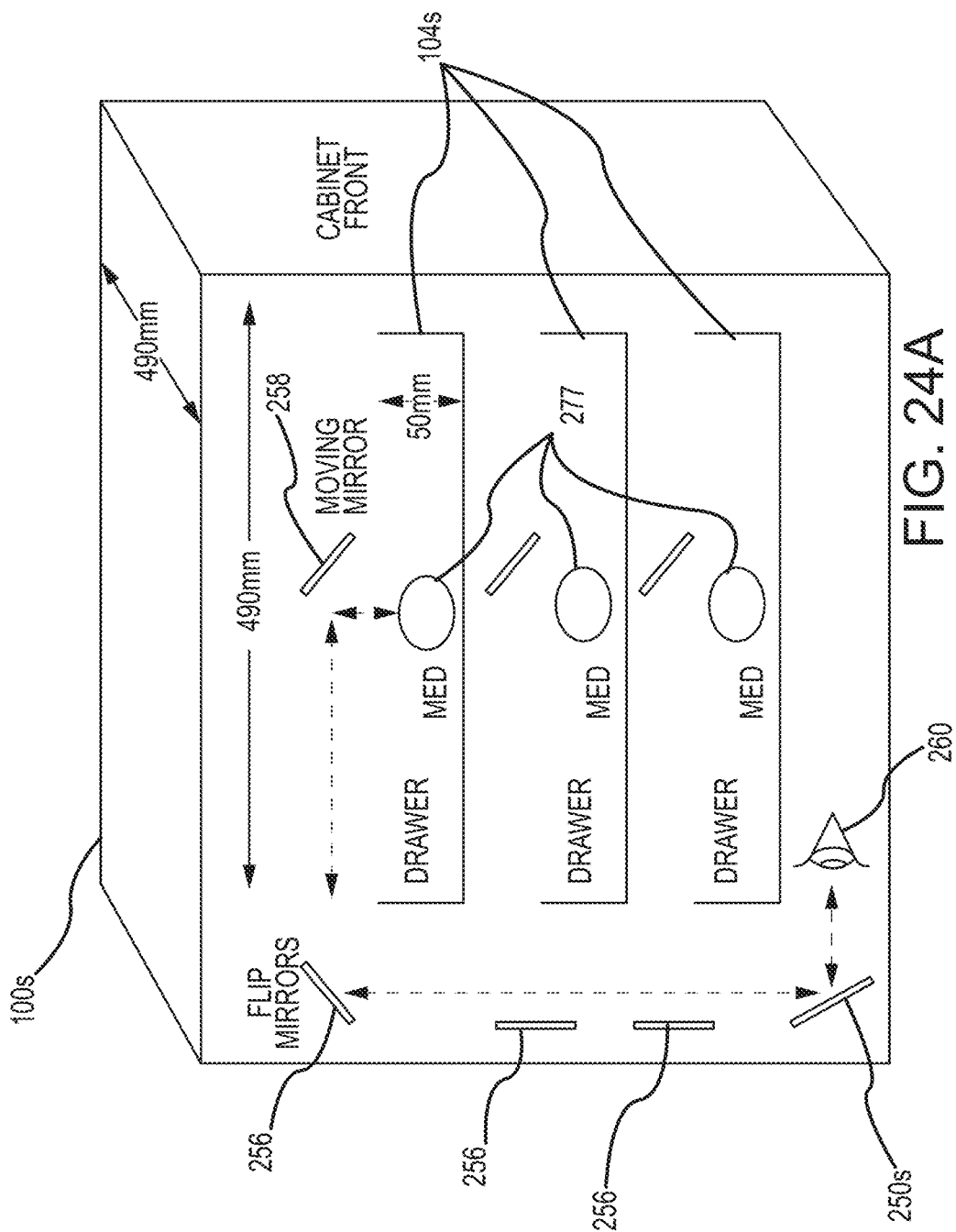
FIG. 24A illustrates an embodiment of an inventory control system that utilizes a moving imaging device and a series of motorized mirrors to image contents of drawers according to embodiments of the present invention.
Figure 24C:
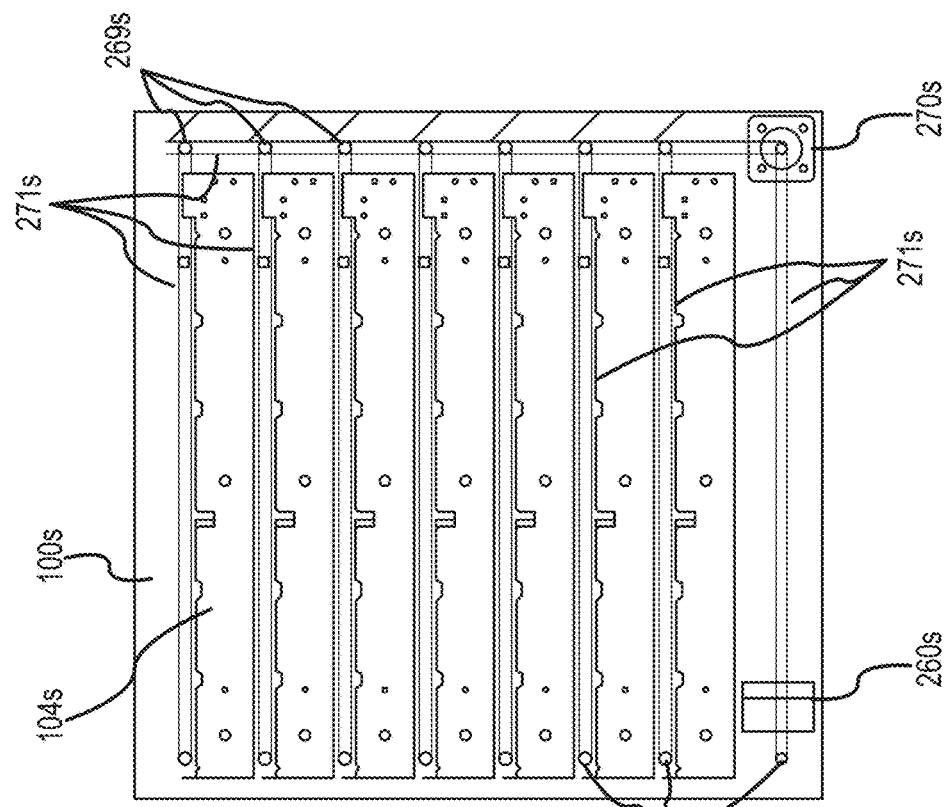
FIG. 24C illustrates a side cross-sectional view of the inventory control system of FIG. 24A.
Figure 24B:
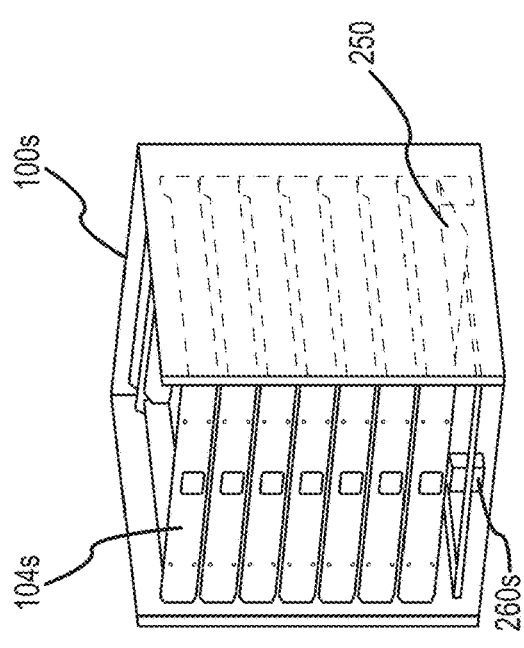
FIG. 24B illustrates a perspective view of the inventory control system of FIG. 24A.
Figure 24D:
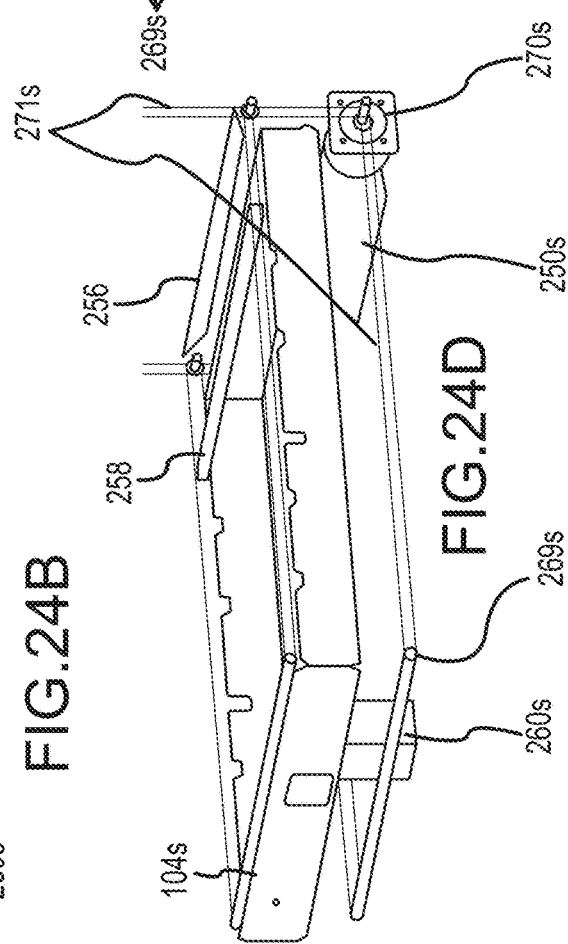
FIG. 24D illustrates a perspective view of a drawer and motor assembly of the inventory control system of FIG. 24A.

FIG. 23 illustrates the bin 2201 after the movable mirror 254a has moved far enough to reach the items 2206, 2207, and 2208. The curtain of light 2202 intersects the items 2207 and 2208 at different heights, and therefore at different "X" locations. Line segments 2301 and 2302 thus appear at different locations in the field of view 2205, indicating that those segments are reflected from items of different heights. The distance ΔX divided by the tangent of the angle of the light curtain 2202 from vertical indicates the difference in height of items 2207 and 2208. Line segment 2303 remains in the same location within the field of view, indicating that it lies on the floor of the bin 2201 as before.

The line segments may be easily distinguishable in images generated by the inventory control system 100r, by recognizing bright pixels of the color of the laser or other light source used in the optical line generators 2101. When shifts in the optically-generated line are detected, the inventory control system may adjust its item count on the assumption that items are stacked in a particular bin, or may take some other action. For example, the inventory control system may generate a warning message indicating that items are likely stacked, and that inventory counts may be unreliable. In some embodiments, the easily recognized line segments may be used as reference points in the stitching of images.

In some embodiments, a base of each drawer, such as drawer 104, includes a light-emitting surface (such as an array of LEDs). Oftentimes, the light-emitting surface is configured to produce a generally uniform field of light. An underside of each drawer 104 includes a light-receiving sensor. When the drawers 104 are closed, the light-receiving sensors of one drawer 104 may detect the light emitted from the light-emitting surface of the drawer 104 below. The various items present within the lower drawer 104 may block the light from reaching the light-receiving sensors, creating 'shadows' for the light-receiving sensors. Based on the location, size, and/or shape of these shadows, the light-receiving sensors may determine which and/or how many items are present within the drawer 104 below. It will be appreciated that in some embodiments, the light-emitting surface may be integrated into the underside of each drawer 104 while the light-receiving surface may be integrated into an interior base of the drawer 104. In some embodiments, rather than having a light emitting surface, a base (or underside) of each drawer 104 may include LEDs and/or other light sources positioned beneath item storage locations. In such arrangements, if the light-receiving sensors receive light from a particular LED the inventory control system 100 may determine that there is no item present. If no light is detected from a particular LED, the inventory control system 100 may determine that an item is present at a particular location.

FIGS. 24A-24D illustrate an embodiment of inventory control system 100s that is similar to and operates using similar principles as those described above. Inventory control system 100s includes a number of drawers 104s that each include an associated flip mirror 256 and a motor driven scan mirror 258 to allow an image sensing device 260s to image all the contents of the drawer 104s. Drawers 104s are configured to hold various items 277, such as medications. This embodiment operates in a similar manner as that described in relation to FIG. 18 above, but instead of having staggered mirrors 252, utilizes flip mirrors 256 to reflect contents from a drawer 104s downward to the image sensing device 260s. A controller determines which drawer 104s is to be scanned and then causes a an actuator to maneuver a corresponding one of the flip mirror 256s into a position in which contents of the selected drawer 104s can be imaged by the image sensing device 260s. For example, when a given drawer 104s is selected for scanning, a computing device, such as computing device 112, may send a command to an actuator that is coupled with the flip mirror 256 associated with the given drawer 104s that the corresponding flip mirror 256 to pivot and/or otherwise move into an angled positioned to reflect an image from the associated scan mirror 258. In some embodiments, rather than scanning a single drawer 104s, some or all of the drawers 104s are scanned in sequence. Such scanning may be done while the inventory control system 100s is idle and/or locked. To scan all of the drawers 104s, the controller selects a first drawer 104s (such as the top drawer 104s) and sends a command to an actuator associated with a first flip mirror 256 associated with the first drawer 104s that causes the first flip mirror 256 into an imaging position. The controller causes a first scan mirror 258 associated with the first drawer 104r to move along a length of the first drawer 104s while the image sensing device 260s is at a first position relative to a fixed mirror 250s and is capturing images of the first drawer 104r. Once the entire first drawer 104s has been scanned, the controller causes the first flip mirror 256 to move to a neutral position, the first scanning mirror 258 to move to a storage position, and the image sensing device 260s to move to a second position that is closer to or further from (depending on whether the first drawer 104s is higher or lower than a second drawer 104s to be imaged) the fixed mirror 250s. The controller then causes an actuator associated with a second flip mirror 256 associated with the second drawer 104s to move the first flip mirror 256 into an imaging position. The controller causes a second scan mirror 258 associated with the second drawer 104r to move along a length of the second drawer 104s while the image sensing device 260s is at a second position relative to a fixed mirror 250s and is capturing images of the second drawer 104r. Once the entire second drawer 104s has been scanned, the controller causes the second flip mirror 256 to move to a neutral position, the second scanning mirror 258 to move to a storage position, and the image sensing device 260s to move to a third location that is closer to or further from (depending on whether the first drawer 104s is higher or lower than a second drawer 104s to be imaged) the fixed mirror 250s. Such a process may be repeated until each of the drawers 104s has been imaged. By moving the image sensing device relative to the fixed mirror 250s, an optical distance may be maintained at a constant value across each of the drawers 104s, regardless of a number of drawers 104s present within the inventory control system 100s.

In some embodiments, rather than being triggered by the computing device 112 upon selection of the drawer 104s, the flip mirror 256 may be triggered by a controller associated with a particular drawer 104s and/or flip mirror 256. For example, each drawer 104s may include a sensor (not shown) that detects when the drawer 104s is being opened. This sensor may communicate a signal to the controller associated with a particular drawer 104s and/or flip mirror 256 that causes the flip mirror 256 to move into the imaging position. When not in use, each flip mirror 256 may pivot and/or otherwise move to a neutral position (such as being generally vertical) such that inactive flip mirrors 256 do not interfere with the scanning of other drawers 104s. The scan mirror 258 moves over the entire length of the drawer 104s and images vertically so there are not any blind spots. Object recognition can be done either locally in the storage system or the images can be sent to a server to do the object recognition and inventory counting. Raw images can be saved on a server for audit purposes. The imaging sensing device 260s may be a line scan imaging device having an encoder. A motor driving the scanning mirror 258 may clock the data out to generate an undistorted image of the entire drawer 104s.

In some embodiments, the imaging sensing device 260s may be a line scanner that is configured to move along a base of the inventory control system 100s. As just one example, a single motor assembly 270s having a motor with pulleys 269s and timing belts 271s may drive the moving parts (the imaging sensing device 260s, flip mirrors 256, and the scan mirror 258). Motor assembly 270s is operated by a controller (not shown) of inventory control system 100s, which may be similar to any of the controllers or computing devices described herein. Alternatively, some or all of the moving parts may be driven by independent mechanisms that are synchronized to keep the relative distance between the imaging sensing device 260s and the scanning mirror 258 constant. This coordinated movement can be accomplished with servo motors and/or stepper motors. In the case of a single drive mechanism, all the scan mirrors 258 would move regardless of the drawer 104s being imaged. With independent actuators, only the scan mirror 258 above the drawer 104s being imaged needs to move. A movement signal from the actuators would be used to clock the data out from the imaging sensing device 260s for the best image quality. This could be an encoder or some other distance sensor. Alternatively, the line scan imaging device data could be clocked by the imaging device's internal clock. If the speed of the scan is near constant, the image distortion will be minor, especially for the primary requirement of imaging and counting objects. The flip mirrors 256 may utilize independent actuators, such as solenoids that flip between two hard stops. Only the imaging position needs to be accurate, the "out of the way" does not need to stop the flip mirror 256 accurately.

In some embodiments, the line scan imaging device pixels are 10 microns tall. In instances in which the imaging device and mirrors are perfectly aligned, the various mirrors only need to be 20 microns tall, however the mirror size may be larger, in some embodiments reaching up to 5-10 mm tall. The mirror height requires the drawers to be separated by 15 to 20 mm to package the moving scan mirrors 258. In other embodiments, where the image sensing device 260s is positioned at the top portion of another embodiment of an inventory control system, the angles of orientation and/or tilt of the mirrors 256 and 250s may be appropriately altered to allow proper imaging of the contents of the drawers 104s. Other embodiments may also include positioning of the area imaging device 246 towards the rear-center position of the inventory control system or the top-front position of the inventory control system. Such modifications may be construed as being within scope of the present invention.

In other embodiments, such as that shown in FIGS. 25A-25D (which may be similar to the embodiment shown in FIG. 24A-24D except for the imaging sensing device 260 and the motor assembly 270, and thus will be described using the same reference numerals except for the imaging sensing device 260 and the motor assembly 270), imaging sensing device 260t may be fixed in place, thereby reducing the number of moving parts and thus the complexity of the scanner. However, such a design may produce keystone distorted images of the drawers 104s along with the magnification differences between the drawers 104s that were described in the line scanning embodiment above. The keystone distortion of each drawer 104s will be different, but will be known and constant making for simple image processing corrections to yield accurate object identification. In addition, known fixed objects in each drawer 104s, such as bin dividers, can be used to confirm the distortion is being corrected properly.

Figure 25A:
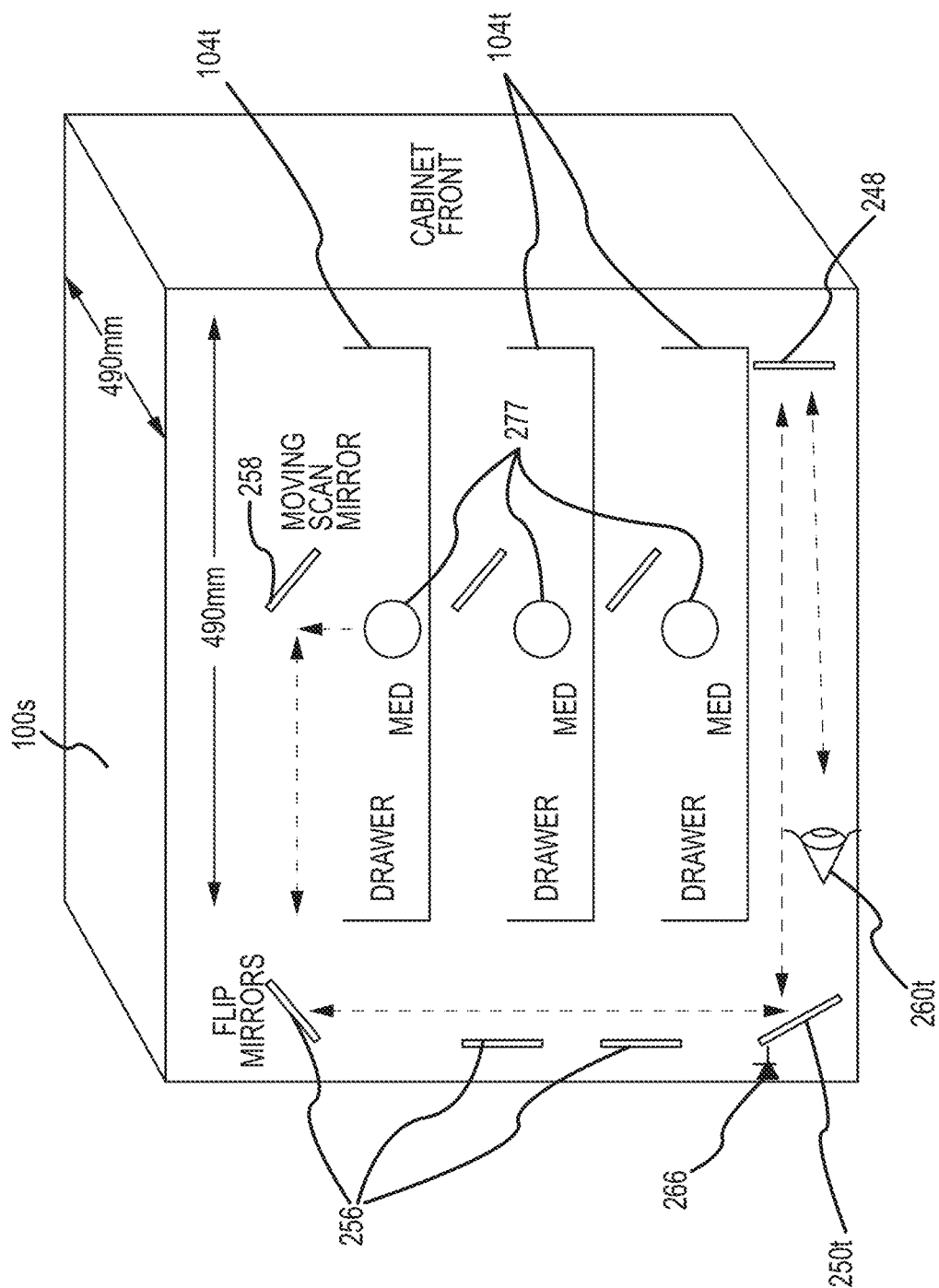
FIG. 25A illustrates an inventory control system that utilizes a fixed imaging device and a series of motorized mirrors to image contents of drawers according to embodiments of the present invention.
Figure 25B:
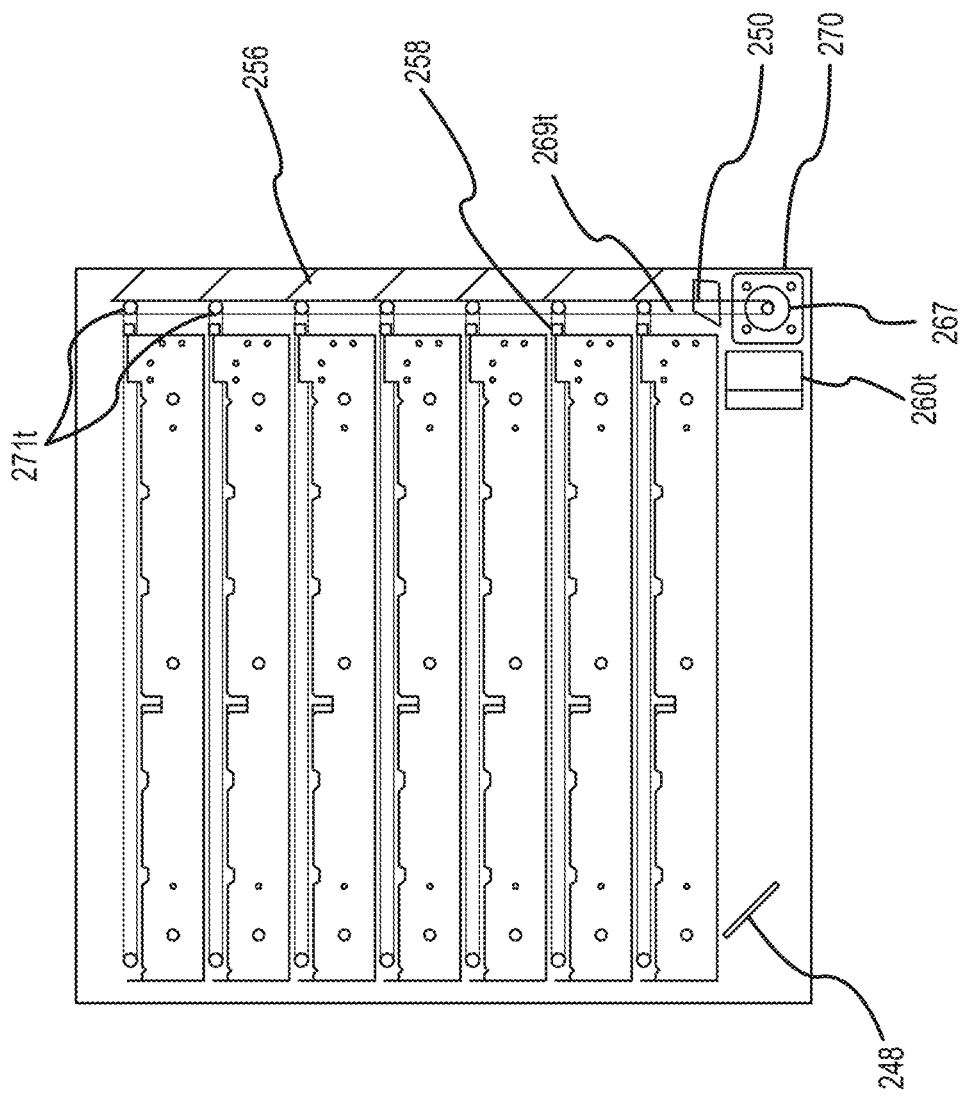
FIG. 25B illustrates a side view of the inventory control system of FIG. 25A.
Figure 25D:
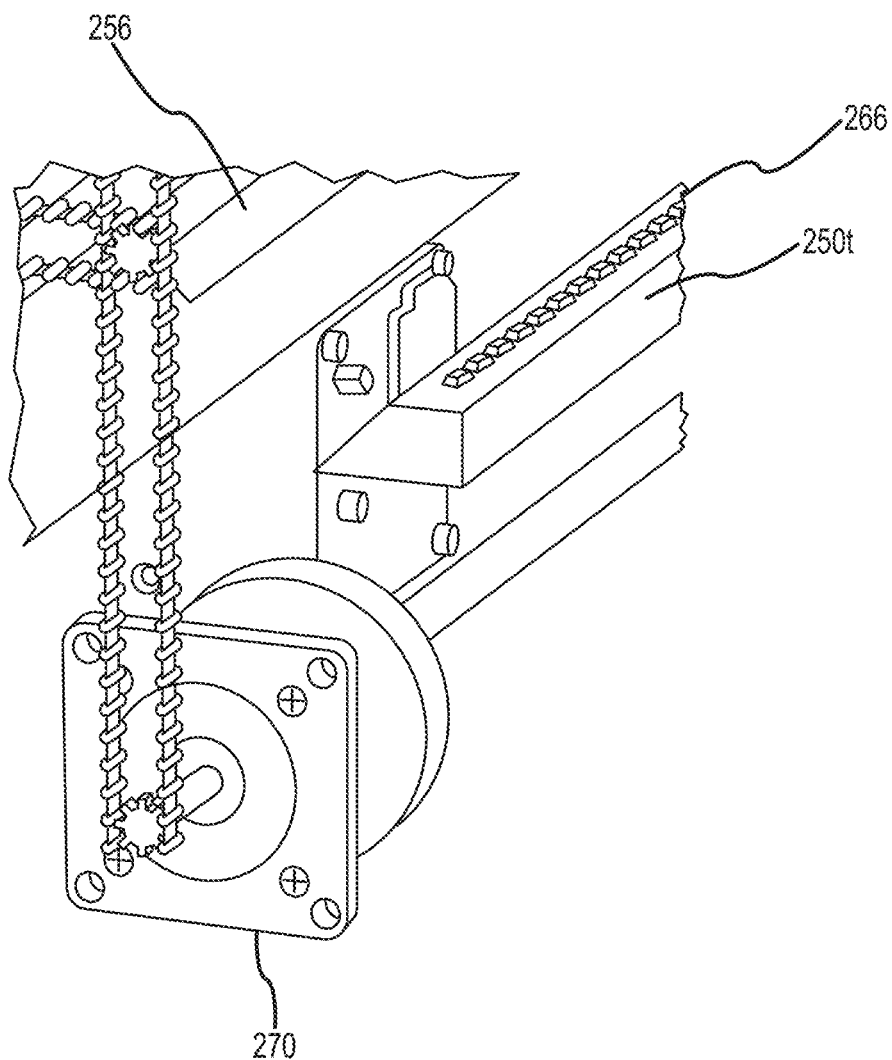
FIG. 25D illustrates a perspective view of the motor assembly of FIG. 25C.

In the fixed imaging device layout, the scan mirrors 258 can either be ganged together, such as by using a motor assembly 270t having a number of belts 269t and pulleys 271t, and driven by a single actuator 267, or be driven by separate actuators. For example, as illustrated in FIGS. 25C and 25D, the belts 269t(1) may be used to adjust an orientation of one or more of the flip mirrors 256, while belts 269t(2) may be used to control the movement of one or more of the scan mirrors 258. In some embodiments, the movement of some or all of the belts 269t(1), 269t(2) may be driven by a single actuator 267. In such embodiments, a controller may operate a series of clutch mechanisms (not shown) or other mechanisms may be utilized to control which of the belts 269t(1), 269t(2) are being driven at a given moment. The movement of the scan mirror 258 can be sensed with an encoder or other distance sensor and clock the data out of the imaging sensing device 260t. Alternatively, the imaging sensing device 260t can be internally clocked, and, if the scan speed is reasonably constant, the image distortion will be acceptable. Since all the moving scan hardware is inside the cabinet and present no danger to the users, closed drawers can be scanned while allowing normal cabinet access to shelves or other drawers. In terms of inventory control, the only requirement is that all drawers that were opened by a user must be scanned prior to allowing access to another user. A single drawer scan should take 1-3 seconds, and at most only the last drawer opened by the user needs to be scanned prior to allowing a new user access, users should not see any delay in access with "real time scanning."

In the both of the embodiments of FIGS. 24A-24D and 25A-25D, the flip mirrors 254 and imaging sensing devices 260 may be replaced with a traditional area imaging device that images all drawers 104s. Only the scan mirrors need to move. The area imaging device will capture video ribbons of each drawer 104s that will need to be deconvoluted to reconstruct a drawer image. In this setup, there is no need for an encoder to clock the data out of the imaging device. In some embodiments, only the line scan imaging device from the embodiment of FIGS. 25A-25D is replaced with an area imaging device, while all other components remain the same. In such an embodiment, only a narrow band of the image field of the area imaging device will capture the items, but the video of several images taken as the moving mirror 258 scans the drawer 104s can be stitched together to create a single drawer content image. This stitching could be done without an encoder signal from the moving mirror 258, but rather from known features in the image itself. The image band would need to have sufficient pixel width to accomplish this ribbon stitching. In another embodiment, the fixed line scan imaging device may be replaced with an area imaging device that takes ribbons of images that can be stitched into a single image of the drawer contents. Since the imaging device is fixed, the magnification will vary along the drawer images, and this keystone distortion will also need to be corrected. In other embodiments, by using an area imaging device, the flipping of the flip mirrors 256 may be eliminated. Instead, a staircase and/or other staggered arrangement of fixed mirrors may be disposed up the back of the inventory control system 100s to image all the drawers 104s in parallel. The area imaging device may have a ribbon image from each drawer 104s that will need to be separated from the initial image taken and placed in a separate image of the drawer 104*s* it has captured. In this embodiment, the only moving parts are the scan mirrors.

Each of the embodiments above may include a line scan imaging device and/or an area scan imaging device. The imaging device may include a fixed focal length lens in some embodiments, however other embodiments may utilize a motorized zoom lens that enables constant magnification for all drawers 104*s*, 104*t*. The lens can be fixed aperture and/or may have a motorized aperture that is configured to equalize and/or otherwise make the illumination between drawers 104*s*, 104*t* more uniform, as the more distant drawers will be less bright without any correction. In some embodiments, an LED light bar 266 (see FIG. 25D), and/or other light source (visible light and/or IR (such as in the case of lock-lidded bins)) may be included. For example, the LED light bars 266 may be positioned rearward of the imaging device and may be directed upward toward the staggered mirrors 252 and/or the flip mirrors 256. In some embodiments, the LED light bar 266 may be affixed to one of the fixed mirrors 252. In some embodiments, each scan mirror 258 may have a dedicated LED light bar 266. This LED light bar 266 may have constant intensity or variable intensity, which enables the LED light bar 266 to provide more light to the most distant drawers. In this manner all drawer images will have similar visible characteristics to simplify the image processing software. Each drawer 104*s*, 104*t* will include at least one dedicated scan mirror 258 per drawer 104*s*, 104*t*. In some embodiments, the scan mirrors 258 can be ganged together so that they all move as a single unit. If the LED light bar 266 is stationary illuminating the flip mirrors 256, then these scan mirrors 258 may be passive. In other embodiments, the LED light bar 266 may be mounted on the scan mirrors 258 and may include wired connections that deliver power and control commands to the scan mirrors 258. Embodiments including a motor assembly 270*s*, 270*t* may include an encoder (not shown) to move either only the scan mirrors 258, or both the imaging device and the scan mirrors 258. The encoder is used to clock the data out of the line scan imaging device. A timing belt drive may be included to couple all of the moving parts to a single drive motor, however some embodiments may utilize multiple motors. Embodiments may also include individual flip actuators to flip one flip mirror 256 down to scan the associated drawer. These actuators may be solenoids that rotate the flip mirrors 256 between two hard stops.

Figure 26:
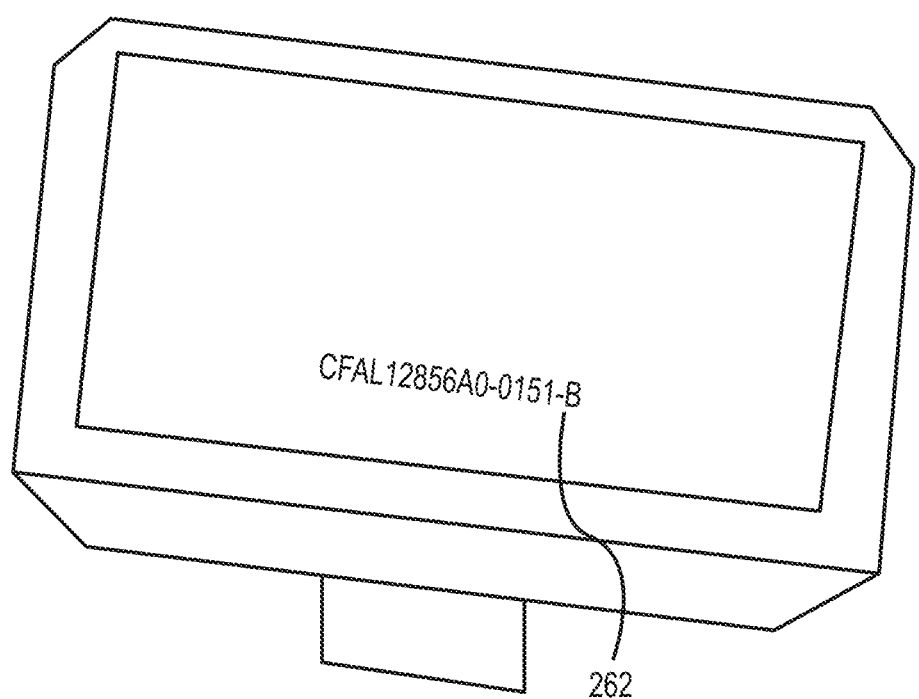
FIG. 26 illustrates a bin lid having a transparent OLED display according to embodiments of the present invention.

In some embodiments, lids (not shown) may cover some or all of the bins. For example, the bins may be similar to bins 172*z* of FIG. 32 that are within the drawers 104*z*. These lids may be opaque in some instances. In other embodiments, the lids may be designed as being transparent to allow the imaging devices, line scanners, and/or other imaging sensing devices to image the contents of the bin, by viewing through the lid. In one particular embodiment, the lid may be made of a material transparent in the visible light spectrum, i.e., illumination by visible light reveals the contents within the lock-lidded bins when the lids are closed. In a different embodiment, the lid may be transparent to a particular wavelength of light (non-visible wavelength), such as to infrared, near-infrared, far-infrared, or ultraviolet or beyond ultraviolet, while being translucent or opaque in the visible light spectrum (visible to humans) i.e., when light at the appropriate wavelength is focused on the top of the lock-lidded bins, the contents within the bins are revealed, although not to a user. Such a reveal may be captured by a special imaging system, such as an imaging device designed to capture images at the particular wavelength of light. In some instances, the same imaging device may be configured to capture images across multiple wavelengths, including on either side of the visible spectrum. In other instances, there may be multiple imaging devices, each designed to capture images at a particular range of wavelengths. In some embodiments, such as shown in FIG. 26, the lids may include electrically-driven transparent OLED displays 262, the opacity of which can be controlled by the cabinet. These displays could also provide the user with additional information about the contents of the bin or status of the system.

In other embodiments, each drawer, which may be similar to any of the drawers 104, may be imaged using one or more imaging devices that are positioned above a respective drawer and are translatable about one or more axes to image the storage regions of the drawer. For example, a single imaging device may be maneuvered to different locations above the storage region and may capture images at each of the locations. These images may be used to inventory the contents of the storage region. In some embodiments, the images may be stitched together and/or otherwise combined to get a composite image of the storage region. In other embodiments, object detection may be performed on the images to determine if a full bin or other partition is provided in a single image. In yet other embodiments, rather than relying on image stitching each imaging device may be positioned to image an entirety of one or more sections (such as individual bins) of the storage region. In such embodiments, the computing device, such as computing device 112 may analyze the images, detect section partitions (such as bin edges), and determine which sections of the storage region are entirely within a single image and analyze these image regions to conduct an inventory count while ignoring incomplete sections of the storage region found in a given image.

When piecing together the images (and/or for performing object detection to identify a particular item within the drawer), a location of the imaging device may be monitored for each image. This information may be used by the computing device to assemble a composite image of the storage region and/or to identify where in a drawer a particular bin and/or other partition is located. In some embodiments, a drawer configuration may be stored in a database on and/or otherwise accessible by the computing device. This allows the computing device to know where bins and/or other partitions are located, as well as the size of each bin and/or other partition to be known. Such knowledge is usable by the computing device to inventory the contents of the drawer without stitching the individual images together. Rather, the computing device may identify bins from the individual images that match or otherwise correspond to those in the known drawer configuration.

In some embodiments, IR sensors may also be used to determine when a user reaches into a drawer, such as any of the drawers 104, and/or bin has been accessed. In some embodiments, IR sensors may be positioned in a similar manner as the imaging devices 130 and/or other imaging devices described above. In some embodiments, the IR sensors may be used in place of imaging devices, while in other embodiments the IR sensors may be used in conjunction with imaging devices 130 and/or other imaging devices. The IR sensors may be configured to create a light curtain that the user breaks. In some embodiments, rather than user IR wavelengths, a visible light curtain may be utilized. If using wavelengths on the visible spectrum, the light curtain can be strobed to filter out ambient 60/50 Hz light. In some embodiments, the IR sensors may be configured to detect a heat signature of a user as the user reaches into the drawer and/or bin. A computing device, such as computing device 112, may then determine that the user has reached in and has likely taken items from the drawer and/or bin. Based on the detected location of the user's hand, the computing device may determine what items were likely removed according to a known drawer/bin configuration.

Figure 27B:
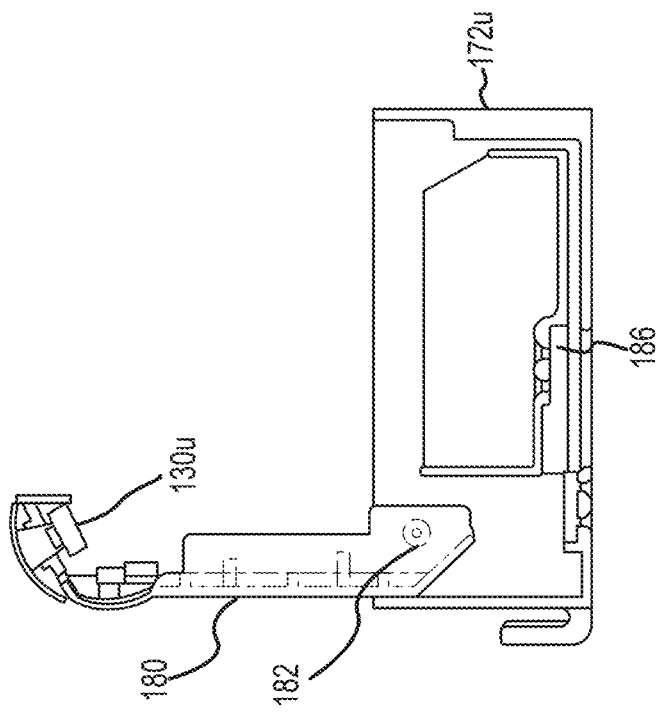
FIG. 27B illustrates a side cross-sectional view of the lock-lidded bin of FIG. 27A.
Figure 27A:
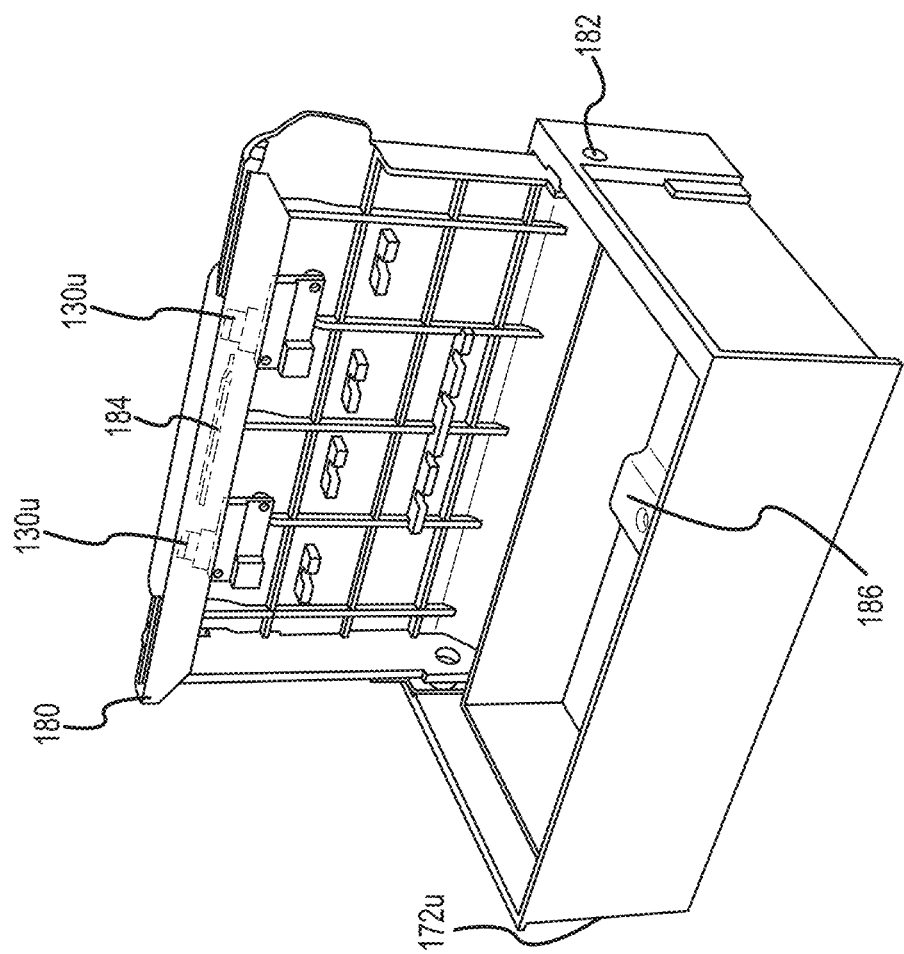
FIG. 27A illustrates a perspective view of a lock-lidded bin according to embodiments of the present invention.

FIGS. 27A and 27B illustrate a bin 172u that may be integrated into any of the drawers and/or inventory control systems described herein. For convenience of discussion, bin 172u will be describe in connection with inventory control system 100a of FIGS. 1A and 1B. Bin 172u may include a locked lid 180. As illustrated, the lid 180 may be secured to the bin 172u using a hinge 182. However other embodiments may use other attachment mechanisms, such as sliding track, snaps, and the like. The bin 172u may also include one or more electronically actuated locking mechanisms (not shown), such as solenoid-based locks that may be controlled by the computing device 112 to control access to the bins 172u. Such bins 172u are particularly useful to further secure high diversion risk items, such as narcotics. However, such bins 172u may make it difficult for drawer and/or housing based vision sensors to maintain an accurate count of items stored within the bin 172u. To remedy these problems, the bins 172u may be equipped with one or more imaging devices 130u. As illustrated, the imaging devices 130u are positioned on an underside of the front of the lid 180 and are oriented such that the imaging devices 130u image the interior of the bin 172u when the lid 180 is fully open. In other embodiments, the imaging devices may be positioned to image the interior when the bin 172u is closed. To provide additional illumination for imaging, one or more light elements, such as LEDs 184 may be positioned within the interior of the lid 180 and/or bin 172u.

In embodiments where the image is taken when the lid 180 is open, the LEDs 184 and/or imaging devices 130u are only activated when the lid 180 is in an open state. In other embodiments, the imaging device 130u and/or LEDs 184 may be activated only once the lid 180 is closed and locked.

In addition to, or in place of, vision sensors, some embodiments of bin 172u may include one or more load sensors. As illustrated in FIGS. 27A and 27B, bin 172u includes a load sensor in the form of a strain gauge 186, although other load sensors may be used as will be discussed in greater detail below. In embodiments in which a locked lidded bin 172u includes a load sensor (with or without the use of imaging devices 130u and/or LEDs 184), items (oftentimes medications) placed within the bin 172u will be weighed using an integrated force sensor (load cell or similar) before and after an item has been dispensed. Based on the change in weight between the two measurements, as well as the assigned bin content, the inventory control system, such as inventory control system 100 can determine the change in count of items within the bin 172u.

To restock such bins 172u, a user may input the quantity of items stored in a particular bin 172u into the inventory control system 100a after the bin 172u has been refilled. Attributes of an assigned item (which may include a known and/or expected weight of the item) are provided to the software of the inventory control system 100a. After any items have been placed in the bin 172u, a measurement may be taken of the bin 172u and/or contents thereof. In some embodiments, the inventory control system 100a may then use the input count and the weight per item to determine an expected weight, which may then be compared to the measured weight. In other embodiments, the inventory control system 100a may use the measured weight to determine an expected quantity of items, which may then be compared to the item count input by the user. The comparison of the input data and the measured data may be used to confirm the item weight and count. If the input and measured data matches, the restock process ends. If the input and measured data do not match, software of the inventory control system 100a will prompt the user to empty the bin 172u, re-tare and/or otherwise reset the load sensor, weigh, and re-count and/or accept the input user count. In some embodiments, input quantities of items may not match the weighed quantities due to various factors, such as a change in the item, a sensor shift and/or miscalibration, and/or user miscount. Any discrepancies in the input and measured data may be logged, along with an indication of how the discrepancy was reconciled (e.g., whether the user count was utilized, the measured count was utilized, etc.).

Prior to removing an item, the bin 172u may be weighed. For example, after a prior access to the bin 172u (which may have been for item removal or restocking purposes) the bin 172u may be weighed upon the lid 180 being closed and/or locked. To remove an item from the bin 172u, the bin 172u is first unlocked by the inventory control system 100a. The user may then access items within the bin 172u. After the lid 180 is closed and/or locked, the load sensors may again weigh the bin 172u and/or contents thereof. Based on the measured weight before and after the user access, the inventory control system 100 may determine how many items have been removed (if any) from the bin 172u. In some embodiments, a second measurement of the bin 172u may be taken once the drawer 104a is closed and secured in the inventory control system 100a. Any discrepancies between the measurement taken after the closure of the bin 172u and the measurement taken after the closure of the drawer 104a may be presented to the user to confirm or update. All results may be added to a log file.

In some embodiments, the inventory of one or more bins 172u (or any of the bins described herein) may be triggered remotely. For example, a central pharmacy and/or other remote device may request that an inventory of a particular bin 172u and/or set of bins 172u (such as all of the bins 172u in a given drawer (such as drawer 104a), inventory control system (such as any of the inventory control systems 100), and/or medical facility) be taken. The central pharmacy may send a request to one or more inventory control systems 100 associated with the particular bin 172u and/or set of bins 172u. The request causes one or more of the inventory control systems 100 to poll the particular drawer 104, bin 172u, and/or set of bins 172u for new measurements. Inventory for each of the particular bin 172u and/or set of bins 172u may be determined. In some embodiments, the data from the remote scans quantities can be compared with logged transaction data to determine whether there are any discrepancies between the remote scans and the transaction data. In some embodiments, the data from remote scans may be utilized for refill purposes. For example, where the remote device is part of a central pharmacy system, the inventory from various bins 172u may be used to determine when the quantity of an item within a particular bin 172u falls below a predetermined threshold and necessitates refilling. In some embodiments, the remote scan data may be used to check for hardware issues. For example, where discrepancies are detected between the remote scan data and user transaction data, the inventory control system 100a may alert one or more users to check and verify the actual item count. If the transaction data is correct, the user may determine that the load sensor hardware is malfunctioning and/or needs to be recalibrated. In embodiments where the bin 172u includes one or more other sensors, such as imaging devices 130u, data from the imaging devices 130u (or other sensor) may be compared to the transaction data. If the imaging device data and the transaction data match, the inventory control system 100a may determine that the load sensors are not operating properly. If the imaging device data and the transaction data does not match, the imaging device data may be compared to the load sensor data. If the imaging device data and the load sensor data match, the inventory control system 100 may determine that there is an error with the transaction data. If none of the various data matches, the inventory control system 100 may alert one or more users to check and verify the actual item count and/or identify any problems with the various sensors.

In some embodiments, the load sensors may be integrated into the bin 172u itself. In other embodiments, the load sensors may be affixed to a base of a drawer 104, with the bins 172u (with or without lids) being secured to the drawer 104 atop the load sensors.

Figure 28:
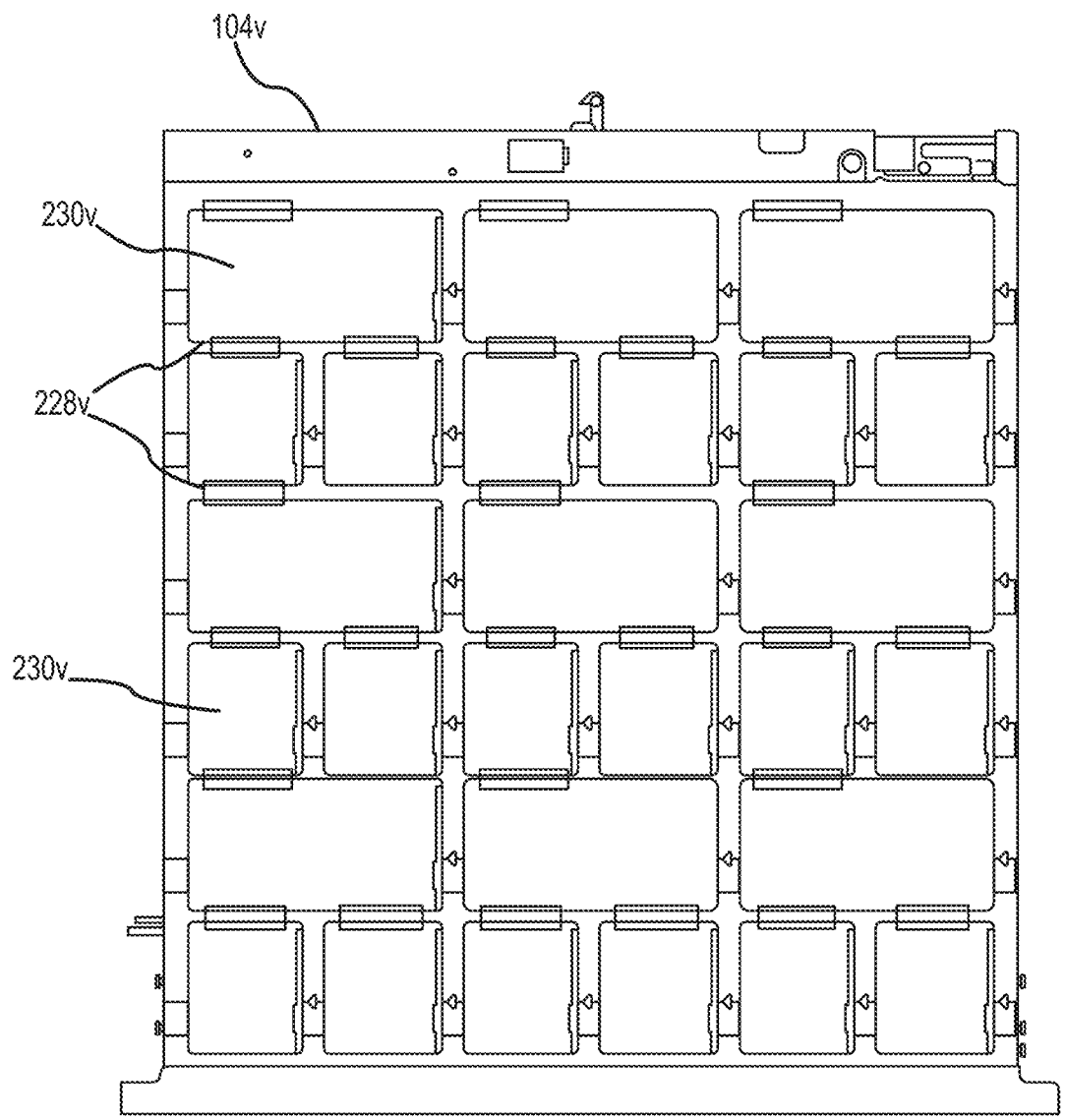
FIG. 28 illustrates a drawer having a number of load sensors integrated into a base of the drawer according to embodiments of the present invention.

FIG. 28 illustrates one example of a drawer 104v having a number of force or other load sensors 228v positioned about a base of the drawer 104v. As illustrated, the base of drawer 104v includes a number of bin locations 230v that are configured to receive individual bins (not shown here). While illustrated with alternating rows of large and small bin locations 230v, it will be appreciated that any combination and arrangement of bin locations 230v is possible, such as configurations in which all bin locations 230v are the same and in which the bin locations 230v are arranged in an asymmetrical layout. Here, each bin location 230v includes a load sensor 228v. As each bin location 230v is coupled with a respective bin, a portion of the bin sits atop one of the load sensors 228v. This allows a weight of each bin and its contents to be measured.

Figure 29A:
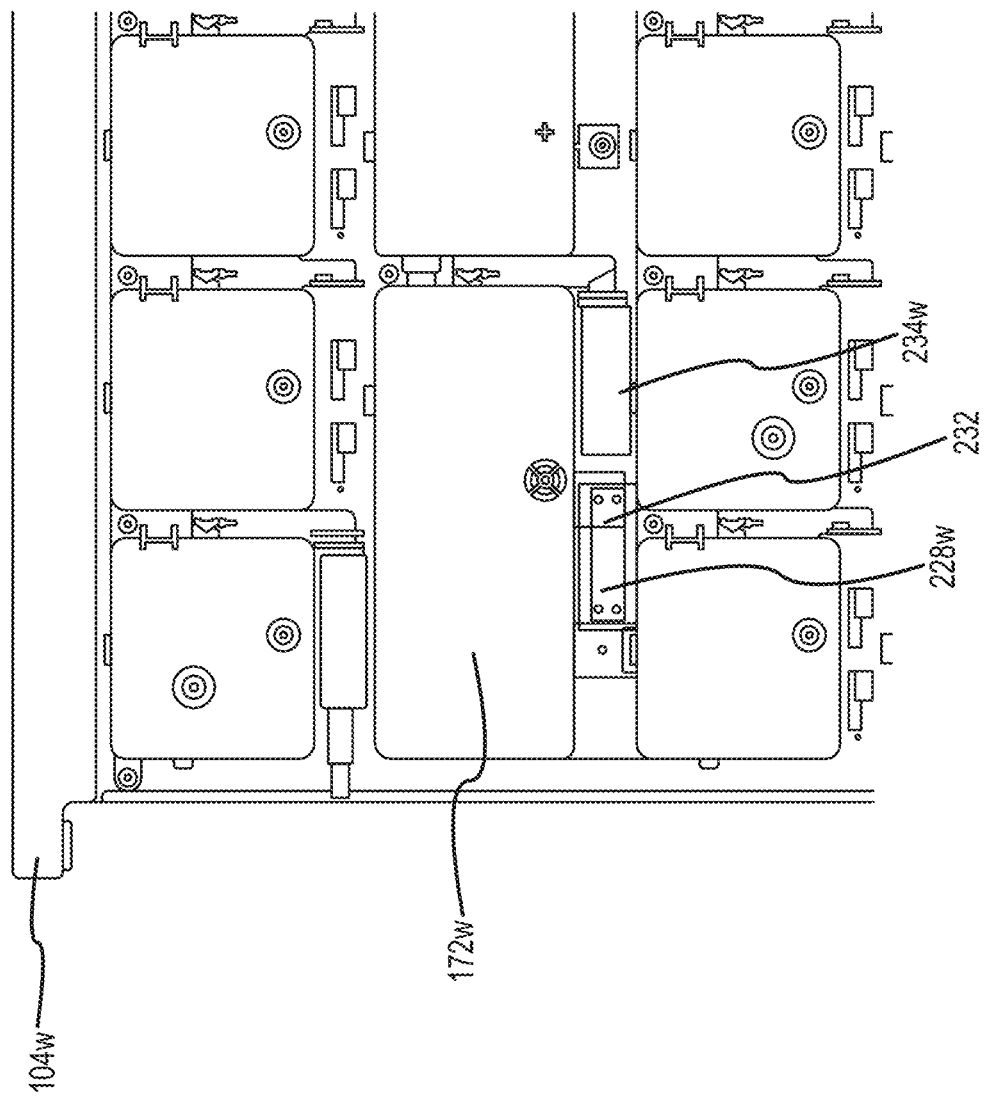
FIG. 29A illustrates a top view of a bin mounted on a drawer load sensor according to embodiments of the present invention.
Figure 29C:
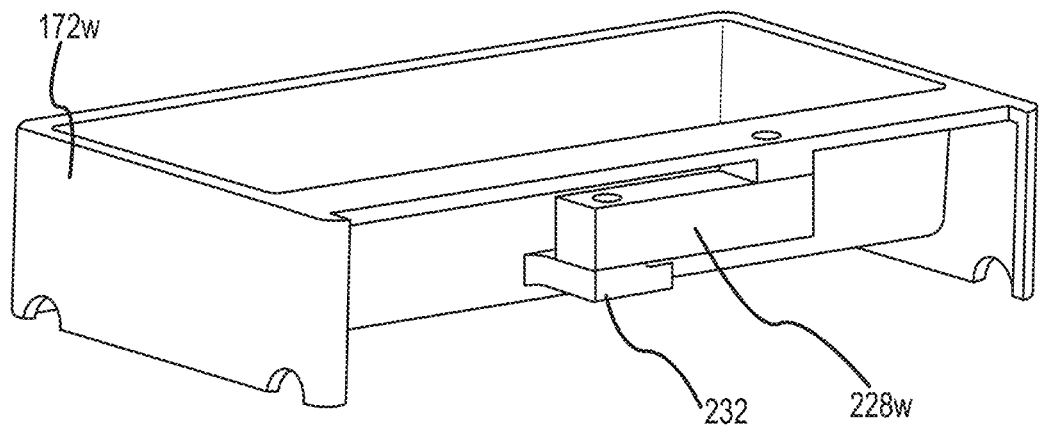
FIG. 29C illustrates an isometric view of the bin of FIG. 29A.

FIGS. 29A-29C illustrate a drawer 104w having a number of bins 172w. Each bin 172w may include a tab 232w that protrudes outward from a side of the bin 172w and is coupled with a top and/or bottom surface of the load sensor 228w, such that the connection with the load sensor 228w supports the bin 172w. A bin solenoid 234w is provided that provides overload shock protection for the load sensors 228w. For example, the solenoid 234w may be used to lock the bin 172w in a desired position to protect the load sensor 228w when the load sensor 228w is idle.

In some embodiments, rather than having a designated load sensor 228w for each bin 172w, two or more bins 172w (with or without lids) may be coupled with a drawer 104w using a shared load sensor 228w.

Figure 30:
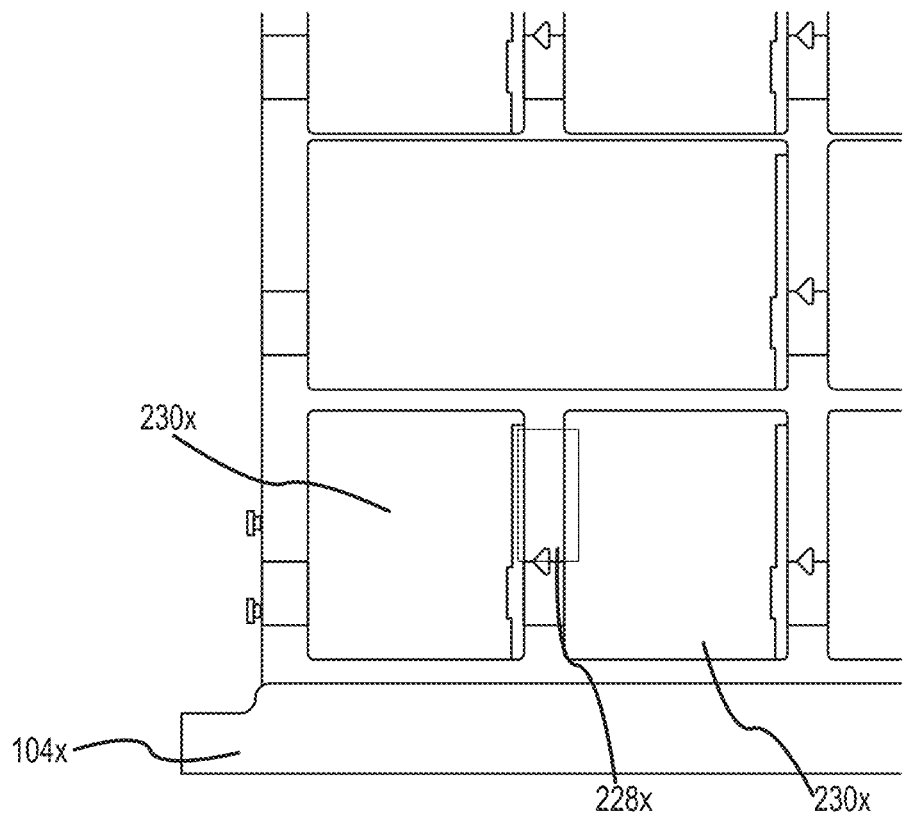
FIG. 30 illustrates a drawer having a number of load sensors integrated into a base of the drawer according to embodiments of the present invention.

FIG. 30 illustrates a portion of a drawer 104x having a number of force or other load sensors 228x positioned about a base of the drawer 104x. Here, at least some of the bin locations 230x share a single load sensor 228x. Multiple bins (not shown here) may be mounted to a single load sensor 228x or set of load sensors 228x. The load sensor 228x will then measure the combined weight of the all of the bins mounted thereon. In instances where one or more of the bins mounted on a single load sensor 228x have different items than another one of the bins, it is necessary to determine which bin was accessed to determine which items have been removed. This may be done in several ways. In some embodiments, the inventory control system 100 may use information associated with which bins have been unlocked to infer that a change in weight measured by the load sensor 228x is attributed to items being removed from or added to the particular single bin. In other embodiments, the bins may include sensors (not shown) that monitor a state of a lid (such as lid 180). When the lid is opened, the inventory control system 100 may be alerted and may determine that a change in weight measured by the load sensor 228x may be attributed to a change in the quantity of items associated with the bin that had its lid opened.

In some embodiments, bins may include a tab (not shown) that protrudes outward from a side of the bin and is coupled above and/or below a load sensor, such as load sensor 228x. This enables the connection between the tab and the load sensor to supports the bin. In some embodiments, the tabs of multiple bins may be stacked atop one another and/or placed side by side atop and/or below a surface of the load sensor.

Figure 31:
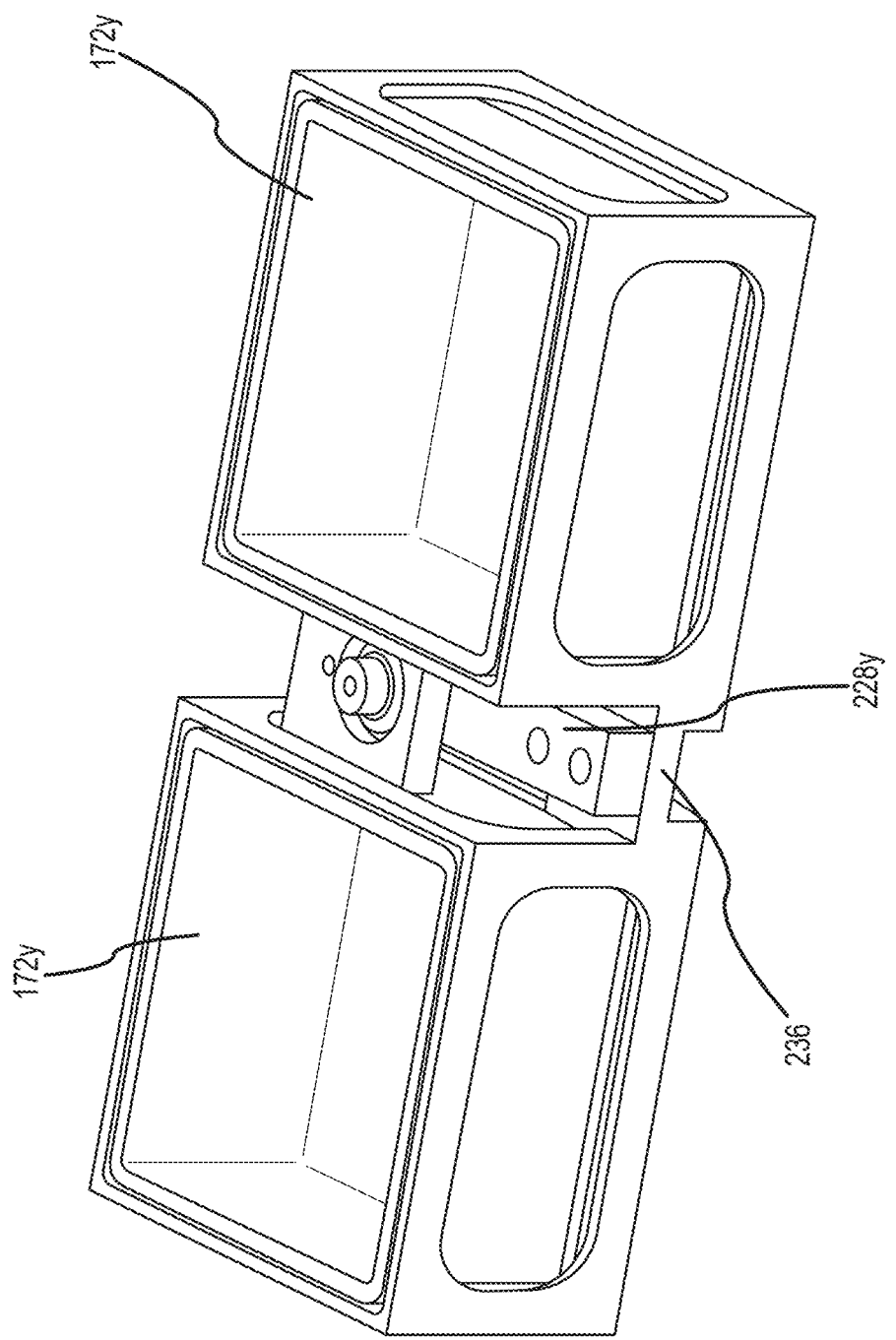
FIG. 31 illustrates two bins sharing a single platform for coupling the bins with a drawer load sensor according to embodiments of the present invention.

As shown in FIG. 31, multiple bins 172y may be formed as a single unit and/or otherwise coupled with a single platform 236 that is positioned over a load sensor 228y, with the load sensor 228y supporting each of the bins 172y.

Figure 32:
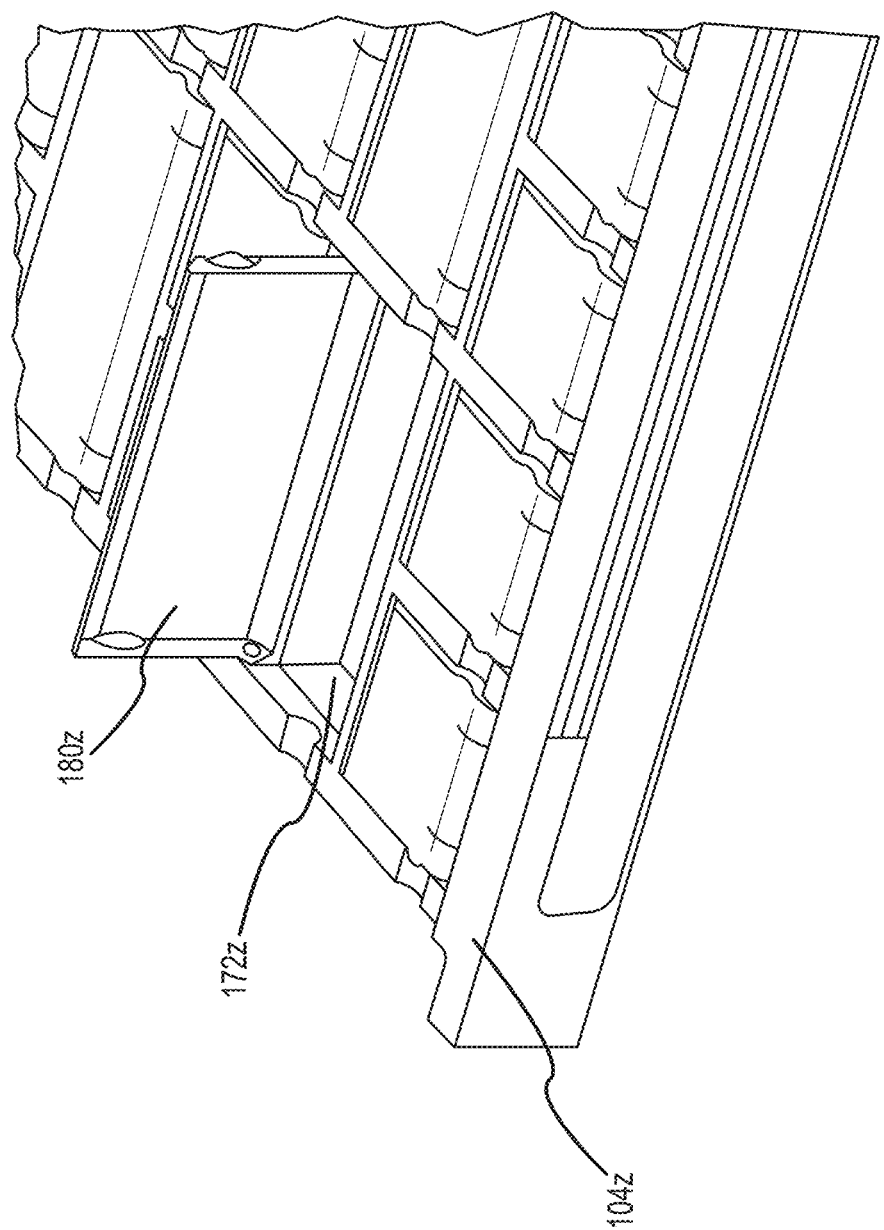
FIG. 32 illustrates a drawer having a number of lidded bins according to embodiments of the present invention.

FIG. 32 illustrates an embodiment of a drawer 104z that includes a number of bins 172z with lids 180z. Bins 172z may be similar to bins 172u described above, and may include one or more sensors, such as imaging sensors and/or load cells that are used to detect the presence of items stored therein. Data from the various sensors allows the inventory of a given bin 172z and/or drawer 104z to be determined.

Image Processing

The image processing techniques described herein may be used in combination with some or all of the embodiments of the application. For convenience of discussion, the techniques may be described in connection with a specific embodiment. In embodiments above that utilize multiple imaging devices, such as those similar to imaging devices 130, various techniques may be used to get the images ready for subsequent object detect. For example, in some embodiments, images from multiple imaging devices with overlapping fields of view may be stitched together to form a single composite image. Typically, such stitching involves identifying common features within the images and aligning the common features to arrange multiple images into a single seamless composite. However, an alternate form of stitching may be possible in embodiments with fixed imaging device positions. For example, the image stitching may be based on known imaging device positions and/or overlap of fields of view of the fixed imaging devices to stitch the images together. More specifically, for a fixed square-shaped array of imaging devices, the computing devices described herein, such as computing device 112, may be programmed to know exactly how much overlap the fields of view of the imaging devices have (which may be dependent on a field of view angle of each imaging device, lateral distance between each imaging device, vertical distance between the imaging devices and the base of a drawer (such as any of drawers 104), bin (such as any of bins 172), and/or items stored within the drawer and/or bin). The computing device 112 may then produce consistently stitched composites without the need to identify common features within the various images.

In other embodiments, rather than relying on stitched images for object detection, the computing devices described herein, such as computing device 112, may utilize object detection to identify complete bins, such as bins 172 (or other partitions) within a single image. For example, inventory control system 100 may include a single imaging device to image a bin 172 or group of bins 172. The computing device 112 may analyze an image to determine which, if any, bins 172 within the image are complete. The computing device 112 may then perform object detection to identify and count items for only the portion of the image that includes a complete bin 172 (a single image may include more than one complete bin 172). For example, the computing device 112 may crop out and/or otherwise ignore portions of each image that do not include full bins 172. In such a manner, object detection for a drawer, such as one of the drawers 104, may involve the computing device 112 analyzing a number of images separately to piece together the contents of the drawer 104. In some embodiments, the computing device 112 may stitch the images together to identify a bin configuration and then analyze the original unstitched images separately for object detection purposes. In other embodiments, a bin configuration may be pre-defined in the computing device 112.

To determine object counts within a drawer 104 or bin 172, the computing device 112 (or another processor that is in communication with the computing device 112) may utilize object detection algorithms to analyze images to identify objects within each image. The computing device 112 may then count the number of each identified object from within the image and update the inventory counts accordingly. These object detection processes may be performed on images from single imaging devices (such as images from a single imaging device of all or part of a drawer 104 and/or bin 172) and/or may be formed from composite images formed from a number of images that have been combined.

As just one example, object detection may involve the computing device 112 identifying bounding boxes containing the various items within a drawer 104 and/or bin 172. Object detection software may look at an entire image and make predictions as to what objects within the image are, with these predictions being informed by the global context in the image. For example, the computing device 112 may be fed information as to the physical characteristics of each item stored within the inventory control system 100, including a size, color, shape, and/or other visually identifiable characteristics.

In some embodiments, a neural network (such as a convolutional neural network) may be used to perform object detection to identify the items within an image. As just one example, a single neural network may apply a detection algorithm to an image to predict both object class labels (a descriptive category of an identified object) and locations of the objects. The algorithm works off by dividing each image into a number of cells. For each cell, bounding boxes and corresponding confidence scores are predicted. Class probabilities are also generated that indicate a predicted classification for each detected object. This classification may be based on a comparison of the characteristics of any identified object with the known visually identifiable characteristics of items that are stored within the inventory control systems described herein, such as inventory control systems 100. The confidence is given in terms of an intersection over union metric, which measures how much a detected object overlaps with the ground truth as a fraction of the total area spanned by the two together (the union). The confidence effectively indicates how likely a computing device, such as computing device 112, thinks an object in the image matches a known item. The loss the algorithm minimizes takes into account the predictions of locations of the bounding boxes, their sizes, the confidence scores for said predictions and the predicted classes. In some embodiments, anchor boxes (pre-determined sets of boxes such that the network moves from predicting the bounding boxes to predicting the offsets from these) may be used to help predict smaller objects within the images.

For example, in one embodiment, an image (or series of images) of a particular size (e.g., (608, 608, 3)) may be input to the computing device 112. The input image may be passed through a convolutional neural network (CNN), resulting in a (19, 19, 5, 85) dimensional output. The neural network may then downsample the image by a factor called the "stride" of the network. Generally, stride of any layer in the network is equal to the factor by which the output of the layer is smaller than the input image to the network. For example, if the stride of the network is 32, then an input image of size 608×608 will yield an output of size 19×19.

After flattening the last two dimensions, the output is a volume of shape (19, 19, 425). Each cell in a 19×19 grid over the input image gives 425 numbers (425=5×85 because each cell contains predictions for 5 boxes, corresponding to 5 anchor boxes) and (85=5+80 where 5 is because (pc, bx, by, bh, bw) has 5 numbers, and 80 is the number of classes intended to detect). Some of the boxes are selected based on a score threshold. For example, the neural network may discard boxes that have detected a class with a score less than the threshold. Non-max suppression may be performed to compute the intersection over union and avoid selecting overlapping boxes. This provides a final output of detected object locations and classes. In the present embodiment, the class of any detected object will be an item stored within the storage region 136 of a drawer 104. The computing device 112 may then count the number of each identified item within the images and update the inventory count based on these values.

RF Detection

In some embodiments, RF tags may be used to track the inventory of one or more drawers. Such RF tags may be used in some or all of the embodiments described herein. For convenience of discussion, reference will be made to inventory control system 100. The RF tags may be used to track the inventory within drawers 104 within the inventory control systems described herein, such as inventory control systems 100. For example, an RFID tag may be affixed to each item to be tracked. Oftentimes, these RFID tags include a pointer (such as a serial number and/or other unique identifier) that identifies the RFID tag. A database may be maintained for each item that includes the pointer and information associated with the item (such as an item description, which may include information such as a type of item, a dose of item, etc.) on which the RFID tag is affixed. When scanned by an RFID reader, the RFID tag returns the pointer, which is usable to reference the item information via the database. In some embodiments, the database may be stored locally on the computing device 112, while in other embodiments the database may be stored on a location that is remote from the computing device 112 but is accessible by the computing device 112 via one or more network connections. The database may also include which RFID tag pointers are in a particular inventory control system 100 and/or drawer 104, allowing the location of all tagged items to be monitored. The database may be updated each time the drawer 104 is accessed, both for restocking and removal purposes. In this manner, a constant inventory of the drawer 104 and inventory control system 100 are maintained in the database (or another database). In some embodiments, the RFID tags may be more sophisticated and may include additional information about the item that is encoded directly on the RFID tag. Such information may be password protected and/or encrypted if additional security is required.

Figure 33:
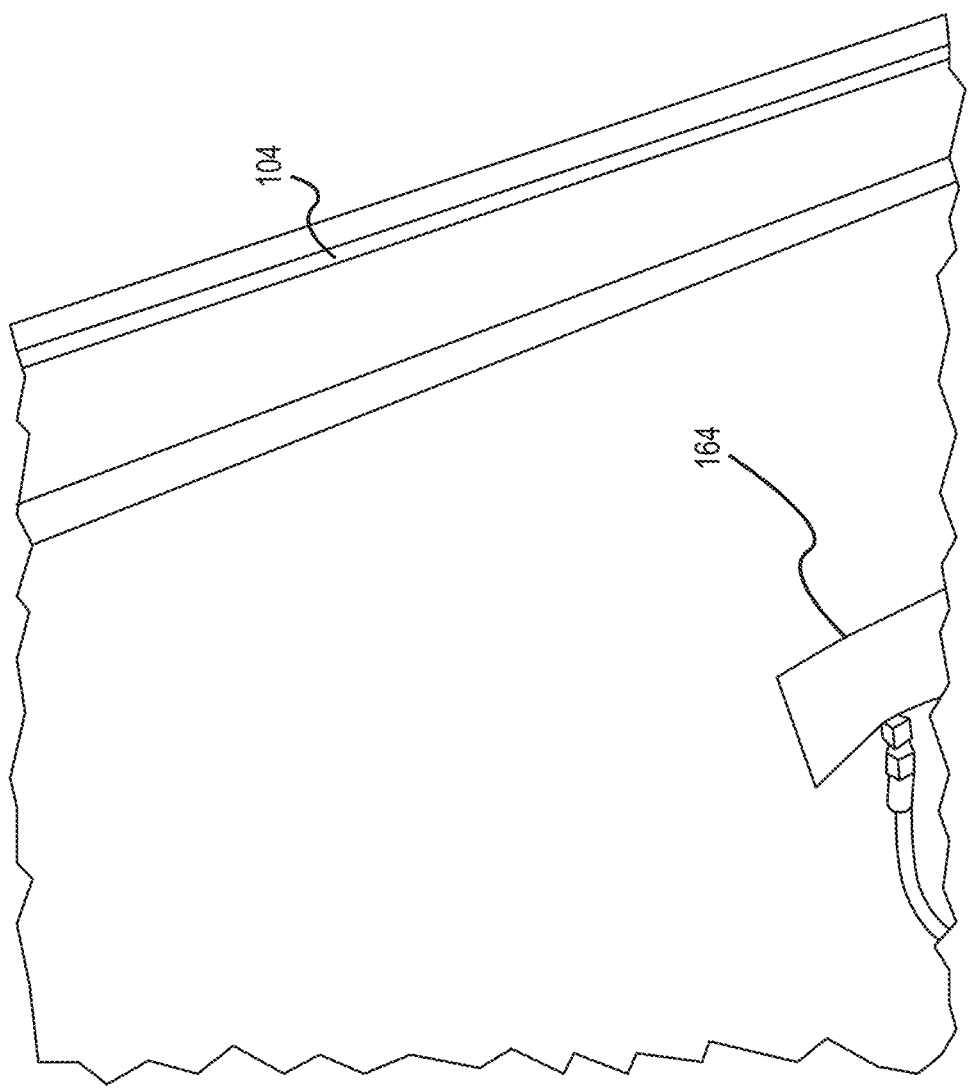
FIG. 33 illustrates a radio frequency identifier (RFID) antenna affixed to a drawer of an inventory control system according to embodiments of the present invention.

In RFID embodiments, one or more of the drawers described herein, such as drawers 104, may include one or more RFID antenna 164 as shown in FIG. 33. These RFID antennae are coupled to at least one RFID reader for receiving and decoding the information from RFID tags of items positioned within the drawer 104. Inventory may be taken of each drawer 104 by detecting the presence of each RFID tag within the drawer 104 and comparing the serial number to serial numbers that were previously associated with the drawer 104. The inventory control system 100 determines that any missing serial numbers belong to items that have been removed from the cabinet. The items that have been determined to have been removed may be compared to the items selected for removal at the computing device 112 by the user. Any discrepancies may be flagged and one or more entities may be notified, which may lead to an investigation as to the cause of the discrepancy.

In some embodiments, to prevent the antenna 164 for one of the drawers 104 from detecting RFID tags from other drawers, each drawer 104 may include RF shielding that prevents any RF signals from passing through. For example, in some embodiments each drawer 104 may include an RF shielding lid or film applied over the storage region 136 of the drawer 104 while positioning an RF antenna 164 in or below the base of the drawer 104. Such an arrangement prevents RF signals from passing through a top of the drawer 104, but allows the RF antenna to communicate with RFID tags positioned within the drawer 104. In other embodiments, a base of the drawer 104 may include RF shielding, while the antenna 164 is positioned above the RF shielding. This allows the RF antenna 164 to detect RFID tags within the drawer 104 while preventing RF communication with anything below the RF shielding. In some embodiments, a single antenna, such as antenna 164, may be used to detect items within multiple drawers 104. In such embodiments, RF shielding may be put in place about the boundaries of the subset of the drawers 104 with which the antenna 164 is associated.

Load Cells

In some embodiments, the weight of items stored within a drawer, such as drawers 104, and/or bin may be used to determine what items are present/have been removed. The weighing techniques described herein may be used with any of the embodiments described herein. However, for convenience of discussion, reference will be made to the embodiment of FIGS. 1A and 1B As one example, each of the drawers 104a and/or bin may be associated with a particular type of item (such as a tool, medication type, and/or other item). A database in a computing device, such as computing device 112, may include information about the items associated with a given drawer 104a and/or bin. This information may include a weight associated with each item. As the drawer 104a and/or bin is filled, refilled, and/or items are removed, the computing device 112 may determine which item counts have changed based on changes to the measured weight. For example, a drawer 104a may include four different types of items, each having a different weight. As one or more items are added or removed, weight sensors may detect changes in weight of the drawer 104a and determine which and how many items have been added or removed.

In some embodiments, a drawer, such as drawers 104a, and/or bin may include a single weight sensor, such as a capacitance sensor, for detecting changes in weight of the drawer 104a and/or bin. The capacitance sensor may include two metal plates that are separated by a thin layer of inert material (such as, but not limited to, a foam). This sensor may be positioned in the base of the drawer 104a and/or bin such that items placed within the drawer 104a and/or bin sit atop the capacitance sensor. As the load within the drawer 104a and/or bin changes, a distance between the metal plates of the sensor changes (e.g., shortens when the load increases and lengthens when the load decreases). This change in distance causes a change in capacitance between the two plates, which is then converted into a weight measurement. In other embodiments, strain load cells may be utilized in a similar manner.

Figure 34A:
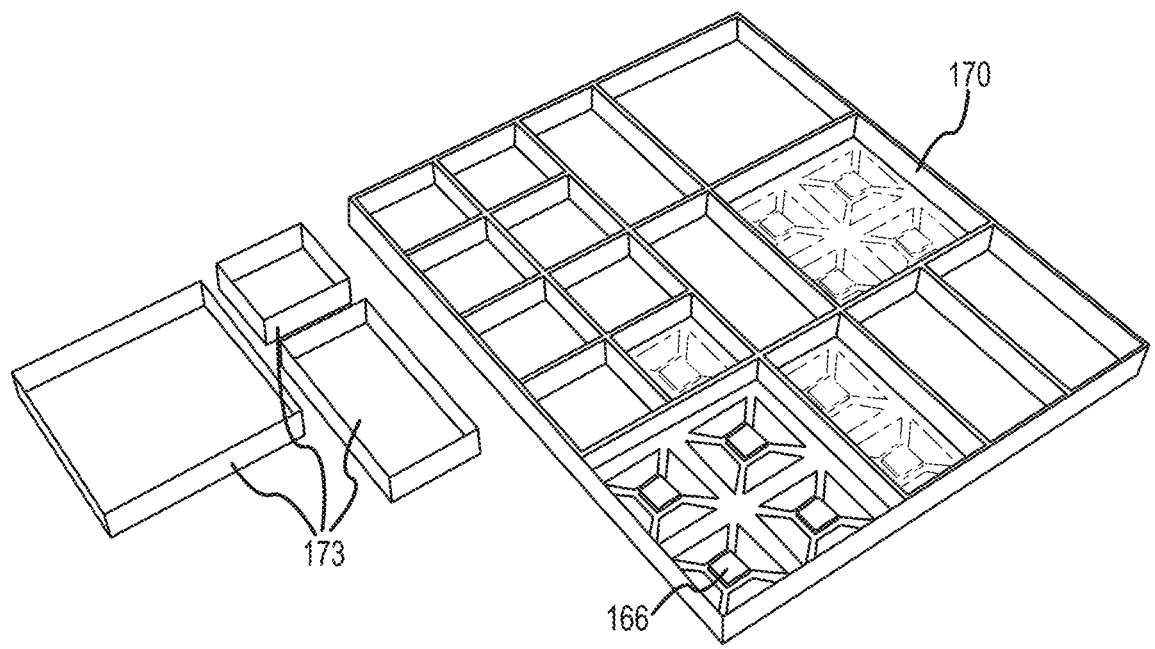
FIG. 34A illustrates an open matrix drawer arrangement including a number of load sensors according to embodiments of the present invention.
Figure 34B:
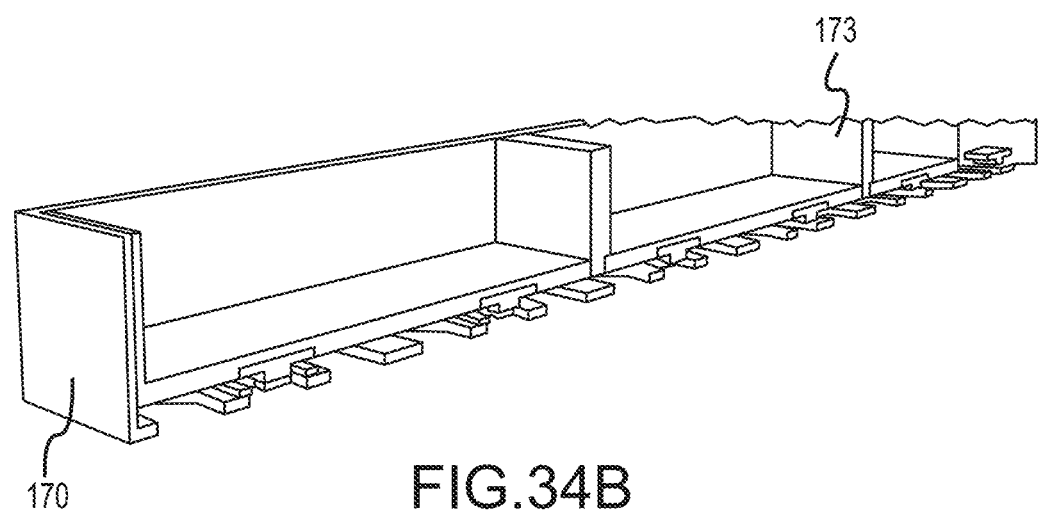
FIG. 34B illustrates a cross-sectional view of the open matrix drawer arrangement of FIG. 34A.
Figure 34C:
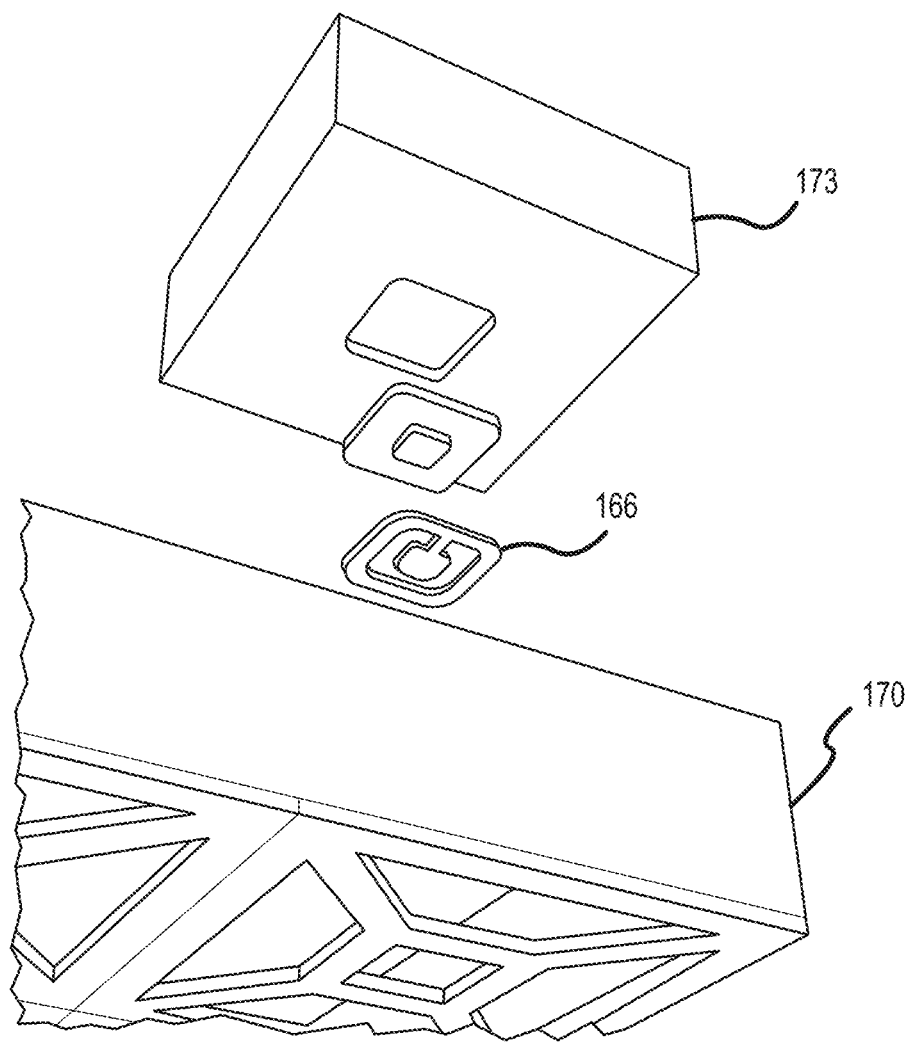
FIG. 34C illustrates an exploded view of the open matrix drawer arrangement of FIG. 34A.

In other embodiments, multiple load sensors may be utilized to detect changes in weight of a drawer, such as drawers 104, and/or bin. Oftentimes, when multiple load sensors are used, strain load cells are used, although other load cells (such as capacitive sensors) may be utilized in a similar manner. In embodiments with multiple load sensors, an open matrix array of load cells 166 is provided within a base of a drawer, such as drawers 104a of FIGS. 1A and 1B, as illustrated in FIGS. 34A-34C. Here, a number of high accuracy strain gauges 166 are arranged in an open matrix in a drawer frame 170. As illustrated, the drawer frame 170 includes a symmetrical layout of load cells in the form of strain gauges 166 that provide coverage for the entire base of the drawer frame 170, although in other embodiments other arrangements of strain gauges and/or other load sensors is possible. The drawer frame 170 then supports a number of bins 173, (which may be similar to any of the bins described herein), and/or container modules that may be arranged atop the drawer frame 170. The bins 173 may be open top bins and/or lidded and/or locked bins. A given drawer frame 170 may include bins 173 of uniform size and/or shape or may have a mix of bins 173 of different sizes and/or shapes. In some embodiments, the bins 173 are arranged to a predefined layout, while in other embodiments a user may customize the layout of the bins 173 within the drawer frame 170. In some embodiments, the bins 173 may sit atop the strain gauges 166, while in other embodiments the strain gauges 166 are at least partially received within a base of the bin 173. For example, as shown in FIG. 34C a base of the bin 173 defines a recess that receives the strain gauge 166, which is also interfaced with the drawer frame 170.

By providing each bin 173 with a dedicated set of one or more strain gauges (or other load sensors), a more accurate count of items added or removed is possible. In such embodiments, each bin 173 may be configured to store a single type of item. A computing device, such as computing device 112, may access or include a database that includes a type of item associated with each bin 173, a weight of each individual item, and a set of load sensors associated with the bin 173. This allows the computing device 112 to quickly determine what and how many items have been added or removed at any given time. For example, the computing device 112 may detect that load sensors associated with a first bin 173 have detected a reduction in load of 50 grams. The computing device 112 may determine that the items associated with the first bin 173 are a type of medication vial that weigh 12.5 grams per vial. The computing device 112 may then determine that four vials of the medication were taken from the first bin 173b based on this information.

FIGS. 35A-35C illustrate another embodiment of an open-topped bin 172' having one or more load sensors 238. Here, a drawer 104' is illustrated having a configurable interior. For example, each of the sidewalls 240 of the drawer 104' defines a notch 242 that is configured to receive and secure a partition 244. As illustrated in FIG. 35A, a notch 242 is formed at a center of each sidewall 240, allowing the interior of the drawer 104' to be divided into one, two, three, or four bins 172' depending on the placement of the partitions 244. It will be appreciated that numerous other arrangements of drawers 104o may be utilized to provide any combination of sizes and/or shapes of bins 172'. As illustrated in FIGS. 35B and 35C, a number of load sensors 238 may be positioned beneath a base 105 of the drawer 104'. For example, an array of load sensors 238 may be distributed about a surface of the drawer 104'. The array may include any arrangement of load sensors 238. Oftentimes, the load sensors 238 may be in a symmetrical arrangement such that regardless of how the bins 172' are configured, each bin 172' includes at least one dedicated load sensor 238, with larger bins 172' being positioned atop multiple load sensors 238 in some embodiments.

As removal or addition of items are detected, an inventory of the items may be updated to account for the detected changes. For example, a comparison of the detected contents of a drawer, such as drawer 104, and/or a bin, such as bin 172, from two different points in time may be compared to determine what item counts have changed. In some embodiments, a computing device, such as computing device 112, may measure the load right before a user is granted access to a drawer 104 and/or bin 172 and right after the user has finished accessing the drawer 104 and/or bin 172. This allows the inventory to be accurately monitored without needing to account for long term drift of loads detected by the load sensors. In other embodiments, the loads and inventory may be monitored only when the drawer 104 and/or bin 172 is closed. In some such embodiments, the load sensors may be activated when the drawer 104 and/or bin 172 is detected as being in a closed state. In some embodiments, locking of the drawer 104 and/or bin 172 triggers the activation of the load sensors. In some embodiments that utilize open-topped bins 172, each bin may include a light sensor and/or motion detector, such as a light curtain, that may be positioned within an interior of the bin 172. This light sensor may be used to detect when a user's hand accesses the bin 172 and takes or replaces an item. The load sensors may be triggered based on this detection. In some embodiments, discrepancies between what items were detected as removed or added and a user's selections of items prior to accessing a given drawer 104 and/or bin may be noted and flagged for later investigation.

To restock an open-topped bin, such as an open-topped version of bin 172, that includes one or more load sensors, a user may input a quantity of items present within in a particular bin 172 at the end of restocking the bin 172. Software of an inventory control system, such as the inventory control systems 100, then measures the weight of the bin 172 and/or contents thereof and calculates the quantity of items using a known expected per item weight. The inventory control system then compares the calculated quantity to the quantity provided by the user. If the two quantities match, the restock process ends. If the two quantities do not match, the software of the inventory control system 100 will prompt the user to empty the bin 172, re-tare and/or otherwise reset the load sensor, weigh and re-count, and/or accept the user count. In some instances, mismatched quantities may be a result of a change in the item (e.g., a new type and/or size of item has been placed in the bin 172 without updating the records of the inventory control system 100), a sensor shift, and/or user miscount. Once a discrepancy has been resolved, the discrepancy, decided resolution, and/or any reconciliations of mismatched quantities may then be logged for future use.

In some embodiments, the load sensors may detect changes in load that are not the result of items being added or removed. In such instances a computing device, such as computing device 112, may need to be able to determine that such changes should be discarded rather than being used to adjust the inventory count of a particular item. For example, if a load measurement spikes beyond a normal range and/or is not consistent with an expected load increment (such as if the weight of a bin full of 50 gram items changes by 25 grams, it may be determined that an error has occurred and the spike or load value may be ignored. In some embodiments, if such an error occurs, a user (the logged in user and/or another user such as a technician) may be notified (such as by an indication being presented on a display screen (such as display screen 114) and/or other output device, and/or by alerting a remote device over one or more network connections). This alerts the user to quickly determine the source of the error and rectify any issues.

Oftentimes load sensors are quite delicate and may be damaged if subjected to excessive force, which may occur when a drawer, such as drawers 104, is opened or closed. Therefore, some embodiments may include force dampening mechanisms that help protect the integrity of the load sensors. As just one example, the drawer 104 may be fitted with a soft close and/or open mechanism that limits the opening and/or closing speed of the drawer 104. In some embodiments, the speed of the drawer 104 may be regulated along its entire movement range, while in other embodiments the speed may be regulated only near ends of the range of motion, such as within 10% or 20% of the end of the range of motion in one or both directions.

In other embodiments, a releasable coupling mechanism may be used in conjunction with the load sensors that disengages the load sensor when a drawer, such as drawers 104, is open and reengages the load sensor once the drawer 104 has been closed. For example, a mechanical lift mechanism may be used to elevate bins, such as bins 172, when the drawer 104 is opened to keep the load sensors disengaged. The lift may be deactivated once the drawer 104 is closed, allowing the bins 172 to again sit atop the load sensors. Other disengagement mechanisms such as locks and/or solenoids may be utilized when the drawer 104 is in motion and/or in the open position to prevent lateral movement and force from affecting the integrity of the load sensors.

Smart Surface

In some embodiments, a work surface, such as work surfaces 106, may be a smart surface that includes a number of integrated sensors that further enhance the ability of the inventory control system 100 to track which items have been removed, used, returned, and/or wasted. Oftentimes, the information gathered from these additional sensors may be used in conjunction with data from one or more sensors associated with individual drawers (such as drawers 104) and/or bins (such as bins 172) to reconcile previously sensed data and increase the accuracy of inventory counts as is described in greater detail below. While such a work surface may be used with any of the embodiments described herein, for convenience of discussion particular reference will be made to FIG. 1A.

In some embodiments, the work surface 106 may utilize one or more weight sensors 108 (see FIG. 1A) that may be used to weigh any items placed upon the work surface 106. The weight sensors may be similar to the load sensors described above. Additionally, the weight sensors may be used to extract size information and/or a pressure map of contact points of items on the work surface 106. This size information and/or pressure map may be used to assist with item identification by comparing the size and/or pressure shape of an item to known item characteristics. The work surface 106 may include an RF antenna and RFID reader that allows the work surface 106 to detect any nearby items that include RFID tags. In some embodiments, the work surface 106 may include a transparent surface covering some or all of the work surface 106. One or more imaging devices and/or other imaging devices may be positioned beneath the transparent base and may image items that are placed atop the transparent surface. In other embodiments, one or more imaging devices and/or other imaging sensors may be mounted above the work surface 106 to image items positioned thereon.

In some embodiments, one or more items within an inventory control system, such as the inventory control systems 100, may include barcodes and/or other computer-readable identifiers that store or point to information associated with the item in a manner similar to the RFID tags described herein. In some embodiments, the work surface 106 may include a barcode reader and/or other optical reader to scan and decode this information. In some embodiments, the barcode reader may be in the form of an omnidirectional optical reader 110 (see FIG. 1A) that is able to read the barcode from numerous angles. In some embodiments, the omnidirectional optical reader 110 may be integrated into a recess defined within the work surface 106. The recess may include an imaging device (such as an imaging device, infrared sensor, and/or barcode reader) that is configured to image all sides of the recess. For example, if the recess is cylindrical in shape, the imaging device may scan 360 degrees within the interior of the recess. It will be appreciated that other arrangements and locations of the omnidirectional reader 110 are possible in some embodiments.

In operation, a user (such as an anesthesiologist and/or other medical personnel) may "dip" the medication or other item into the recess. The imaging device is used to identify the item. For example, the imaging device may be an imaging device and/or barcode scanner that is configured to read human readable (such as text) and/or machine readable (such as a barcode, QR code, and/or other machine readable format) information from the surface of the item. In some embodiments, this information may include a lot number and/or expiration date of the item. An inventory control system, such as one of the inventory control systems 100, may perform any number of checks based on this information. For example, the inventory control system 100 may determine whether the particular item (such as a medication) is appropriate for a given patient, whether the lot of the item has been recalled, whether the item has expired, etc. In instances where the item is a medication, reading of the information may optionally trigger the printing of a label. For example, the item may be a vial of liquid medication. A barcode or other identifier may be read, and the information read from the barcode may trigger a printer to print a label to be applied on a syringe. The user may then, in some order, affix the label to a syringe and draw a correct dosage of medication out of the vial using the syringe. In this manner, the user may be able to quickly prepare syringes of medications that are properly identified and labeled.

While discussed primarily in terms of using optical imaging sensors, some embodiments may utilize RF sensors (either in place or in addition to using imaging sensors). For example, an RF antenna may be positioned within the recess and may be configured to only read items placed within the recess. For example, the walls and/or base of the recess may include RF shielding materials to prevent the RF antenna from detecting items outside of the recess. In some embodiments, a power of the RF antenna may be adjusted such that a detection range of the RF antenna completely matches or substantially matches the volume of the recess. Items containing RF tags may be dipped into the recess and data from the RF tags may be read by the RF antenna and a corresponding RF reader. This data may be similar to the information read from using imaging devices and may be similarly used to determine whether the particular item (such as a medication) is appropriate for a given patient, whether the lot of the item has been recalled, whether the item has expired, and/or be used to print a label for a syringe.

FIGS. 36A and 36B illustrate one embodiment of an omnidirectional reader 110*a*. Omnidirectional reader 110*a* includes one or more imaging devices 202 disposed proximate a bottom of a recess 200*a*. Imaging device 202 may be an imaging device, barcode reader, and/or other optical sensor. The imaging device 202 is directed upward to capture and read images of items that are dipped into the recess 200*a*. In the present embodiment, the walls of the recess 200*a* include a reflective surface 204, such as a mirrored surface. To image all or most of the sides of the item, the imaging device 202 has a field of view that is sufficiently wide to extend laterally outward to capture reflections from the reflective surface 204 in some or all directions. By capturing the reflections, the imaging device 202 effectively extends its field of view to capture some or all sides of a given item placed within the recess 200*a*.

In some embodiments, the omnidirectional reader 110*a* may include one or more lighting elements. For example, LEDs 206 and/or other lighting elements may be placed on or near a base of the recess 200*a*. LEDs 206 may provide light to assist with the image capture by the imaging device 202. As illustrated, the LEDS 206 are arranged in an annular pattern about the imaging device 202 and directed upward to illuminate the interior of the recess 200*a*, however other arrangements of LEDs 206 are possible. In some embodiments, the omnidirectional reader 110*a* may include a status indicator 208. As illustrated, status indicator 208 is in the form of an annular light that extends around an upper periphery of the recess 200*a*. The annular light may illuminate in a predetermined, color, pattern, and/or other manner to alert a user of the status of the omnidirectional scanner 110*a*. As just one example, the status indicator 208 may emit red light to indicate that no item has been detected, blue light to indicate that an image capture or scan is underway, and green light to indicate that the image capture/scan process is complete. It will be appreciated that other color schemes/status mechanisms are possible. In other embodiments, the status indicator 208 may be integrated into an interior of the recess 200*a*. For example, one or more lights may illuminate the interior of the recess 200*a* with light of a particular color and/or pattern to indicate the status of a scan. In some embodiments, LEDs 206 may be utilized to produce such light. It will be appreciated that the status indicator 208 may be positioned remote from the recess 200*a* in some embodiments, such as on a GUI of a computing device, such as computing device 112, and/or on another surface of an inventory control system, such as one of the inventory control systems 100. In some embodiments, in addition to or in place of the lighting elements, the status identifier 208 may include a speaker that is configured to generate an audible sound that indicates a status of the scan. In some embodiments, the sound may be a recorded sound such as a chime or buzzer, while in other embodiments the sound may involve prerecorded and/or machine produced voice messages.

Figure 37:
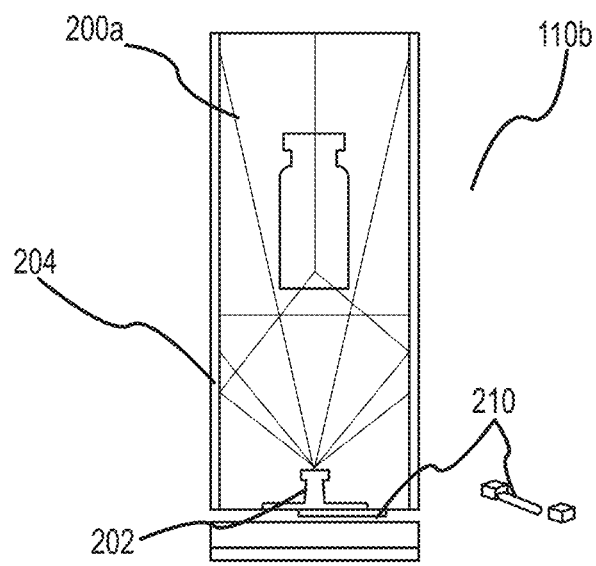
FIG. 37 illustrates a side view of an omnidirectional reader having a central imaging device and a load sensor according to embodiments of the present invention.

In some embodiments, the omnidirectional reader 110 may include various other sensors. For example, as illustrated in FIG. 37, the omnidirectional reader 110*b* includes one or more load sensors 210 integrated into and/or positioned beneath a base of the recess 200*a*. The embodiment of FIG. 37 is substantially the same as the embodiment of FIGS. 36A and 36B with the exception of load sensors 210, thus the same reference numerals will be used in describing FIG. 37 with the exception of the load sensors 210. A user may place an item in the recess 200a atop the base/load sensor 210 and the load sensor 210 can measure the weight of the item. Based on the measured weight, an inventory control system, such as one of the inventory control systems 100, may determine the identity of the item. Based on the identification of the item, in some embodiments, the load sensors 210 may be integrated into an omnidirectional reader 110b that includes additional sensors. For example, the omnidirectional reader 110b may include an imaging device 202 such as described above, and may also include a reflective surface 204, LEDs 206 and/or status indicator 208. When used in conjunction with one another, the load sensor 210 and the imaging device 202 may operate to not only identify an item, but may also be utilized to complete a waste procedure. For example, the imaging device 202 may be utilized primarily to identify the item. Once a portion of the item has been withdrawn or used (such as when a user extracts a volume of liquid medication from a vial using a syringe) the remaining item may be weighed to determine the quantity being wasted and/or the quantity that was withdrawn. This may be done, for example, by the inventory control system 100 retrieving information about the identified item from local and/or remote storage and comparing a known expected weight of the item to the measured weight. Based on a change in the weight, as well as information about the item and/or its contents, the inventory control system 100 may calculate the used or wasted amount of the item.

Figure 38B:
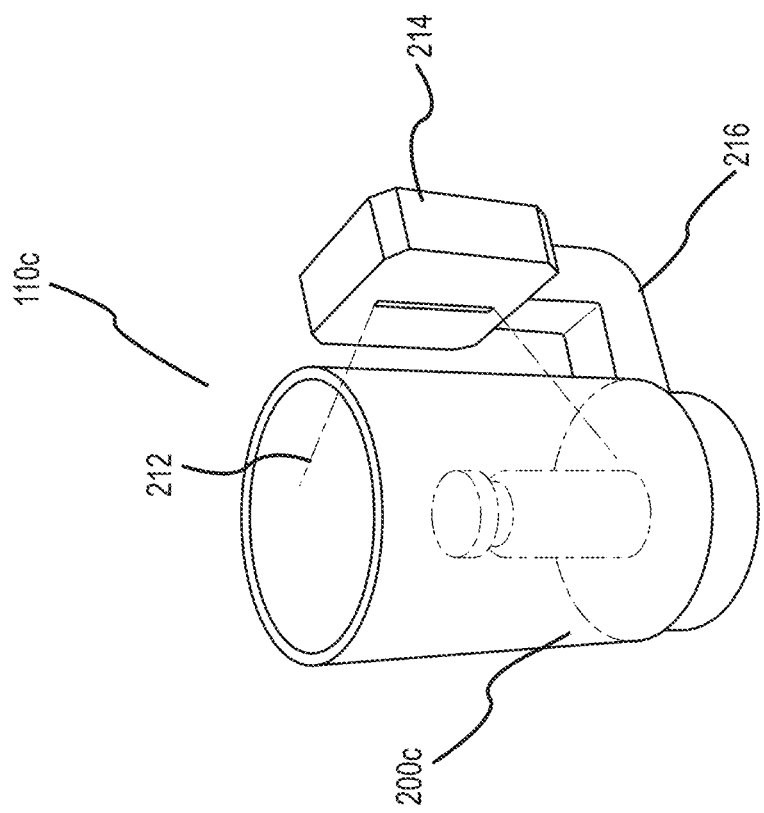
FIG. 38B illustrates a side elevation view of the omnidirectional reader of FIG. 38A.
Figure 38A:
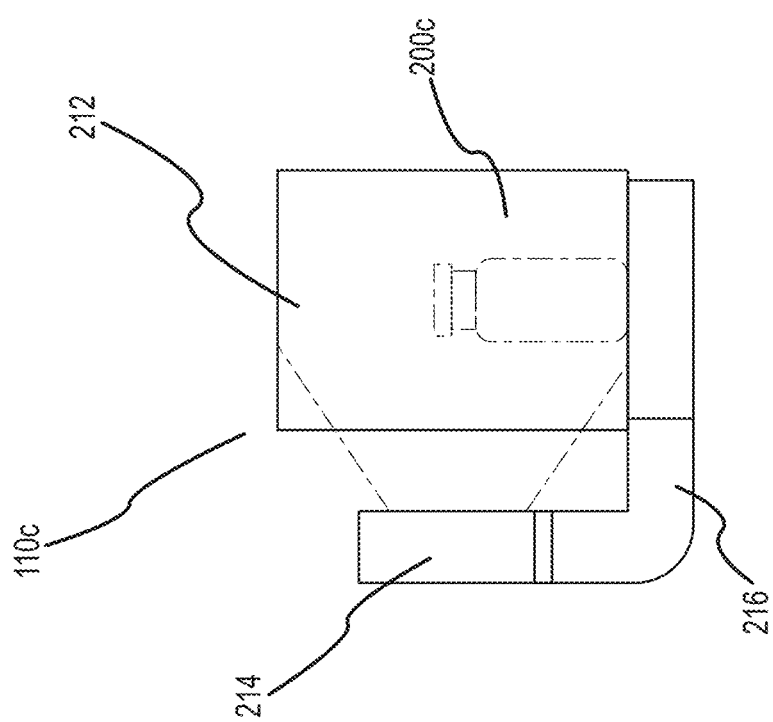
FIG. 38A illustrates a perspective view of an omnidirectional reader having a rotating imaging device according to embodiments of the present invention.

FIGS. 38A and 38B illustrate another embodiment of an omnidirectional reader 110c. As illustrated, the recess 200c includes transparent sidewalls 212. A rotating imaging device 214 (such as a camera, barcode scanner, line scanner, etc.) may be positioned outside of the transparent sidewalls 212 and may be configured to rotate about the recess 200c. As illustrated here, the rotating imaging device 214 is positioned in horizontal alignment with the recess 200c and has a field of view that extends vertically to cover all or substantially all of a depth of the recess 200c. The rotating imaging device 214 is coupled with the recess 200c via an arm 216 that extends downward from the rotating imaging device 214 and couples below a base of the recess 200c. A motor (not shown) is used to rotate the arm 216 and rotating imaging device 214 about all or a substantial periphery of the recess 200c. It will be appreciated that other arrangements of rotating imaging devices may be utilized in some embodiments. In operation, the rotating imaging device 214 may be rotated about all or a substantial periphery of the recess 200c to image all or most of an item that has been placed in the recess to read information that is usable to determine whether the particular item (such as a medication) is appropriate for a given patient, whether the lot of the item has been recalled, whether the item has expired, and/or be used to print a label for a syringe. While not illustrated, it will be appreciated that omnidirectional reader 110c may also include any combination of LEDs 206, status indicator 208, and/or load sensors 210.

Figure 39A:
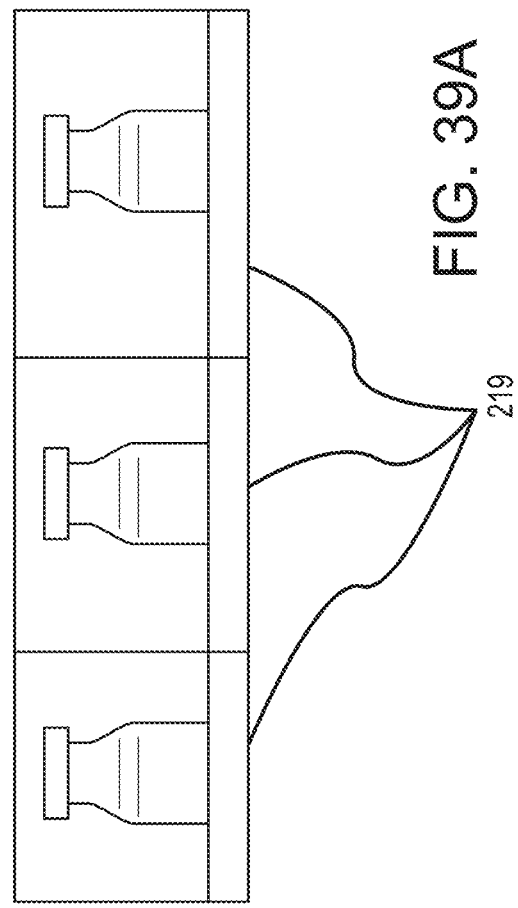
FIG. 39A illustrates a set of images of an item captured by the omnidirectional reader of FIG. 39.
Figure 39:
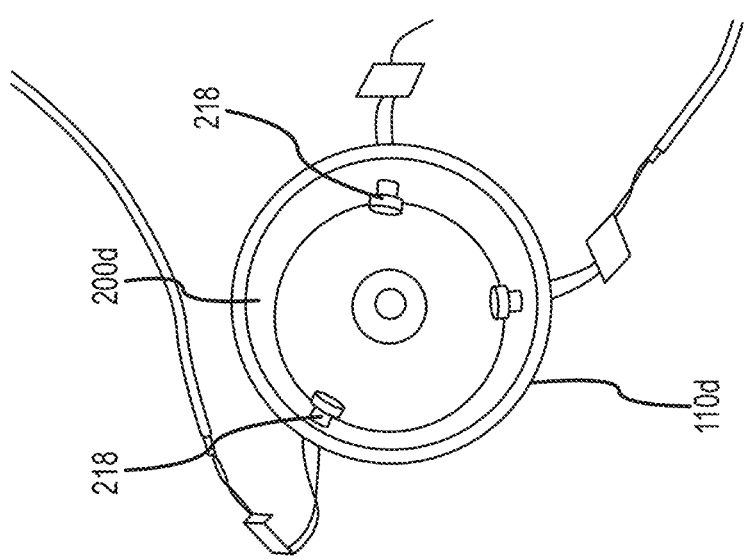
FIG. 39 illustrates a top view of an omnidirectional reader having three fixed imaging devices radially spaced about a recess according to embodiments of the present invention.

FIG. 39 illustrates another arrangement of an omnidirectional reader 110d. Here, the omnidirectional reader 110d includes three imaging devices 218 positioned at equal intervals around the recess 200d. As illustrated, the lens of each imaging device 218 extends through walls 220 of the recess 200d at fixed positions and points toward an interior of the recess 200d. In other embodiments, the walls 220 may be transparent and each of the imaging devices 218 may be positioned outside of the walls 220 and facing inward. Each of the imaging devices 218 may have a wide angle lens, allowing the image fields of the imaging devices 218 to overlap so as to cover all or a substantial portion of the interior of the recess 200d. Each imaging device 218 may image items positioned within the recess 200d. In some embodiments, the imaging devices 218 may always be in an imaging mode, while in other embodiments the imaging devices 218 may be activated by a user interaction (such as a button press) and/or automatic detection using a proximity sensor and/or one or more of the imaging devices 218.

FIG. 39A illustrates a set of images 219 of an item captured by the imaging devices 218 of the omnidirectional reader 110d. Here, each image 219 is of a portion of the item. These images may be analyzed individually and/or stitched together and analyzed together to identify an item within the image and information about the item. This information may be used to determine whether the particular item (such as a medication) is appropriate for a given patient, whether the lot of the item has been recalled, whether the item has expired, and/or to print a label for a syringe. While not illustrated, it will be appreciated that omnidirectional reader 110d may also include any combination of LEDs 206, status indicator 208, and/or load sensors 210.

Figure 40B:
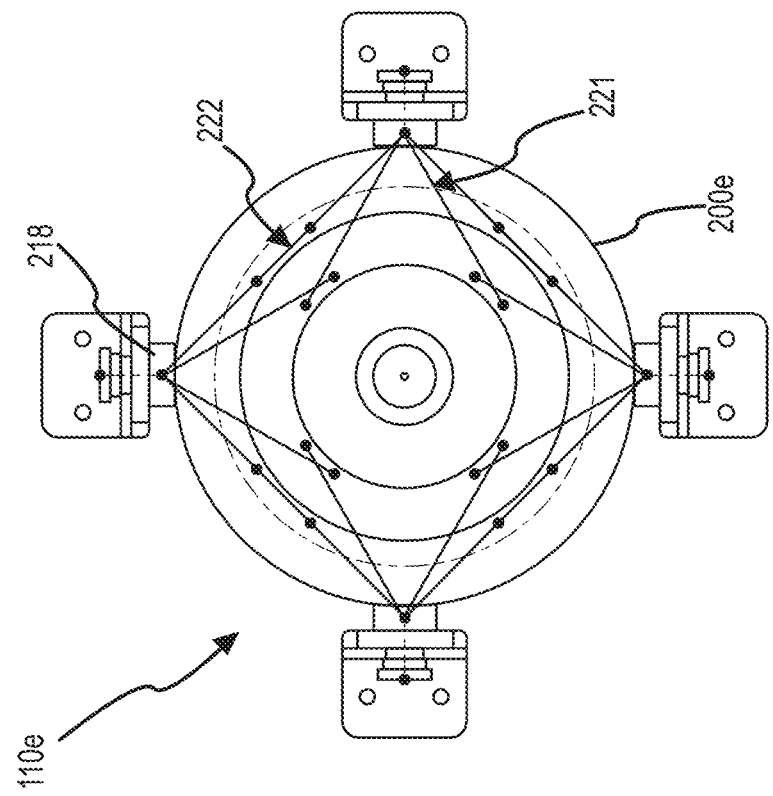
FIG. 40B illustrates a top view of the omnidirectional reader of FIG. 40A.
Figure 40A:
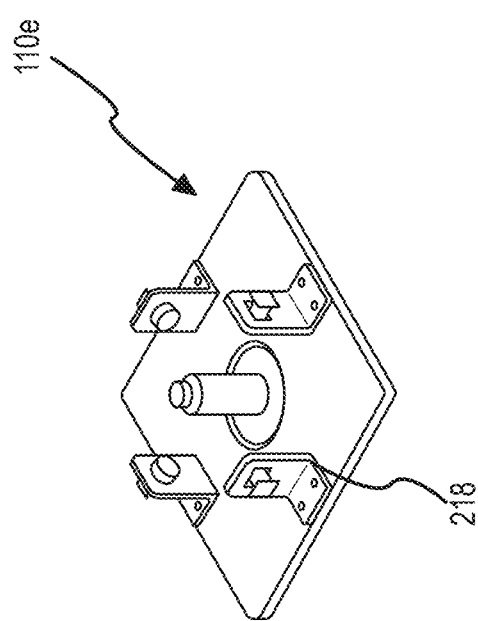
FIG. 40A illustrates a perspective view of an omnidirectional reader having four fixed imaging devices radially spaced about a recess according to embodiments of the present invention.
Figure 41B:
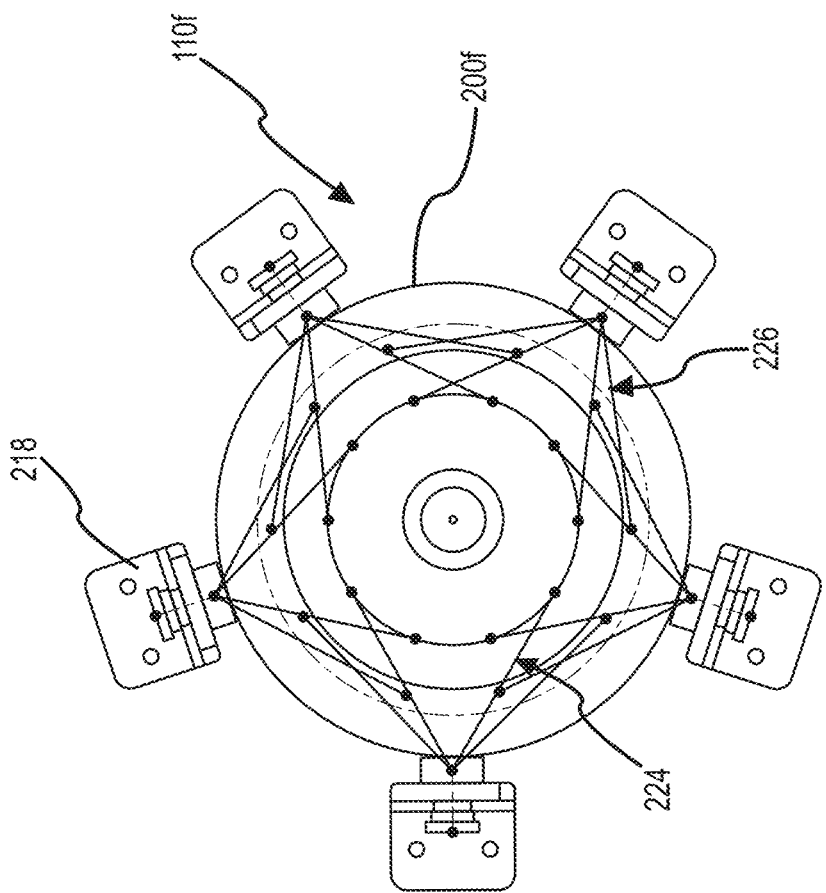
FIG. 41B illustrates a top view of the omnidirectional reader of FIG. 41A.
Figure 41A:
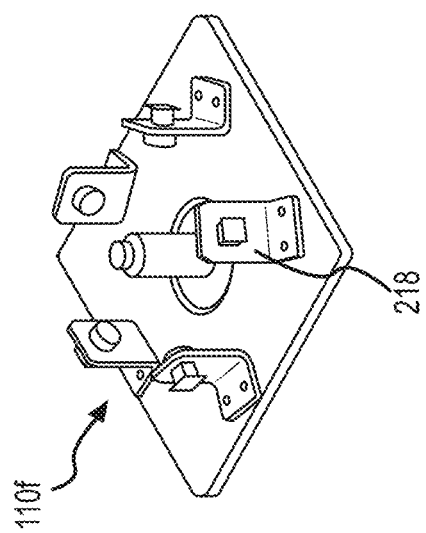
FIG. 41A illustrates a perspective view of an omnidirectional reader having five fixed imaging devices radially spaced about a recess according to embodiments of the present invention.
Figure 42B:
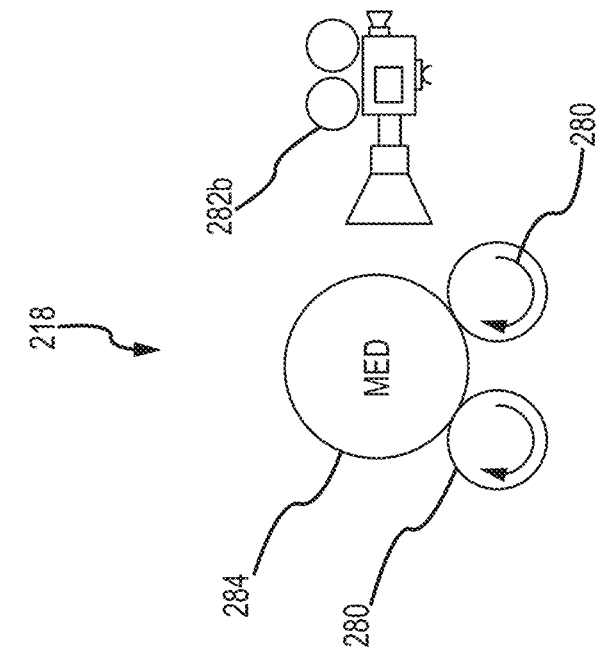
FIG. 42B illustrates a side view of an alternate embodiment of an omnidirectional reader having a laterally facing imaging device according to embodiments of the present invention.
Figure 42A:
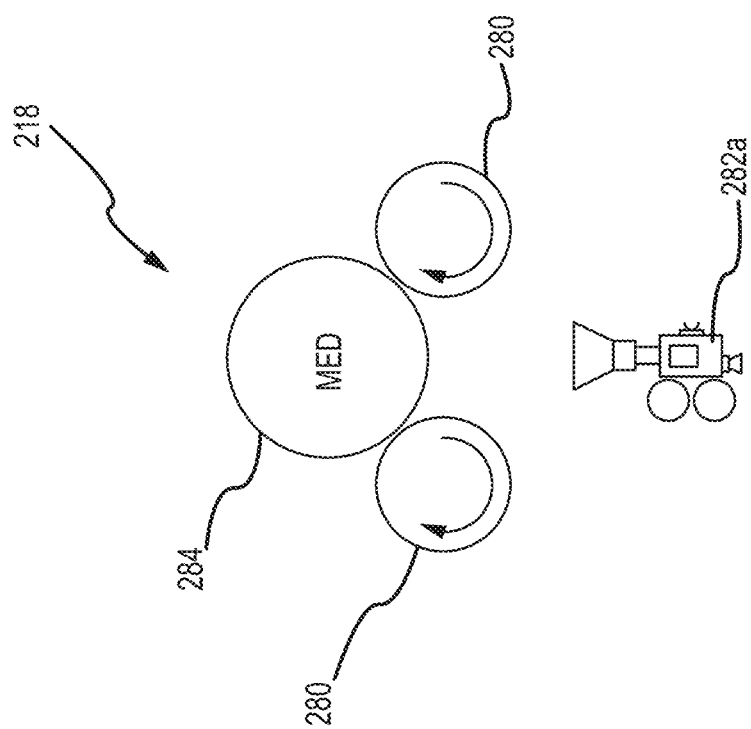
FIG. 42A illustrates a side view of an alternate embodiment of an omnidirectional reader having an upward facing imaging device according to embodiments of the present invention.

It will be appreciated that any number of imaging devices 218 may be positioned about the periphery of the recess 200, with greater numbers of imaging devices 218 providing greater coverage and/or reducing the field of view width needed for each imaging device 218. FIGS. 40A and 40B illustrate an arrangement of an omnidirectional reader 110e that operates in the same manner as the omnidirectional reader 110d, but has four imaging devices 218 rather than three. As illustrated in FIG. 40B, as the field of view of each imaging device 218 is increased, a greater proportion of the recess 200e may be imaged and a larger item size may be handled. As just one example, for a recess 200e having a circumference of 75 mm, imaging devices 218 having a field of view of 60 degrees are capable of imaging an item having a maximum circumference of about 36 mm as illustrated by arrows 221, while imaging devices 218 having a field of view of 90 degrees are capable of imaging an item having a maximum circumference of about 52 mm as illustrated by arrows 222. FIGS. 41A and 41B illustrate an arrangement of an omnidirectional reader 110f that operates in the same manner as the omnidirectional readers 110d and 110e, but has five imaging devices 218. As illustrated in FIG. 41B, as the field of view of each imaging device 218 is increased, a greater proportion of the recess 200f may be imaged and a larger item size may be handled. As just one example, for a recess 200f having a circumference of 75 mm, imaging devices 218 having a field of view of 60 degrees are capable of imaging an item having a maximum circumference of about 40 mm as illustrated by arrows 224, while imaging devices 218 having a field of view of 90 degrees are capable of imaging an item having a maximum circumference of about 54 mm as illustrated by arrows 226. FIGS. 42A and 42B illustrate another embodiment of an omnidirectional reader 110g. Omnidirectional reader 110g may include two rollers 280 that are driven by a motor (not shown). A user may place an item 284 on the rollers 280, which may rotate one or more revolutions to fully rotate the item 284. An imaging device 282a, such as a camera or barcode reader is aimed at a space that is configured to receive the item 284. The imaging device 282a is then used to image the item 284 and/or read a barcode. In some embodiments, the imaging device 282a may be positioned below the rollers 280 and aimed at a gap formed between the rollers 280 such that the imaging device 282a images a portion of the item 284 that is visible between the rollers 280 such as illustrated in FIG. 42A. In other embodiments, an imaging device 282b may be alongside one of the rollers 280 and aimed at a position directly above the rollers 280 such that the imaging device 282*b* images a portion of the item 284 that is visible above the rollers 280 such as illustrated in FIG. 42B.

In another embodiment, not illustrated, an omnidirectional reader, similar to omnidirectional reader 110*g*, may include multiple rollers adapted to hold one or more cylindrically shaped items (such as, but not limited to, vials or ampoules) such that as the rollers rotate, all the items in contact with the rollers will rotate. In this embodiment, there may be multiple imaging devices positioned to read between the rollers or on an axis parallel to the roller(s) axis in such a way that all the information printed or otherwise encoded onto the surfaces of the cylindrically shaped items present and rotating along with the rotating rollers will be read. As a user retrieves any of the items the absence of the cylindrically shaped item at a particular location may be recorded. By comparing the presence and absence of an item, the information about what item was retrieved may be ascertained.

In some embodiments, to provide any of the omnidirectional readers 110 described here, a number of different readers may be arranged about a periphery of the recess (or other housing) such that there is gapless coverage of the entire recess. If a single reader is unable to capture the full barcode, images from multiple readers may be stitched and/or otherwise combined to generate a full barcode. Such a design allows a user to dip or otherwise insert the barcode of the item into the recess in any orientation and have the barcode quickly scanned, eliminating the need of the user to carefully align the barcode with a single linear scanner. In some embodiments, in addition or in the alternative, to reading information from a barcode, the omnidirectional reader 110 may be configured to read other information. For example, an optical sensor of the omnidirectional reader 110 may be able to image and read text-based data, such as by performing optical character recognition on any imaged text from an item.

In some embodiments, the work surface, such as work surface 106, may also include and/or be in communication with a waste bin, a sharps bin, and/or a returns bin. These bins may be locked and only allow movement of the items inward while preventing items from being removed. These bins may include one or more sensors that further assist inventory control efforts. These sensors may be similar to those incorporated into the drawers 104 described above. For example, each of these bins may include vision sensors, weight sensors, RF readers, and the like that positioned within an interior of the bin, near an opening of the bin, and/or proximate a base of the bin. These sensors enable the bins to detect a number and/or type of item placed within the respective bin, which may be used in conjunction with the sensor data from the drawers 104, bins (such as bins 172), and/or work surface 106 to reconcile inventory counts. For example, if three vials of a medication are taken from an inventory control system, such as one of the inventory control systems 100, and three syringes are used to extract the medication from the vials, a waste bin may be expected to detect three empty (or partially empty) vials and the sharps bin may be expected to detect three syringes.

Additionally, by incorporating such sensors a weight of the bin and/or a count of the number of items within the bin may be used to determine when a sharps or waste bin is full and needs to be disposed of. Conventional sharps and waste bins are picked up on regular schedules and may be overflowing or barely utilized at the time of pickup and subsequent disposal. This results in inefficiencies that may be avoided by monitoring an actual capacity of the respective bins by using the sensors disclosed herein.

In one particular embodiment, a waste bin may be formed as part of an omnidirectional reader, such as one of the omnidirectional readers 110. For example, a trap door may be provided at a base of the recess of the omnidirectional reader 110. If a user wishes to waste an object, the user may operate an actuator (such as a button) that opens the trap door and allows an item to be inserted into the waste bin placed below the omnidirectional reader. In some embodiments, the omnidirectional reader 110 may then operate both as a reader for normal inventory control, as well as for tracking items that are inserted into the waste bin. For example, if the trap door is actuated, the omnidirectional reader 110 may operate as a waste bin sensor.

Oftentimes, labels need to be created and affixed to certain items that are dispensed from an inventory control system, such as one of the inventory control systems 100. In some embodiments, when an item is detected and identified by one or more of the sensors of a work surface, such as work surface 106, a computing device, such as computing device 112, may send an indication of the presence of the item to a printing device (not shown), which may be present on and/or proximate the work surface 106. The indication may include identification information of the item, a patient associated with the item, a task or procedure associated with the item, a location of dispensing and/or use of the item, a time of use or dispensing of the item, and/or other information may be useful to provide on a label. The printing may then automatically print a label that may be affixed to the item. As just one example, a user may insert an item having a barcode into the omnidirectional reader. Once the reader identifies the item, an indication that includes information associated with the item is sent to the printing device. The printing device then prints a label that the user affixes to the item, such as by removing a releasable liner from the back of the label to expose an adhesive that secures the label onto the item. In some embodiments, rather than being automated, the printing process may require a confirmation from the user. For example, the user may need to interact with the computing device 112 (via interaction with a physical input device and/or voice control) to have the label printed.

The arrangement of features on the smart surface is often provided to provide the most robust sensor coverage without having designated areas that are required for use in order for a particular sensor to be utilized (with the possible exception of the omnidirectional reader). This may be achieved by arranging the various sensors about the work surface 106 in a way that enables each type of sensor to read items place on all or a significant part of the work surface 106. Such an arrangement enhances the ease of the user as the user does not have to think about the sensor placement when utilizing the smart surface. However, in some embodiments, it may be desirable to have predefined areas for one or more functions (emergency, waste, reading, labeling, etc.), which may make it easier to place the various sensors. For example, in some embodiments, it may be difficult to position load cells and a transparent base for the imaging devices in a single area. Therefore, designated areas for items that need to be imaged and/or weighed may be assigned.

IR Sensing

Figure 43:
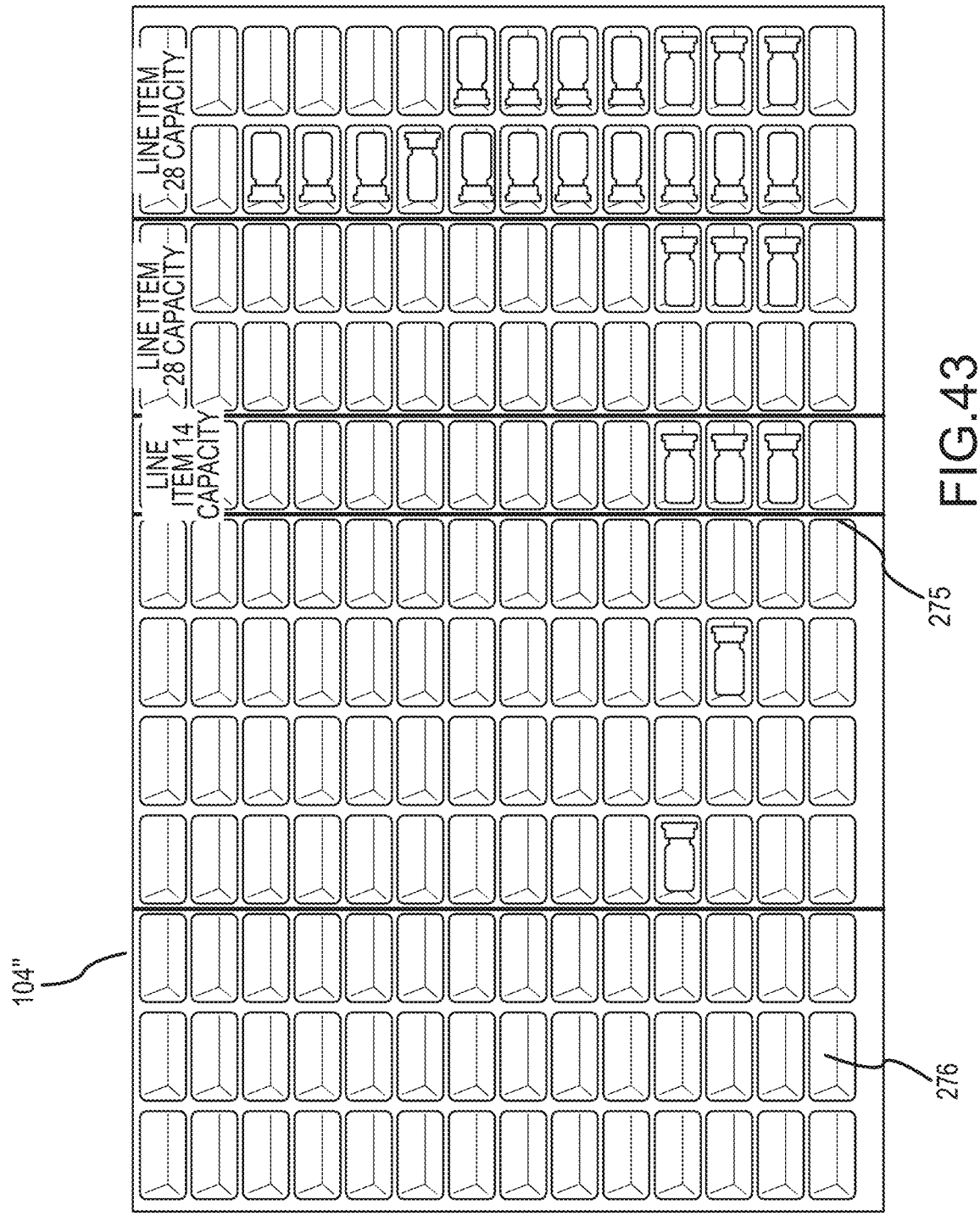
FIG. 43 illustrates an open matrix drawer having locating troughs according to embodiments of the present invention.

As illustrated in FIG. 43, some embodiments of open matrix drawers 104" may have locating troughs 276 that include IR reflective sensors (not shown). The state of each trough 276 may be scanned to count items within a given drawer 104. The bold lines represent configurable line item separators 275. In some embodiments, multiple troughs 276 may be needed to accommodate all the different vial sizes. The capacity of a single line item may be user-adjustable by combining and/or separating troughs 276 from different columns to produce troughs 276 of a desired size. The separators 275 may be taller than the trough walls to keep items from jumping across, and to assist the user to restock. Regardless of which trough 276 a user picks from, the inventory control system 100 knows the item count. For example, by using IR sensors, the contents may be continuously scanned and monitored for when a user removes and/or replaces items (such as taking a full vial and potentially returning an empty vial). In some embodiments, each column may include a guiding light that illuminates to direct users which column to pick from. In instances where multiple column line items have been combined to create larger troughs 276, the guiding lights for all columns forming the larger trough 276 may be illuminated to direct the user to the item.

Sensor Fusion

Oftentimes, a single drawer, such as one of the drawers 104, and/or a bin, such as a bin 172, of an inventory control system, such as one of the inventory control systems 100, may be monitored by various sensors, such as those described above (vision sensors, load sensors, RFID readers, and the like). Any combination of the above-described sensors and/or other sensors may be utilized in a particular inventory control system 100. For example, the reconciliation of information from multiple sensors may involve combinations of a number of raw features and/or derived features. Raw features may include a weight of an item and/or an image of contents of a particular bin and/or drawer, while derived features may include shape, texture, sectional images, perceived depth, variability of measurement (such as deviation), and/or spectral signature as detected by various sensors. As just one example, a single bin 172 may be monitored using designated load cells and a drawer 104 in which the bin 172 is located may be monitored using one or more vision sensors. By comparing the data from multiple sensors, the inventory control system 100 can more accurately inventory items that are present, added, and/or removed from a particular bin 172 and/or drawer 104. Similarly, data from sensors in different areas of the inventory control system 100 may be used to verify the accuracy of inventory counts. For example, data from sensors associated with one or more drawers 104 and/or bins 172 may be compared against information from sensors integrated into the work surface 106 and/or continuers (such as sharps, waste, and/or returns bins). In operation, a computing device, such as computing device 112, may gather data from some or all of the sensors present in the inventory control system 100, make any desired comparisons of the data, reconcile any different in counts provided by the different sensors, and update the inventory of the inventory control system 100.

In situations where the data from multiple types of sensors as well as the items selected by the easer at the computing device 112 all indicate the same item counts, the computing device 112 may determine that the inventory counts are all accurate. For example, the computing device 112 may know information about each item within the inventory control system 100, such as an item description, a weight, shape, size, etc. Images from vision sensors may be used to identify a quantity of a particular item based on an analysis of the images that look for how many items have a size, shape, etc. that match known characteristics of the particular item. Load sensors may be used to count the number of items in a designated bin 172 based on the known weight of the item. The counts from the image sensors and the load sensors may be compared. When the values match, the computing device 112 may determine that the count is accurate.

However, when there are discrepancies in some or all of the sensor measurements (and/or with the user's computer selections), the computing device 112 may perform an analysis to determine which data should be trusted. For example, in an embodiment which one or more vision sensors and one or more load sensors disagree as to a count of a particular item, the computing device 112 may consider confidence scores of the vision detection and the load detection to determine which sensor or set of sensors is likely more accurate. As detailed above, during object detection, a confidence score is assigned based on how likely the computing device 112 thinks a detected identity of an item matches the actual item. A similar confidence score may be computed for each load measurement.

For example, for a bin 172 that contains items that each weigh approximately 20 grams. Therefore, the computing device 112 expects load measurements that are factors of 20. If the load measurement is approximately a factor of 20, a high confidence score may be assigned as the likelihood of the measurement being accurate is high. As the deviation of the load measurement from expected values, the confidence score decreases. In some embodiments, the confidence factor for a load sensor may be based at least in part on an error factor of the load sensors themselves. As just one example, the load sensors may be accurate to within a percentage (such as 10%). If the total load detected is within the error factor of an expected value, the confidence level may be high and if the total load is outside of the error factor the confidence level may be lower. For example, if the load sensors have an error factor of 5%, each item weighs 20 grams, and the load sensors detect a load of 95 grams, there is a high likelihood that there are five items in the bin 172, as the load measurement is within 5% of the expected load for five items. Conversely, if the load sensors detect a load of 90 grams, it is unclear whether four or five items are present, as the value falls directly between the two expected values and is outside of the error factor. Therefore, the computing device 112 may assign a low confidence score in such a case.

To rectify discrepancies between the vision and load cells in such cases, whichever determined count has a higher confidence level may be chosen. In other embodiments, different rules may be used to rectify discrepancies. For example, the computing device 112 may choose the lower item count to error on the side of having enough items available for the user. For example, if one type of sensor indicates that five of a particular item are available and another sensor indicates that four of the item are available, the computing device 112 may determine that four of the item are present. This ensures that any amount of a particular item selected by the user at the computing device 112 is actually present within the inventory control system 100. For example, when selecting the items for removal at the computing device 112, the user is presented with the option of taking up to four of the item. If the first sensor is correct, one extra item will remain. If the second sensor is correct, the user may take all of the items without coming up short.

In some embodiments, the use of multiple sensor types in a single inventory control system 100 may be further useful to remedy potential deficiencies of a particular sensor type. For example, if the object detection process from images from one or more vision sensors detects (or cannot see) items that are stacked atop one another, data from sensors such as load sensors may be used to more accurately count the stacked items. Similarly, the use of RFID tags applied to items leaves the possibility that a user may tear off the RFID tag from one or more items and leave the tags within a drawer 104 while taking the items themselves. In such cases, an RFID reader would still read the items as being present within the drawer 104 since the RFID tags are still present. This may be particularly true in instances where valuable items, such as narcotics, are stored in a drawer 104. To eliminate this possibility, vision and/or load sensors may also be used to monitor the items within the drawer 104. This way, if a user removes the RFID tags and places them back in the drawer 104, the vision and/or load sensors will be able to detect that the items themselves have been removed.

Figure 44:
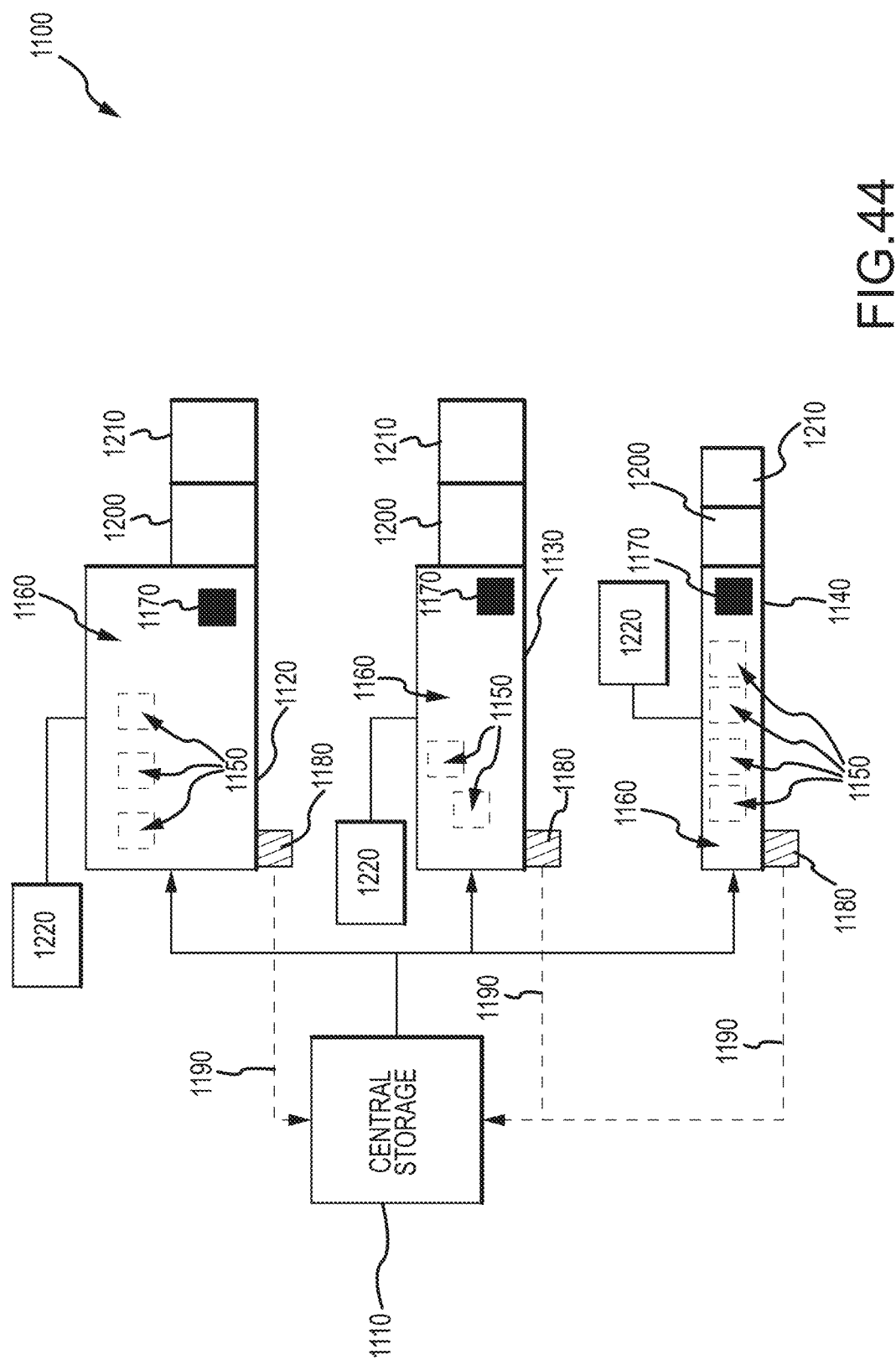
FIG. 44 illustrates a block diagram of an inventory control system according to embodiments of the present invention.

In accordance with yet another embodiment as shown in FIG. 44, an inventory control system 1100 (which may be similar to one of the inventory control systems described herein) may include one or more storage modules 1160 (which may be similar to the drawers 104). Any of the storage modules 1160 may be in the form of a cabinet 1120 with shelves and doors in one example. In another example, these storage modules may be in the form of a cabinet 1130 with drawers. In yet another example, these storage modules may be in the form of a mobile cabinet 1140 with drawers. Ultimately, the function of these storage modules 1160, generically, or 1120-1140 specifically, is to hold one or more units of one or more types of items 1150. In one example of a hospital setting, these items 1150 may be in the form of medications in different forms such as: vials, ampoules, ointments, tablets, capsules, and/or may also include equipment such as syringes, alcohol pads, cotton balls, IV bags, bandages, etc.

In one embodiment, any of the storage modules 1120, 1130, 1140 may allow unrestricted access to the one or more items 1150 stored within the storage modules to any user who wishes to access the items 1150. This means that the user may not necessarily provide any authentication via any form of credentials to be able to retrieve the one or more items 1150.

In another embodiment, one or more of the storage modules 1120-1140 may have one portion of its items restricted for access to only authorized users, while another portion of items within the storage module may be available for unrestricted access. It may be assumed that, in such an embodiment, the different portions within the storage module allowing restricted and unrestricted access may not carry identical items 1150.

In yet another embodiment, any of the storage modules 1120-1140 may require an authorized user to provide one or more user credentials and/or biometric credentials before gaining access to the contents of the storage module. Once access into the storage modules has been gained, the user may be able to retrieve one or more items 1150 from any restricted and/or unrestricted spaces within the storage module.

In a further embodiment, any of the storage modules 1120-1140 may comprise of only items 1150 that are access-controlled and restricted. In some embodiments, such items 1150 stored within the storage modules 1120-1140 may all be controlled substances like narcotics which are required for specific, doctor-prescribed treatments. All of these embodiments are meant as exemplary and it is possible for parts of the above embodiments to be represented within any storage module 1120-1140 interfacing with the inventory tracking system as described herein.

Where applicable, the inventory control system 1100 may include an access control system 1170 designed to allow an authorized user to selectively access the one or more storage modules 1120-1140. Access control system 1170 may include one or more of a graphical user interface to receive a username and/or password identifying the user, a biometric scanner (such as an iris scanner, a fingerprint scanner, and/or a face scanner), and/or sensors configured to detect wearable and/or other possession-based authentication devices, which may utilize RFID, blue tooth, and/or NFC-based identification technology.

The inventory control system 1100 may further include an inventory monitoring module 1180 to monitor any of the acts of: (a) adding one or more items 1150 into the storage modules 1120-1140, (b) removing or retrieving one or more items 1150 from the storage modules 1120-1140, (c) tracking consumption of the retrieved items 1150, (d) returning of any unused/unopened items 1150 back into the storage module, and/or (e) discarding of retrieved item 1150 when none, some, or all portions of the contents within the retrieved item 1150 have been used. A return is when the item 1150 has not been opened and/or has not had its integrity compromised. A discard is when the integrity of the item 1150 has been compromised. The integrity of an item 1150 may be compromised by any of the following ways: (a) when the temperature at which the item 1150 is required to be maintained has been exceeded beyond an acceptable duration, (b) when a safety seal of an item 1150 was removed before a decision was changed pertaining to use of the item 1150 (while the item 1150 was never used, the item's safety seal was breached and therefore, the item 1150 cannot be used for a different purpose at a different point in time), and/or (c) when a portion of the content(s) within the item 1150 was used and the remainder of the content cannot be re-used. These are just a few examples of ways in which integrity of an item 1150 may be compromised that will require the item 1150 to be discarded rather than be re-used. Of course, the nature of the item 1150 and its content may require a different treatment of the item 1150/content that may alter the determination as described above, and such deviations may be considered as being within the scope of the present invention.

The inventory control system 1100 is configured to perform one or more of the following tasks by a user: identifying a user who interacts with one or more of the storage modules, adding items to one or more of the storage modules, retrieving one or more items 1150 from at least one of the storage modules, preparing one or more items 1150 for later use and/or consumption, returning one or more unused items 1150, and/or discarding one or more used and/or unused items 1150. More detailed disclosure of each of these tasks is provided below from the perspective of a hospital environment using an embodiment of the inventory control system 1100. However, the following disclosure should not be considered as limiting. Based on specific applications, the inventory control system 1100 described herein may be modified to suit the needs of a particular application. Since the inventory tracking system 1100 includes the processing of multiple streams of data, pertaining to and characterizing each of the above tasks for the one or more storage modules, it is envisioned that such storage modules 1120-1140 may include the ability to receive and process the data locally at the storage module level itself. For such purposes, each storage module 1120-1140 is equipped with a configurable processing capability 1220. It may be considered as either a computer configured to receive data streams from the various elements within the storage module 1120-1140 to characterize any or all of the above tasks specified above. Each of the above tasks is also described in detail herein below.

Identifying a User

A user may be identified based on user credentials either provided by the user or automatically detected by the inventory tracking system 1100. Various forms of user credentials include: (a) username and/or password to be used to gain access to the one or more storage modules 1120-1140, (b) biometric identification based on voice, fingerprints, facial recognition, and/or iris scanning, (c) contactless authentication using a wearable device and/or a device that can be carried by a user that uses near field communication (NFC) technologies, Bluetooth, and/or RFID technology to deliver user credentials to the inventory control system 1100.

Addition of Items into the Storage Module

Items 1150 may be added into the one or more storage modules 1120-1140 as part of a re-stocking operation. Typically, in a hospital setting, where the storage modules hold medications, this act of adding items is performed by a pharmacy technician as part of their scheduled task of restocking the storage modules 1120-1140 based on consumption or demand of the one or more items 1150. These items 1150 may be in the form of oral solids, capsules, ointments, vials, ampoules, IV bags, aerosol, etc. as well as consumables such as syringes (of various capacities), catheters, procedural assist tools and/or devices such as respirator valves, needles, tubes, scopes, etc. While the traditional aspect of restocking also involves manually entering the quantity and details about the items 1150 being restocked, in the present technique, the added items 1150 are automatically identified based on a name and/or description of an item, as well as how many of the items 1150 were added. The inventory control system 1100 described herein generates accurate knowledge of the inventory held within the one or more storage modules 1120-1140.

Addition of one or more items 1150 into the one or more storage modules 1120-1140 may be performed by a user for the purposes of re-stocking the storage modules 1120-1140 for later use. In a hospital environment, such storage modules 1120-1140 may be used for storing a variety of medications and devices that may be used in any medical procedure or treatment of any medical condition. In one embodiment, a pharmacy technician may be assigned the task of re-stocking the contents of any storage module 1120-1140 based on specific knowledge of the inventory levels within the storage module 1120-1140. It may be expected that when the pharmacy technician adds items 1150 to replenish the inventory within the storage modules 1120-1140, there will be available space within the storage module 1120-1140 to receive the added items 1150. The addition of an item 1150 may be determined by any of the following ways: (a) the presence of a free space within a bin and subsequently its occupation by an item 1150, (b) identification of the added item 1150 by determining the size, shape, or by reading any available information in human-readable (text labels) or machine-readable formats (such as barcode, QR code, and/or numbers). For such a purpose, the inventory monitoring module 1180 may be in the form of one or more imaging devices that are each adapted to capture an image of the space where the items 1150 are added. Using image analytics that require the determination of the size, shape of the item 1150, as well as reading one or more labels identifying the added items 1150, the inventory monitoring module 1180 is able to determine what items 1150 were added to the storage module 1120-1140 by the user. In the present embodiment, when adding items into the one or more storage modules 1160, information 1190 that represents data quantifying the addition of the items (i.e., the identification, quantity, as well as other determinable characteristics about the added items) may be sent to a central storage 1110, which may be in the form of a central pharmacy 1110. In one example (not shown), the information 1190 may be aggregated locally at the storage module level (1120, 1130, and/or 1140) and then relayed to the central pharmacy 1110. This aggregation and transmission of information 1190 may be performed at specific times of the day (every day at 3 pm as an example), at specific intervals of time (every 2 hours as an example), upon the occurrence of specific activities (at the completion of a specific procedure or process of admission as examples), and/or at the request of the central pharmacy 1110 (requesting the status of inventory at the storage module 1160 as an example). In another example, as shown in the figure, the information 1190 may be directly relayed to central pharmacy 1110.

Removal or Retrieval of Items from the Storage Module

During any particular procedure, a doctor, a nurse and/or an anesthesiologist may require one or more items 1150 from the storage modules 1120-1140 to be retrieved. While a traditional process may require a separate workflow to access some of the contents within the storage modules 1120-1140, in the present technique the user may be able to simply walk up to the storage module, access the items 1150 within the storage modules 1120-1140 and retrieve the required items 1150. The inventory control system 1100 as envisioned herein is configured to detect and identify the user as the user approaches the storage module 1120-1140, and uses one or more aspects of the user to identify the user, such as fingerprint scanning, iris scanning, facial recognition, voice recognition, or credential-based authentication based on information made available via a wearable or a device that may be carried by a user (such as an ID badge, an RFID sensor, an NFC or a blue tooth sensor). As the user retrieves one or more items 1150 from the storage modules 1120-1140, the removed item 1150 may be identified based on optical identification of the item 1150. For example, as the item 1150 is removed, imaging devices may be used to identify features on the item 1150, such as a label, a barcode, and/or any other coded information on the item to identify the item 1150. In another example, imaging devices may instead scan the storage modules 1120-1140 to determine the item based on what item 1150 is missing when compared with a previously inventoried state. In yet another example, the retrieval of an item 1150 from within the storage modules 1120-1140 may be determined based on a weight change in a storage space within the storage modules 1120-1140 where the retrieved item 1150 was previously stored, prior to its retrieval. In yet another example, a combination of any of the above ways of determining a retrieved item 1150 may be used to increase the accuracy of the information determined to confirm what item 1150 was removed as well as how many of the item 1150 were removed. In the present embodiment, when removing items from the one or more storage modules 1160, information 1190 representing data quantifying the addition of the items (i.e., the identification, quantity, as well as other determinable characteristics about the removed items) may be sent to the central pharmacy 1110. In one example (not shown), the information 1190 may be aggregated locally at the storage module level (1120, 1130, and/or 1140) and then relayed to the central pharmacy 1110. This aggregation and transmission of the information 1190 may be performed at specific times of the day (every day at 3 pm as an example), at specific intervals of time (every 2 hours as an example), upon the occurrence of specific activities (at the completion of a specific procedure or process of admission as examples), and/or at the request of the central pharmacy 1110 (requesting the status of inventory at the storage module as an example). In another example, as shown in the figure, the information 1190 may be directly relayed to central pharmacy 1110.

Return of an Unused Item

In a hospital environment, when a retrieved item 1150 is not used (i.e., its secure packaging was not compromised), the item 1150 may be reused for a later need even if it is for a different patient. However, nurses or doctors are encouraged to not re-stock the storage modules 1120-1140 themselves. Instead, they are instructed to use a separate storage unit called a return bin 1200 to place the unused medications. At a later point in time, a pharmacy technician retrieves the returned items 1150 and consolidates such items 1150 back into the hospital inventory. However, it must be appreciated that on a daily basis, a good portion of a pharmacy's inventory may reside in the return bin 1200. The present technique includes ways to identify an item 1150 that has been placed in the return bin to create an inventory level in about real-time that allows a pharmacy to better manage its medications. While the present technique is useful in the described context, it may further be appreciated by a person skilled in the art that the present technique further may allow a new workflow that dramatically increases the efficiency of the operation, i.e., allows a user to directly re-stock a storage module 1120-1140 with any unused item, enabling its re-use without tracing its way back to the central pharmacy 1110 and/or other central storage 1110 and being loaded back into the storage module 1120-1140 as part of a scheduled re-stocking operation.

Figure 45A:
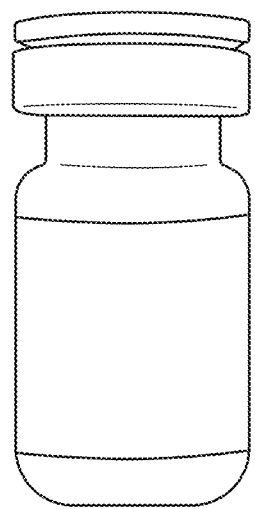
FIG. 45A illustrates an item having identifiers that are not visible within the visible spectrum according to embodiments of the present invention.
Figure 45B:
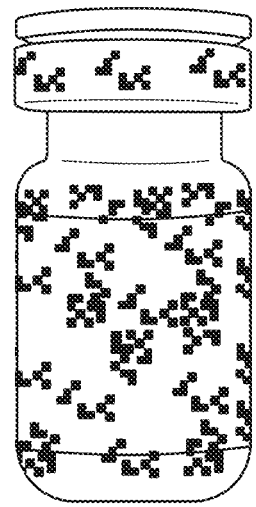
FIG. 45B illustrates the item when viewed under IR or UV light.

In order to allow accurate identification by the imaging devices, the label on the item 1150 may be readable using light in a particular range of wavelengths outside the visible spectrum, such as infrared or ultraviolet light. Under normal lighting conditions, such labels may not even be visible to a user as illustrated in FIG. 45A. However, under special lighting conditions that match the wavelength that allows the label to become readable as shown in FIG. 45B, the tuned imaging devices are able to read the label and determine the identity of the added item 1150. By covering an item 1150 with machine-readable codes, such as QR barcodes, the item 1150 can be identified regardless of its orientation. For example, some embodiments may provide machine-readable codes that are printed over the original item label using visible spectrum transparent ink. In such embodiments, any human-readable information from the original label is still unobscured and visible to humans, while the information provided using the transparent ink may be read by an optical reader of a computing device. The computer-readable information may include a pointer to a database that contains the complete item information including lot and expiration date and/or some or all of the item information could be encoded directly in the barcode. Turning back to FIG. 44, when the storage module 1120-1140 already has items 1150 stored within it, and new items 1150 are being added, the inventory monitoring module 1180 may use image analytics that determine the items 1150 added by comparing the contents of the storage module 1120-1140 before the act of addition and after the act of addition. This information, coupled with the information about the newly-added items 1150, reveals the quantity of each item 1150 added to the storage module 1120-1140. Such techniques may be effectively applied for verifying the item 1150.

Discard of any Used Item

With medications being packaged into specific units or doses, it is reasonable to anticipate that not all retrieved items 1150 from a storage module 1120-1140 are fully consumed. For example, when a 10 ml vial of a medication is retrieved for use in administering only 5 ml of the medication to a patient, the remaining 5 ml of the medication cannot be reused for a different patient or for the same patient at a different time. In such a case, the remaining 5 ml of the medication, as well as the vial, must be discarded into a waste or discard container 1210. Tracking of discard becomes more significant when the medication is a controlled substance, particularly one that requires greater control and tracking. In such a scenario, it is important to identify both the consumption of the controlled substance and the discard of the controlled substance. For example, if 5 ml of morphine is required to be administered to a patient from a 10 ml vial, there must be a proper accounting procedure to confirm and document that 5 ml was administered and that 5 ml was discarded. In some cases, this requires a witness, typically a fellow member of the medical staff, to confirm the consumption and discard. Some embodiments may involve the identification of the medication using a chemical identification process such as, but not limited to, using a Raman spectroscopy system and/or refractometry during the discard process. While the figure illustrates that every storage module 1160 is equipped or associated with a discard container 1210, it must be envisioned that the discard container 1210 may not always be present with the storage module 1160 or be an integral part of the storage module 1160. Such variations of associations must be construed as being within the scope of the present invention. In accordance with one specific embodiment, the discard container 1210 may be a separate container that is common and shared between two or more storage modules 1160 as well.

In some embodiments, an inventory control/tracking system, such as those described above, may be integrated into a mobile storage workstation or module 300 such as, but not limited to, an anesthesia workstation. FIGS. 46A and 46B illustrate a mobile storage module 300 that includes one or more drawers 310, which may be similar to the drawers 104 described above. Each drawer 310 includes one or more storage spaces. When the storage spaces are open, i.e., allowing direct access to the contents within the storage spaces (such as bins 172) each such storage space is called an "open bin." When there are multiple such bins within the drawer 310, the drawer 310 may be identified as having "open-matrix bins." Alternatively, when the storage spaces do not allow direct access to the contents within them, i.e., the bins have an additional level of access restriction in the form of a lid that can be locked or unlocked, then such storage spaces, also called "bins," are called "lock-lidded bins." It will be appreciated that in some embodiments, a single drawer 310 may include a combination of open bins and lock-lidded bins.

Included as part of the mobile storage module 300, as embodied herein, is an illumination unit 302 that also integrates one or more imagers 304 (such as imaging devices that are capable of capturing photographic and/or videographic information) and one or more light sources 306. Imagers may include depth measurement technology to aid the counting of items in the event objects overlap and/or occlude each other. The illumination unit 302 is adjustable for height but is typically meant to be above 6 feet in height so as to avoid intruding or being in the way of a user. Imagers 304 may be used for multiple purposes such as: (a) identifying a user who is interacting with the storage module as well as (b) identifying the nature of the interaction—adding new items, removing an item, preparing a new item based on the retrieved/removed item, returning an unused or untampered item, and discarding an item. The light sources 306 may also be used to provide illumination to allow the imagers 304 to better perform their task and to provide specialized identification as described below.

The imagers 304 may use lighting from multiple spectrums or just a single spectrum. This may require the use of more than one imaging system that can capture images at different wavelengths. Similarly, the light sources 306 may be configurable to illuminate using more than one wavelength, including wavelengths beyond visible range, such as infrared or ultraviolet.

The field of view of the one or more imagers 304 and the field of illumination of the one or more light sources 306 are configurable to ensure complete coverage of the drawer 310 when it is in a fully open position. The imagers 304 are also able to automatically alter/adjust their focus based on the height of any particular drawer 310. In accordance with one aspect of the present invention, the one or more imagers 304 are triggered based on specific gestures or movement of the hand and/or the drawer 310. For example, when a hand and a drawer 310 are both moving outward (away from the storage module 300), the determination may be that the drawer 310 is being opened. When the hand is moving over the drawer, the determination may be that a user is attempting to add, remove or move an item stored within the drawer 310. When the hand and the drawer 104 are both moving inward (i.e., towards the storage module 300), the determination may be that the drawer 310 is being closed. Such gesture-based detection may allow the storage module 300 to determine how to process any of the captured videos/images by the one or more imagers 304. The drawer closing can be detected by a positional sensor, accelerometer, and/or analysis of video from the imagers 304, for example.

In accordance with another embodiment, the imagers 304 may be configured to capture a single image of the entire drawer 310 at two different times, such as when the drawer 310 is fully open, and when the drawer 310 is detected as closing. Subsequently, the two different images are compared to determine the presence or absence of any particular item. It is also possible for the imagers 304 to take more than two images to make the determination. Consider, as an example, that the imagers 304 take a first image at the start of opening of the drawer 310, a second image when the drawer 310 is fully open, a third image when a hand motion is detected moving towards the drawer 310, a fourth image when the hand is seen adding or removing or moving one or more items when over the drawer 310, and/or a fifth image when the hand is detected to be moving away from the drawer 310. In another example, the imagers 304 may perform a videographic capture as opposed to a photographic capture, capturing the entire sequence of operations starting with the opening of the drawer and end with the closing of the drawer 310. In another embodiment, a machine learning algorithm may be trained to recognize the items that are to be identified. Video from the imaging system will be processed by the machine learning algorithm to identify the objects of interest.

While the use of the imagers 304 for imaging the drawers 310 may seem highly relevant to open matrix bins, such an arrangement may also work well for lock-lidded bins. For such an application, the lids that cover each of the bins within the drawers 310 may be designed as being transparent to allow the imager 304 to image the contents of the bin, by viewing through the lid. In one particular embodiment, the lid may be made of a material transparent in the visible light spectrum, i.e., illumination by visible light reveals the contents within the lock-lidded bins when the lids are closed. In a different embodiment, the lid may be transparent to a particular wavelength of light (non-visible wavelength), such as to infrared, near-infrared, far-infrared, or ultraviolet or beyond ultraviolet, while being translucent or opaque in the visible light spectrum (visible to humans), i.e., when light at the appropriate wavelength is focused on the top of the lock-lidded bins, the contents within the bins are revealed, although not to a user. Such a reveal may be captured by a special imaging system, such as an imaging device designed to capture images at a particular wavelength of light. In some instances, the same imaging device may be configured to capture images across multiple wavelengths, including on either side of the visible spectrum. In other instances, there may be multiple imaging devices, each designed to capture images at a particular range of wavelengths.

In yet another embodiment of the present invention, the inventory tracking systems (such as inventory control systems 100 and 1100) may further include the ability to track the lifecycle of an item. For example, in an embodiment in a hospital environment in which a central pharmacy (such as central pharmacy 198) has the responsibility to ensure that the right medications are available for use at any of the medication cabinets (fixed or mobile) at any of the floor or patient areas within the hospital or across a system of hospitals. The inventory tracking system may provide significantly enhanced visibility of the status of inventory across one or more medication storage units. In a typical setting, the central pharmacy performs a re-stocking of the one or more medication storage units on a daily basis, although specific practices and workflows within specific hospitals may vary the frequency of such re-stocking activities based on the time of the year, the complexity of treatments performed, the seasonal infectious diseases, and/or based on the nature of the treatment being provided to the patients. While there will be variation, it can be envisioned that knowledge of inventory levels within the one or more medication storage units can reduce wasteful workflows that take medications to cabinets that are well stocked and consequently, delay the re-stocking of all such medication storage units across a hospital due to such inefficiencies.

As part of the present embodiment, the inventory tracking system is able to provide accurate levels of inventory of medications within the one or more medication storage units. When the right inventory is known, the central pharmacy is able to prioritize the delivery of the right medication to the right storage unit with a faster completion of the re-stocking. When re-stocking is completed across the cabinets across a hospital, a significant quantity of the hospital's medication inventory may be held in these cabinets. While the knowledge of the inventory held within the cabinets may be highly desirable, such knowledge can be significantly enhanced with additional knowledge of how much is being consumed (or retrieved from the cabinets), by who, and/or for which patient. An additional level of information that adds even more value is knowing how much was not used (i.e., returned in the return bin) or discarded (i.e., discarded in the discard container). Some or all of this information enables a hospital's central pharmacy to gain a significantly powerful insight into the actual medication inventory within the hospital.

For example, actual hospital inventory is equal to medication stored in the medication cabinets minus medication retrieved for consumption plus medication returned (due to non-consumption). The quantity of medication or containers of the medication discarded provides additional visibility on the accountability of medication consumption. This may be particularly useful when tracking the consumption of controlled substances or specific medications of high value.

Some or all parts of the determination may be performed using one or more inventory tracking modules that include one or more sensors (imaging, image-based identification, weight detection, or the combinations of the above) as described herein. The previously described embodiment describing the aspects of tracking the acts of adding items, removing items, consuming the items, returning the items and/or discarding the items may be appropriately deployed with the right modifications to assist in generating the information about an accurate hospital inventory as described herein.

Figure 47:
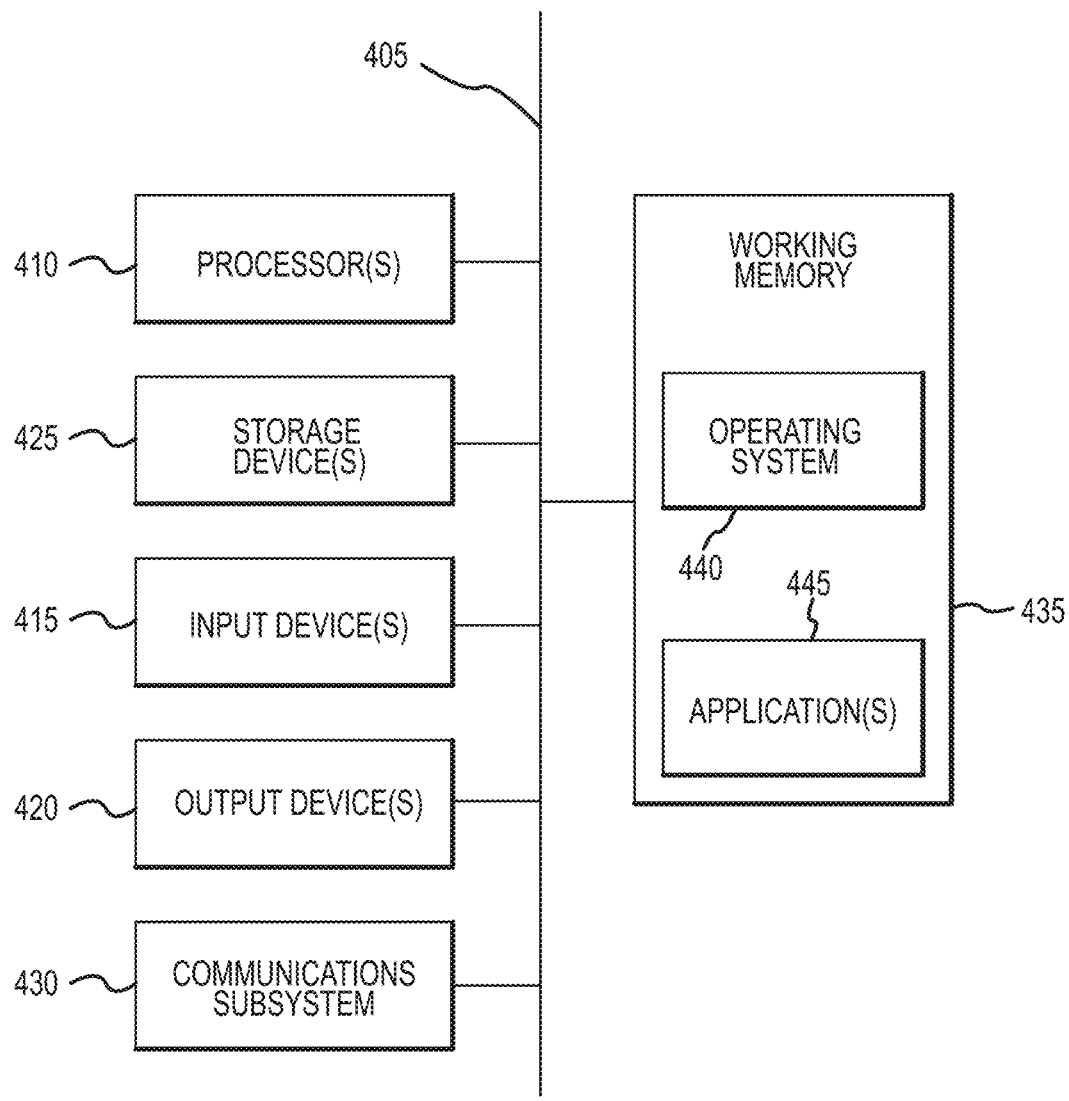
FIG. 47 is a block diagram of a computing system according to embodiments of the present invention.

A computer system as illustrated in FIG. 47 may be incorporated as part of the previously described computerized devices. For example, computer system 400 can represent some of the components of computing device 112 and/or other computing devices described herein. FIG. 47 provides a schematic illustration of one embodiment of a computer system 400 that can perform the methods provided by various other embodiments, as described herein. FIG. 47 is meant only to provide a generalized illustration of various components, any or all of which may be utilized as appropriate. FIG. 47, therefore, broadly illustrates how individual system elements may be implemented in a relatively separated or relatively more integrated manner.

The computer system 400 is shown comprising hardware elements that can be electrically coupled via a bus 405 (or may otherwise be in communication, as appropriate). The hardware elements may include a processing unit 410, including without limitation one or more processors, such as one or more special-purpose processors (such as digital signal processing chips, graphics acceleration processors, and/or the like); one or more input devices 415, which can include without limitation a keyboard, a touchscreen, receiver, a motion sensor, an imaging device, a smartcard reader, a contactless media reader, and/or the like; and one or more output devices 420, which can include without limitation a display device, a speaker, a printer, a writing module, and/or the like.

The computer system 400 may further include (and/or be in communication with) one or more non-transitory storage devices 425, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 400 might also include a communication interface 430, which can include without limitation a modem, a network card (wireless or wired), an infrared communication device, a wireless communication device and/or chipset (such as a Bluetooth™ device, an 502.11 device, a Wi-Fi device, a WiMAX device, an NFC device, cellular communication facilities, etc.), and/or similar communication interfaces. The communication interface 430 may permit data to be exchanged with a network (such as the network described below, to name one example), other computer systems, and/or any other devices described herein. In many embodiments, the computer system 400 will further comprise a non-transitory working memory 435, which can include a RAM or ROM device, as described above.

The computer system 400 also can comprise software elements, shown as being currently located within the working memory 435, including an operating system 440, device drivers, executable libraries, and/or other code, such as one or more application programs 445, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such special/specific purpose code and/or instructions can be used to configure and/or adapt a computing device to a special purpose computer that is configured to perform one or more operations in accordance with the described methods.

A set of these instructions and/or code might be stored on a computer-readable storage medium, such as the storage device(s) 425 described above. In some cases, the storage medium might be incorporated within a computer system, such as computer system 400. In other embodiments, the storage medium might be separate from a computer system (e.g., a removable medium, such as a compact disc), and/or provided in an installation package, such that the storage medium can be used to program, configure and/or adapt a special purpose computer with the instructions/code stored thereon. These instructions might take the form of executable code, which is executable by the computer system 400 and/or might take the form of source and/or installable code, which, upon compilation and/or installation on the computer system 400 (e.g., using any of a variety of available compilers, installation programs, compression/decompression utilities, etc.) then takes the form of executable code.

Substantial variations may be made in accordance with specific requirements. For example, customized hardware might also be used, and/or particular elements might be implemented in hardware, software (including portable software, such as applets, etc.), or both. Moreover, hardware and/or software components that provide certain functionality can comprise a dedicated system (having specialized components) or may be part of a more generic system. For example, a risk management engine configured to provide some or all of the features described herein relating to the risk profiling and/or distribution can comprise hardware and/or software that is specialized (e.g., an application-specific integrated circuit (ASIC), a software method, etc.) or generic (e.g., processing unit 410, applications 445, etc.) Further, connection to other computing devices such as network input/output devices may be employed.

Some embodiments may employ a computer system (such as the computer system 400) to perform methods in accordance with the disclosure. For example, some or all of the procedures of the described methods may be performed by the computer system 400 in response to processing unit 410 executing one or more sequences of one or more instructions (which might be incorporated into the operating system 440 and/or other code, such as an application program 445) contained in the working memory 435. Such instructions may be read into the working memory 435 from another computer-readable medium, such as one or more of the storage device(s) 425. Merely by way of example, execution of the sequences of instructions contained in the working memory 435 might cause the processing unit 410 to perform one or more procedures of the methods described herein.

The terms "machine-readable medium" and "computer-readable medium," as used herein, refer to any medium that participates in providing data that causes a machine to operate in a specific fashion. In an embodiment implemented using the computer system 400, various computer-readable media might be involved in providing instructions/code to processing unit 410 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media include, for example, optical and/or magnetic disks, such as the storage device(s) 425. Volatile media include, without limitation, dynamic memory, such as the working memory 435. Transmission media include, without limitation, coaxial cables, copper wire, and fiber optics, including the wires that comprise the bus 405, as well as the various components of the communication interface 430 (and/or the media by which the communication interface 430 provides communication with other devices). Hence, transmission media can also take the form of waves (including without limitation radio, acoustic and/or light waves, such as those generated during radio-wave and infrared data communications).

Common forms of physical and/or tangible computer-readable media include, for example, a magnetic medium, optical medium, or any other physical medium with patterns of holes, a RAM, a PROM, EPROM, a FLASH-EPROM, any other memory chip or cartridge, a carrier wave as described hereinafter, or any other medium from which a computer can read instructions and/or code.

The communication interface 430 (and/or components thereof) generally will receive the signals, and the bus 405 then might carry the signals (and/or the data, instructions, etc. carried by the signals) to the working memory 435, from which the processor(s) 405 retrieves and executes the instructions. The instructions received by the working memory 435 may optionally be stored on a non-transitory storage device 425 either before or after execution by the processing unit 410.

The methods, systems, and devices discussed above are examples. Some embodiments were described as processes depicted as flow diagrams or block diagrams. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

It should be noted that the systems and devices discussed above are intended merely to be examples. It must be stressed that various embodiments may omit, substitute, or add various procedures or components as appropriate. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known structures and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

The methods, systems, devices, graphs, and tables discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims. Additionally, the techniques discussed herein may provide differing results with different types of context awareness classifiers.

While illustrative and presently preferred embodiments of the disclosed systems, methods, and machine-readable media have been described in detail herein, it is to be understood that the inventive concepts may be otherwise variously embodied and employed, and that the appended claims are intended to be construed to include such variations, except as limited by the prior art.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate to in the context of the systems, devices, circuits, methods, and other implementations described herein. As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A medication management workflow and control system, comprising:
    a support surface comprising two or more types of sensors that are configured to monitor use of an item, wherein the two or more types of sensors are selected from the group consisting of a load sensor, an imaging device, a radio frequency reader, and an optical reader; and
    at least one processor that is configured to:
        receive information from the two or more types of sensors;
        compare the information from the two or more types of sensors; and
        determine an identity of the item based on the compared information from the two or more types of sensors.

2. The medication management workflow and control system of claim 1, wherein:
    the two or more types of sensors comprise at least one load sensor;
    the at least one processor is configured to extract one or both of size information and a pressure map of contact points of the item based on information from the at least one load sensor; and
    the identity of the item is determined based at least in part on the one or both of the size information and the pressure map of contact points of the item.

3. The medication management workflow and control system of claim 2, wherein:
    determining the identity of the item based at least in part on the one or both of the size information and the pressure map of contact points of the item comprises comparing the one or both of the size information and the pressure map of contact points of the item to known item characteristics.

4. The medication management workflow and control system of claim 1, wherein:
    the support surface comprises a transparent region; and
    the two or more types of sensors comprise at least one optical sensor disposed beneath the transparent region such that a field of vision of the at least one optical sensor faces the transparent region.

5. The medication management workflow and control system of claim 1, further comprising:
    an omnidirectional reader coupled with the support surface, the omnidirectional reader being configured to scan at least a majority of an exterior surface of an object placed therein.

6. The medication management workflow and control system of claim 1, wherein:
    receiving information from the two or more types of sensors comprises receiving one or both of a lot number and an expiration date of the item.

7. The medication management workflow and control system of claim 6, wherein:
    the at least one processor is further configured to perform one or more checks based on the one or both of a lot number and an expiration date of the item, the one or more checks comprising at least one check selected from the group consisting of determining whether the item is appropriate for a given patient, whether a lot associated with the lot number has been recalled, and whether the item has expired.

8. A medication management workflow and control system, comprising:
    a support surface comprising two or more types of sensors that are configured to monitor use of an item, wherein the two or more types of sensors are selected from the group consisting of a load sensor, an imaging device, a radio frequency reader, and an optical reader; and
    at least one processor that is configured to:
        receive information from the two or more types of sensors;
        compare the information from the two or more types of sensors;
        determine an identity of the item based on the compared information from the two or more types of sensors; and
        automatically cause a label to be printed for the item upon determining the identity of the item.

9. The medication management workflow and control system of claim 8, further comprising:
    a waste bin comprising at least one sensor that is configured to detect a type of object that has been inserted within an interior of the waste bin.

10. The medication management workflow and control system of claim 9, wherein:
    the at least one processor is further configured to monitor a capacity of the waste bin based on data from the at least one sensor.

11. The medication management workflow and control system of claim 8, wherein:
    the two or more types of sensors comprise at least one load sensor; and
    the at least one processor is configured to compare a weight measurement from the at least one load sensor with an expected weight of the item to determine a quantity of material that has been removed from the item.

12. The medication management workflow and control system of claim 8, wherein:
    the two or more types of sensors are positioned to monitor a same region of the support surface.

13. The medication management workflow and control system of claim 8, wherein:
    the support surface is disposed atop a medical dispensing storage unit.

14. The medication management workflow and control system of claim 8, wherein:
    the at least one processor is further configured to compare the identity of the item with inventory data from one or more storage locations to verify an accuracy of the inventory data.

15. A computer-implemented method of managing medical workflow, comprising:
    receiving, by one or more processors of a medication management workflow and control system, information from two or more types of sensors that are positioned to monitor an item on a support surface, wherein the two or more types of sensors are selected from the group consisting of a load sensor, an imaging device, a radio frequency reader, and an optical reader;

comparing, by the one or more processors, the information from the two or more types of sensors; and determining, by the one or more processors, an identity of the item based on the compared information from the two or more types of sensors.

16. The computer-implemented method of managing medical workflow of claim 15, further comprising:

determining that the information from the two or more types of sensors does not match, wherein determining the identity of the item comprises analyzing a confidence score associated with the information from each of the two or more types of sensors and selecting the identity of the item based on a highest confidence score.

17. The computer-implemented method of managing medical workflow of claim 16, wherein:

each confidence score is based at least in part on an error factor of a respective sensor.

18. The computer-implemented method of managing medical workflow of claim 16, wherein:

the two or more types of sensors comprise at least one vision sensor that performs object detection to determine the identity of the item; and the confidence score of the at least one vision sensor is based on a likelihood that the object detection has correctly identified the item.

19. The computer-implemented method of managing medical workflow of claim 15, further comprising:

determining an expected weight of the item based on the identity of the item;

measuring an actual weight of the item; and determining an amount of the item that has been used based on a difference between the actual weight and the expected weight.

20. The computer-implemented method of managing medical workflow of claim 15, wherein:

determining the identity of the item comprises comparing one or both of size information and a pressure map to known item characteristics.

* * * * *